(12) United States Patent
Hamprecht et al.

(10) Patent No.: US 7,741,485 B2
(45) Date of Patent: Jun. 22, 2010

(54) BENZENESULPHONAMIDE DERIVATIVES AS HERBICIDES OR DESICCANT/DEFOLIANT COMPOUNDS

(75) Inventors: Gerhard Hamprecht, Weinheim (DE); Michael Puhl, Lampertheim (DE); Robert Reinhard, Ludwigshafen (DE); Werner Seitz, Plankstadt (DE); Cyrill Zagar, Mannheim (DE); Matthias Witschel, Bad Duerkheim (DE); Andreas Landes, Roemerberg-Heiligenstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 586 days.

(21) Appl. No.: 10/551,988

(22) PCT Filed: Apr. 6, 2004

(86) PCT No.: PCT/EP2004/003624

§ 371 (c)(1),
(2), (4) Date: Oct. 5, 2005

(87) PCT Pub. No.: WO2004/089914

PCT Pub. Date: Oct. 21, 2004

(65) Prior Publication Data

US 2006/0211577 A1 Sep. 21, 2006

(30) Foreign Application Priority Data

Apr. 8, 2003 (DE) .............................. 103 16 311

(51) Int. Cl.
C07D 239/02 (2006.01)
A01N 43/54 (2006.01)
(52) U.S. Cl. ...................................... 544/311; 504/243
(58) Field of Classification Search ................. 544/239, 544/311; 504/238, 243
See application file for complete search history.

(56) References Cited

U.S. PATENT DOCUMENTS

| | | | |
|---|---|---|---|
| 4,230,874 A | 10/1980 | Pallos et al. |
| 4,293,701 A | 10/1981 | Pallos et al. |
| 4,334,911 A | 6/1982 | Gaughan et al. |
| 4,369,058 A | 1/1983 | Levitt |
| 4,419,523 A | 12/1983 | Pallos et al. |
| 4,746,353 A | 5/1988 | Levitt |
| 4,786,311 A | 11/1988 | Levitt |
| 4,913,726 A | 4/1990 | Levitt |
| 5,017,214 A | 5/1991 | Levitt |
| 5,169,430 A | 12/1992 | Strunk et al. |
| 5,478,798 A | 12/1995 | Mayer et al. |
| 5,635,450 A | 6/1997 | Mayer et al. |
| 5,877,121 A | 3/1999 | Andree et al. |
| 5,928,999 A | 7/1999 | von dem Bussche-Hünnefeld et al. |
| 6,107,252 A | 8/2000 | Andree et al. |
| 6,162,765 A | 12/2000 | Linker et al. |
| 2004/0063580 A1 | 4/2004 | Kuragano et al. |

FOREIGN PATENT DOCUMENTS

| | | |
|---|---|---|
| AU | 199937025 B2 | 12/2001 |
| DE | 4437197 A1 | 4/1995 |
| DE | 4432888 A1 | 3/1996 |
| EP | 0 361 114 A1 | 4/1990 |
| WO | WO 96/07324 A1 | 3/1996 |
| WO | WO 97/00246 A1 | 1/1997 |

OTHER PUBLICATIONS

F. Z. Dorwald "Side Reactions in Organic Synthesis: A Guide to Successful Synthesis Design" 2005 Wiley-VCH Verlag GmbH & Co. KGaA, Weinheim.*
Yasuhiro Yoshioka, Heat-developable photographic films containing specific hydraxine and specific heterocyclic compounds, STA CA Caesar accession No. 1189=JP 2002 36579 (CA-abstract) XP-002289556).
Shreekrishna et al., "Anthranilamides as intermediates for 3-substituted quinazoline-2, 4-diones", (CA-abstract XP-002289557).

* cited by examiner

*Primary Examiner*—Rita J. Desai
*Assistant Examiner*—John Mabry
(74) *Attorney, Agent, or Firm*—Rothwell, Figg, Ernst & Manbeck, P.C.

(57) ABSTRACT

The invention relates to benzenesulphonamide derivatives of formula (I), methods and intermediate products for production thereof and use of said compounds, or means comprising said compounds for the control of undesired plants and for the desiccation/defoliation of plants.

9 Claims, No Drawings

BENZENESULPHONAMIDE DERIVATIVES AS HERBICIDES OR DESICCANT/DEFOLIANT COMPOUNDS

CROSS REFERENCE TO RELATED APPLICATION

This application is a 35 USC §371 National Phase Entry Application from PCT/EP2004/003624, filed Apr. 6, 2004, and designating the United States The present invention relates to benzenesulfonamide derivatives of the formula I

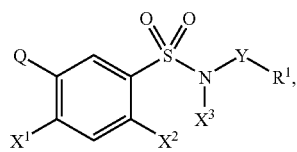

in which the variables are as defined below:

$X^1$ is hydrogen or halogen;

$X^2$ is hydrogen, cyano, CS—$NH_2$, halogen, $C_1$-$C_6$-alkyl or $C_1$-$C_6$-haloalkyl;

$X^3$ is hydrogen, cyano, $C_1$-$C_6$-alkyl, $C_1$-$C_6$-alkoxy-$C_1$-$C_4$-alkyl, $C_3$-$C_7$-cycloalkyl, $C_3$-$C_6$-alkenyl, $C_3$-$C_6$-alkynyl or phenyl-$C_1$-$C_4$-alkyl, where the phenyl radical for its part may be partially or fully halogenated and/or substituted by one to three radicals from the group consisting of $C_1$-$C_6$-alkyl and $C_1$-$C_6$-alkoxy;

Y is a group —C(A)B, $SO_2$ or $SO_2NR^2$;

A is oxygen or sulfur;

B is oxygen, sulfur, $NR^2$ or a bond;

$R^1$ is hydrogen, halogen, hydroxyl, $C_1$-$C_8$-alkyl, $C_3$-$C_7$-cycloalkyl, $C_3$-$C_7$-cyclo-alkyl-$C_1$-$C_4$-alkyl, $C_2$-$C_8$-alkenyl, $C_5$-$C_7$-cycloalkenyl, $C_3$-$C_8$-alkynyl, $C_1$-$C_8$-alkoxy, $C_3$-$C_7$-cycloalkyloxy, $C_2$-$C_8$-alkenyloxy, $C_3$-$C_8$-alkynyloxy, aryl, aryloxy, aryl-$C_1$-$C_4$-alkyl;

where the 13 last mentioned radicals for their part may be partially or fully halogenated and/or may be substituted by one to three substituents from the group consisting of cyano, $NO_2$, hydroxyl, $C_1$-$C_6$-alkyl, $C_1$-$C_6$-haloalkyl, $C_3$-$C_7$-cycloalkyl, $C_1$-$C_6$-alkoxy, $C_1$-$C_6$-haloalkoxy, $C_3$-$C_7$-cycloalkyloxy, $C_2$-$C_6$-alkenyloxy, $C_3$-$C_6$-alkynyloxy, $C_1$-$C_6$-alkylthio, $C_1$-$C_6$-haloalkylthio, amino, $C_1$-$C_6$-alkylamino, di($C_1$-$C_6$-alkyl)amino, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxysulfonyl, formyl, $C_1$-$C_6$-alkylcarbonyl, $C_1$-$C_6$-haloalkylcarbonyl, $C_2$-$C_6$-alkenylcarbonyl, $C_3$-$C_6$-alkynylcarbonyl, carboxy, $C_1$-$C_6$-alkoxycarbonyl, $C_1$-$C_6$-haloalkoxycarbonyl, $C_2$-$C_6$-alkenyloxycarbonyl, $C_3$-$C_6$-alkynyloxycarbonyl, mercaptocarbonyl, $C_1$-$C_6$-alkylthiocarbonyl, $C_1$-$C_6$-haloalkylthiocarbonyl, $C_2$-$C_6$-alkenylthiocarbonyl, $C_3$-$C_6$-alkynylthiocarbonyl, aminocarbonyl, $C_1$-$C_6$-alkylaminocarbonyl, di($C_1$-$C_6$-alkylamino)carbonyl, $C_1$-$C_6$-haloalkylaminocarbonyl, di($C_1$-$C_6$-haloalkylamino)carbonyl, $C_2$-$C_6$-alkenyl-aminocarbonyl, di($C_2$-$C_6$-alkenylamino)carbonyl, $C_3$-$C_6$-alkynylamino-carbonyl, di($C_3$-$C_6$-alkynylamino)carbonyl, phenyl, phenoxy, phenyl-$C_1$-$C_4$-alkyl and phenyl-$C_1$-$C_4$-alkoxy;

four- to six-membered heterocyclyl which may be partially or fully halogenated and/or substituted by one to three radicals from the group consisting of $C_1$-$C_6$-alkyl and $C_1$-$C_6$-alkoxy; or four- to six-membered heterocyclyl-$C_1$-$C_4$-alkyl which may be partially or fully halogenated and/or substituted by one to three radicals from the group consisting of $C_1$-$C_6$-alkyl and $C_1$-$C_6$-alkoxy; or five- or six-membered heteroaryl having one to four nitrogen atoms or having one to three nitrogen atoms and one oxygen or one sulfur atom or having one oxygen or sulfur atom, which radical may be partially or fully halogenated and/or substituted by one to three radicals from the group consisting of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino and di($C_1$-$C_6$-alkyl)amino; or five- or six-membered heteroaryl-$C_1$-$C_4$-alkyl having one to four nitrogen atoms or having one to three nitrogen atoms and one oxygen or one sulfur atom or having one oxygen or sulfur atom, which radical may be partially or fully halogenated and/or substituted by one to three radicals from the group consisting of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino and di($C_1$-$C_6$-alkyl)amino;

$R^2$ is hydrogen, $C_1$-$C_8$-alkyl, $C_2$-$C_8$-alkenyl, $C_3$-$C_8$-alkynyl, $C_3$-$C_7$-cycloalkyl, where the four last mentioned radicals may be partially or fully halogenated; or $R^1$ and $R^2$ together with the nitrogen atom to which they are attached form a three- to seven-membered heterocycle which for its part may be partially or fully halogenated and/or substituted by one to three radicals from the group consisting of $C_1$-$C_6$-alkyl, $C_1$-$C_6$-haloalkyl and $C_1$-$C_6$-alkoxy;

Q is a radical from the group consisting of $Q^1$ to $Q^{39}$

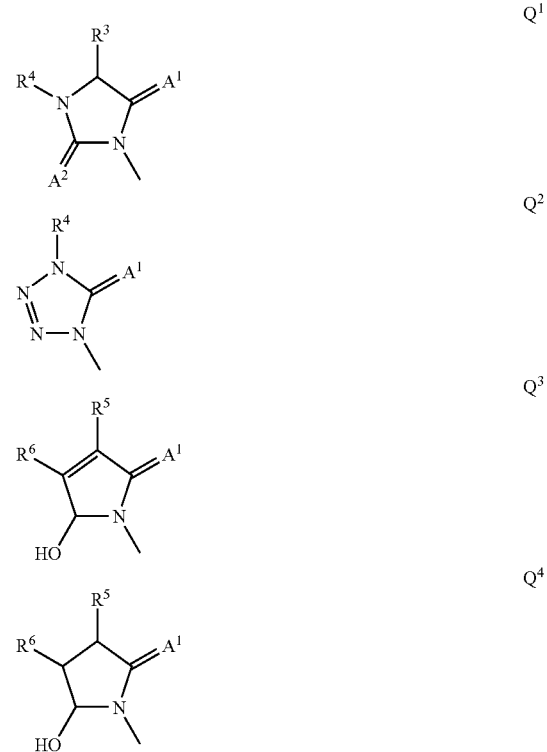

-continued
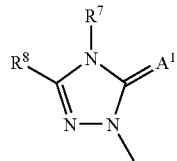
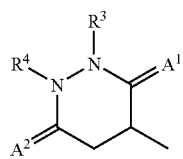
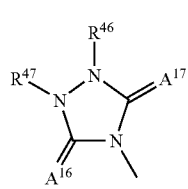
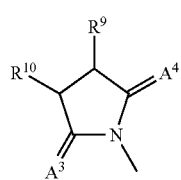
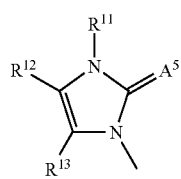
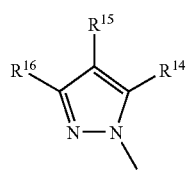
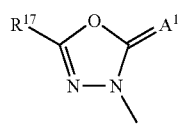
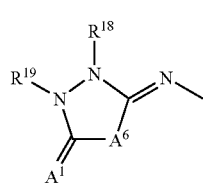
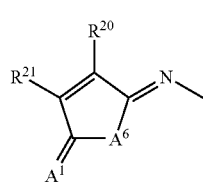
-continued
Q⁵
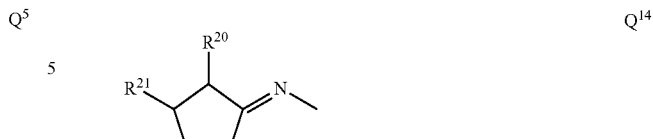
Q⁶
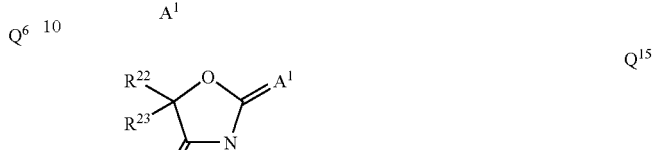
Q⁷
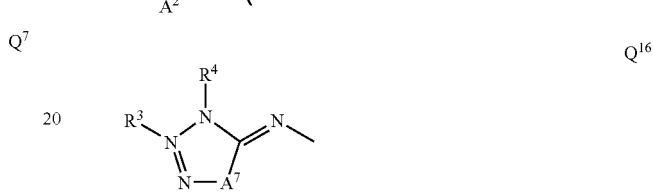
Q⁸
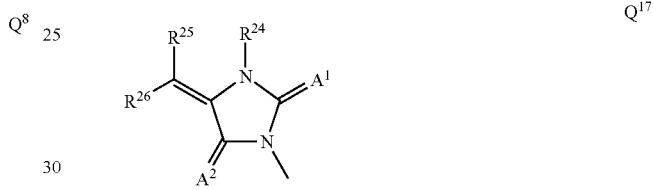
Q⁹
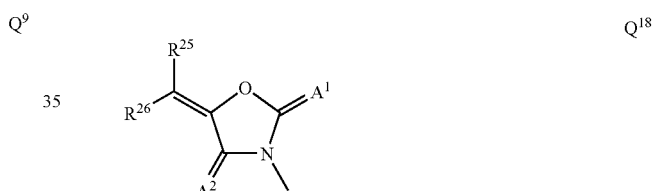
Q¹⁰
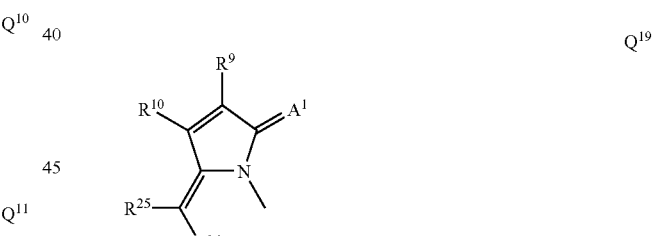
Q¹¹
Q¹²
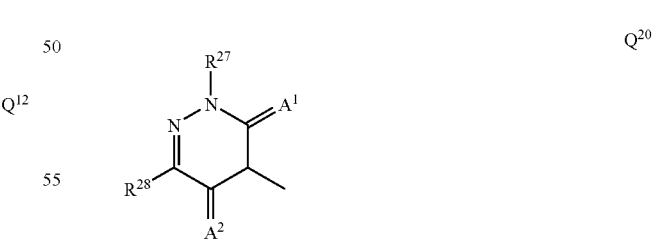
Q¹³
Q¹⁴
Q¹⁵
Q¹⁶
Q¹⁷
Q¹⁸
Q¹⁹
Q²⁰
Q²¹
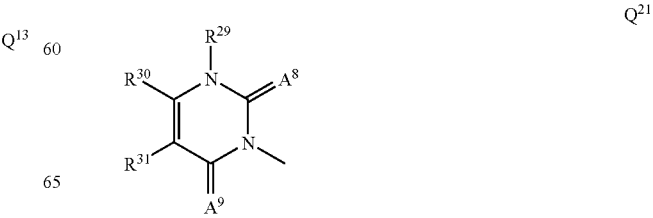

-continued
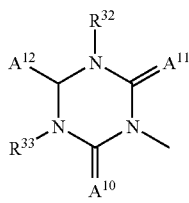
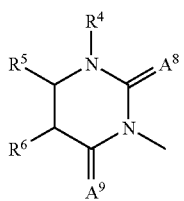
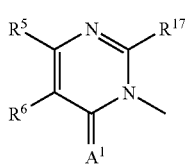
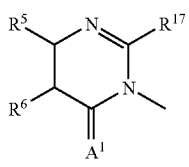
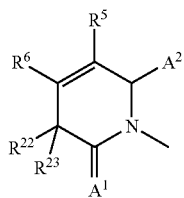
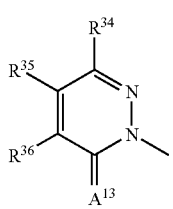
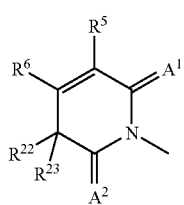
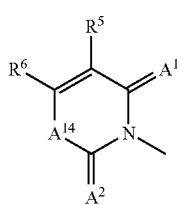
-continued
$Q^{22}$
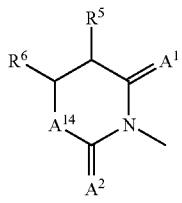
$Q^{23}$
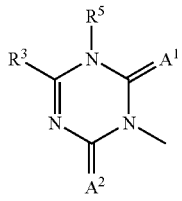
$Q^{24}$
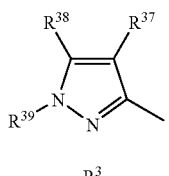
$Q^{25}$
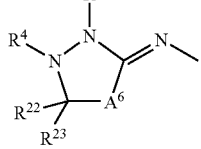
$Q^{26}$
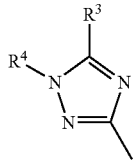
$Q^{27}$
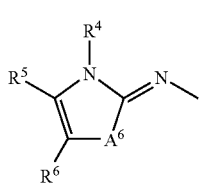
$Q^{28}$
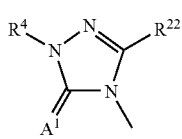
$Q^{29}$
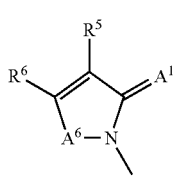
$Q^{30}$
$Q^{31}$
$Q^{32}$
$Q^{33}$
$Q^{34}$
$Q^{35}$
$Q^{36}$
$Q^{37}$
$Q^{38}$
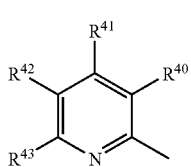

-continued

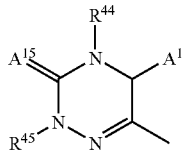

Q³⁹

A¹ to A¹⁷ are oxygen or sulfur;

R³, R⁴, R⁷, R⁸, R¹¹, R¹², R¹⁸, R¹⁹, R²⁷, R²⁹, R³², R³³, R³⁸, R³⁹, R⁴⁴, R⁴⁵, R⁴⁶ and R⁴⁷ are hydrogen, cyano, hydroxyl, $C_1$-$C_6$-alkyl, $C_1$-$C_6$-cyanoalkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkylsulfinyl, $C_1$-$C_6$-alkylsulfonyl, phenyl-$C_1$-$C_6$-alkyl, amino, $C_1$-$C_6$-alkylamino or di($C_1$-$C_6$-alkyl)amino; or R³ and R⁴, R¹¹ and R¹², R¹⁸ and R¹⁹, or R⁴⁶ and R⁴⁷ together with the atoms to which they are attached form a three- to seven-membered heterocycle which for its part may be partially or fully halogenated and/or substituted by one to three radicals from the group consisting of $C_1$-$C_6$-alkyl and $C_1$-$C_6$-alkoxy;

R⁵, R⁶, R⁹, R¹⁰, R¹⁵, R¹⁶, R²⁰, R²¹, R³⁰, R³¹, R³⁵, R³⁶, R⁴¹, R⁴² and R⁴³ are hydrogen, hydroxyl, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkylthio, $C_1$-$C_6$-alkylsulfinyl, $C_1$-$C_6$-alkylsulfonyl, $C_1$-$C_6$-alkoxysulfonyl, $C_1$-$C_6$-alkylsulfonyloxy, amino, $C_1$-$C_6$-alkylamino or di($C_1$-$C_6$-alkyl)amino; or R⁵ and R⁶, R⁹ and R¹⁰, R¹⁵ and R¹⁶, R²⁰ and R²¹, or R³⁰ and R³¹ together with the atoms to which they are attached form a three- to seven-membered heterocycle which for its part may be partially or fully halogenated and/or substituted by one to three radicals from the group consisting of $C_1$-$C_6$-alkyl and $C_1$-$C_6$-alkoxy;

R¹³, R¹⁴, R²², R²³, R²⁵ and R²⁶ are hydrogen, halogen or $C_1$-$C_6$-alkyl;

R¹⁷, R²⁸, R³⁴, R³⁷ and R⁴⁰ are hydrogen, halogen, hydroxyl, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkenyloxy, $C_3$-$C_6$-alkynyl or $C_3$-$C_6$-alkynyloxy;

R²⁴ is hydrogen, $C_1$-$C_6$-alkyl, $C_1$-$C_6$-haloalkyl, $C_2$-$C_6$-alkenyl, $C_3$-$C_6$-alkynyl, $C_1$-$C_6$-haloalkoxy, amino, $C_1$-$C_6$-alkylamino or di($C_1$-$C_6$-alkyl)amino;

and their agriculturally useful salts.

Moreover, the invention relates to processes and intermediates for preparing compounds of formula I, to compositions comprising them and to the use of these derivatives or of the compositions comprising them for controlling unwanted plants.

Furthermore, the invention relates to the use of the compounds of the formula I or of compositions comprising them for the desiccation and/or defoliation of plants.

Further, the invention relates to the preparation of herbicidal compositions and compositions for the desiccation/defoliation of plants using the compounds I, and to methods for controlling unwanted vegetation or for the desiccation/defoliation of plants using the compounds I.

Substituted phenyluracils are disclosed in the literature, for example in WO 96/07323, WO 96/08151, WO 97/42176 and DE 44 37 197. Phenylpyrazoles are described in WO 95/32188. Bicyclic triazolones are described in WO 02/38562. Furthermore, phenyl-substituted pyrimidin(ethi)ones (WO 96/07647), phenylpyridazones (WO 99/52878) and triazole derivatives (WO 96/18618) are known from the literature. WO 93/03019 discloses phenyl-substituted sulfonamides.

However, the herbicidal or desiccant/defoliant properties of the prior-art compounds and/or their compatibilities with crop plants are not always entirely satisfactory. Accordingly, it was an object of the present invention to provide novel, in particular herbicidally active, compounds having improved properties.

The object also extends to providing novel compounds with desiccant/defoliant action.

We have found that this object is achieved by the benzenesulfonamide derivatives of the formula I and their herbicidal action.

Furthermore, we have found herbicidal compositions which comprise the compounds I and have very good herbicidal action. Moreover, we have found processes for preparing these compositions and methods for controlling unwanted vegetation using the compounds I.

Furthermore, it has been found that the compounds I are also suitable for desiccating and defoliating plant parts, suitable plants being crop plants, such as cotton, potatoes, oilseed rape, sunflowers, soybeans or broad beans, in particular cotton. In this respect, the invention provides compositions for the desiccation and/or defoliation of plants, processes for preparing these compositions and methods for the desiccation and/or defoliation of plants using the compounds I.

Depending on the substitution pattern, the compounds of the formula I may comprise one or more centers of chirality, in which case they are present as enantiomers or mixtures of diastereomers. The invention provides both the pure enantiomers or diastereomers and their mixtures.

The compounds of the formula I can also be present in the form of their agriculturally useful salts, the type of salt generally being immaterial. Suitable salts are, in general, the salts of those cations or the acid addition salts of those acids whose cations and anions, respectively, have no adverse effect on the herbicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl-ammonium, di-(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate and the anions of $C_1$-$C_4$-alkanoic acids, preferably formate, acetate, propionate and butyrate.

The organic moieties mentioned for the substituents $X^2$, $X^3$, $R^1$-$R^{47}$ or as radicals on phenyl, heterocyclyl or heteroaryl radicals are collective terms for individual enumerations of the individual group members. All hydrocarbon chains, i.e. all alkyl, alkylene, haloalkyl, cyanoalkyl, phenylalkyl, alkenyl, haloalkenyl, alkynyl, alkoxy, alkylenoxy, haloalkoxy, alkylamino, dialkylamino and alkoxyalkyl moieties can be straight-chain or branched. Unless indicated otherwise, halogenated substituents preferably carry one to five identical or different halogen atoms. The term "halogen" denotes in each case fluorine, chlorine, bromine or iodine.

Examples of Other Meanings are:

- $C_1$-$C_4$-alkyl and the alkyl moieties of $C_1$-$C_6$-alkoxycarbonyl-$C_1$-$C_4$-alkyl, $C_2$-$C_6$-alkynyloxycarbonyl-$C_1$-$C_4$-alkyl, aryl-$C_1$-$C_4$-alkyl, cycloalkyl-$C_1$-$C_4$-alkyl, heterocyclyl-$C_1$-$C_4$-alkyl and heteroaryl-$C_1$-$C_4$-alkyl: methyl, ethyl, n-propyl, 1-methylethyl, n-butyl, 1-methylpropyl, 2-methylpropyl and 1,1-dimethylethyl;

- $C_1$-$C_6$-alkyl and the $C_1$-$C_6$-alkyl moieties of $C_1$-$C_6$-cyanoalkyl, $C_1$-$C_6$-alkylthio, $C_1$-$C_6$-alkylamino, di($C_1$-$C_6$-alkyl)amino, $C_1$-$C_6$-alkylsulfinyl, $C_1$-$C_6$-alkylsulfonyl, $C_1$-$C_6$-alkylcarbonyl, $C_1$-$C_6$-alkylthiocarbonyl, $C_1$-$C_6$-alkylaminocarbonyl, di($C_1$-$C_6$-alkyl)aminocarbonyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

- $C_1$-$C_8$-alkyl: $C_1$-$C_6$-alkyl as mentioned above, and also, for example, heptyl, 2-methylhexyl, 3-methylhexyl, 2,2-dimethylpentyl, 2,3-dimethylpentyl, 2,4-dimethylpentyl, 3,3-dimethylpentyl, 2,2-dimethyl-3-methylbutyl, octyl, 2-methylheptyl, 3-methylheptyl, 4-methylheptyl, 2,2-dimethylhexyl, 2,3-dimethylhexyl, 2,4-dimethylhexyl, 3,3-dimethylhexyl, 2,2,3-trimethylpentyl, 2,3,3-trimethylpentyl, 2,3,4-trimethylpentyl and 2,2,3,3-tetramethylbutyl;

- $C_3$-$C_7$-cycloalkyl and the $C_3$-$C_7$-cycloalkyl moieties of $C_3$-$C_7$-cycloalkyl-$C_1$-$C_4$-alkyl and $C_3$-$C_7$-cycloalkyloxy: a monocyclic saturated hydrocarbon having 3 to 7 ring members, such as cyclopropyl, cyclobutyl, cyclopentyl, cyclohexyl and cycloheptyl;

- $C_5$-$C_7$-cycloalkenyl: a monocyclic unsaturated hydrocarbon having 5 to 7 ring members, for example 1-cyclopentenyl, 2-cyclopentenyl, 3-cyclopentenyl, 2,4-cyclopentadienyl, 1-cyclohexenyl, 2-cyclohexenyl, 3-cyclohexenyl, 1,3-cyclohexadienyl, 2,5-cyclohexadienyl, 1-cycloheptenyl, 2-cycloheptenyl, 3-cycloheptenyl, 4-cycloheptenyl, 2,6-cycloheptadienyl, 3,5-cycloheptadienyl;

- four- to six-membered heterocyclyl: a monocyclic saturated or partially unsaturated hydrocarbon having four to six ring members as mentioned above which, in addition to carbon atoms, may comprise one to four nitrogen atoms, one or two oxygen atoms, one sulfur atom, one to three nitrogen atoms and one oxygen or one sulfur atom or one oxygen and one sulfur atom and which may be attached via a carbon atom or a nitrogen atom, for example 2-oxetanyl, 3-oxetanyl, 3-thiethanyl, 1-azetidinyl, 2-azetidinyl, 1-azetinyl, 2-azetinyl;

for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 1,2,3,4-tetrazolidin-5-yl;

- for example 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,3,4-tetrazolidin-5-yl;

- for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazolyl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazolyl, 2,3-dihydrothiazol-5-yl, 3,4-dihydrothiazol-3-yl, 3,4-dihydrothiazolyl, 3,4-dihydrothiazol-5-yl, 3,4-dihydrothiazol-2-yl, 3,4-dihydrothiazol-3-yl, 3,4-dihydrothiazolyl;

- for example 4,5-dihydropyrrol-1-yl, 2,5-dihydropyrrol-1-yl, 4,5-dihydroisoxazol-2-yl, 2,3-dihydroisoxazol-1-yl, 4,5-dihydroisothiazol-1-yl, 2,3-dihydroisothiazol-1-yl, 2,3-dihydropyrazol-1-yl, 4,5-dihydropyrazol-1-yl, 3,4-dihydropyrazol-1-yl, 2,3-dihydroimidazol-1-yl, 4,5-dihydroimidazol-1-yl, 2,5-dihydroimidazol-1-yl, 2,3-dihydrooxazol-2-yl, 3,4-dihydrooxazol-2-yl, 2,3-dihydrothiazol-2-yl, 3,4-dihydrothiazol-2-yl;

- for example 2-piperidinyl, 3-piperidinyl, 4-piperidinyl, 1,3-dioxan-5-yl, 1,3-dithian-5-yl, 2-tetrahydropyranyl, 4-tetrahydropyranyl, 2-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4- hexahydrotriazin-3-yl, tetrahydro-1,3-oxazin-2-yl, tetrahydro-1,3-oxazin-6-yl, 2-morpholinyl, 3-morpholinyl;

for example 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl;

for example 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

three- to seven-membered heterocyclyl: four- to six-membered heterocyclyl as mentioned above, and also for example 2-oxiranyl, 1-aziridinyl, 2-aziridinyl, 2-thiiranyl;

for example azepan-2-yl, azepan-3-yl, azepan-4-yl, oxepan-2-yl, oxepan-3-yl, oxepan-4-yl, thiepan-2-yl, thiepan-3-yl, thiepan-4-yl, 1,2-diazepan-3-yl, 1,2-diazepan-4-yl, 1,2-diazepan-5-yl;

for example azepan-1-yl, 1,2-diazepan-1-yl, 1,4-oxazepan-4-yl, 1,4-thiazepan-4-yl;

for example 2,3,6,7-tetrahydro-1H-azepin-2-yl, 2,3,6,7-tetrahydro-1H-azepin-3-yl, 2,3,6,7-tetrahydro-1H-azepin-4-yl, 2,3,4,5-tetrahydro-1H-azepin-2-yl, 2,3,4,5-tetrahydro-1H-azepin-3-yl, 2,3,4,5-tetrahydro-1H-azepin-4-yl, 1H-azepin-2-yl, 1H-azepin-3-yl, 1H-azepin-4-yl, oxepin-2-yl, oxepin-3-yl, oxepin-4-yl, thiepin-2-yl, thiepin-3-yl, thiepin-4-yl, 1,4-oxazepin-2-yl, 1,4-oxazepin-3-yl, 1,4-oxazepin-5-yl, 1,4-oxazepin-6-yl, 1,4-oxazepin-7-yl, 1,4-thiazepin-2-yl, 1,4-thiazepin-3-yl, 1,4-thiazepin-5-yl, 1,4-thiazepin-6-yl, 1,4-thiazepin-7-yl, 4,5,6,7-tetrahydro-1H-[1,3]-diazepin-2-yl, 4,5,6,7-tetrahydro-1H-[1,3]-diazepin-4-yl, 4,5,6,7-tetrahydro-1H-[1,3]-diazepin-5-yl, 4,5,6,7-tetrahydro-1H-[1,3]-diazepin-6-yl, 4,5,6,7-tetrahydro-1H-[1,3]-diazepin-7-yl, 2,3,4,5-tetrahydro-1H-[1,4]-diazepin-2-yl, 2,3,4,5-tetrahydro-1H-[1,4]-diazepin-3-yl, 2,3,4,5-tetrahydro-1H-[1,4]-diazepin-5-yl, 2,3,4,5-tetrahydro-1H-[1,4]-diazepin-6-yl, 2,3,4,5-tetrahydro-1H-[1,4]-diazepin-7-yl, 2,3-dihydro-1H-[1,2]diazepin-3-yl, 2,3-dihydro-1H-[1,2]diazepin-4-yl, 2,3-dihydro-1H-[1,2]diazepin-5-yl, 2,3-dihydro-1H-[1,2]diazepin-6-yl, 2,3-dihydro-1H-[1,2]diazepin-7-yl, 4,7-dihydro-[1,4]-oxazepin-2-yl, 4,7-dihydro-[1,4]-oxazepin-3-yl, 4,7-dihydro-[1,4]-oxazepin-5-yl, 4,7-dihydro-[1,4]-oxazepin-6-yl, 4,7-dihydro-[1,4]-oxazepin-7-yl, 2,3-dihydro-[1,3]-thiazepin-2-yl, 2,3-dihydro-[1,3]-thiazepin-4-yl, 2,3-dihydro-[1,3]-thiazepin-5-yl, 2,3-dihydro-[1,3]-thiazepin-6-yl, 2,3-dihydro-[1,3]-thiazepin-7-yl;

for example azepin-1-yl, 2,3,6,7-tetrahydroazepin-1-yl, 2,3,4,5-tetrahydroazepin-1-yl, 4,5,6,7-tetrahydro-[1,3]-diazepin-1-yl, 2,3,4,5-tetrahydro-[1,4]-diazepin-1-yl, 2,3-dihydro-[1,2]diazepin-1-yl, 4,7-dihydro-[1,4]-oxazepin-4-yl, 2,3-dihydro-[1,3]-thiazepin-3-yl;

$C_2$-$C_4$-alkenyl and the alkenyl moieties of $C_1$-$C_6$-alkoxycarbonyl-$C_2$-$C_4$-alkenyl: ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and the $C_2$-$C_6$-alkenyl moieties of $C_2$-$C_6$-alkenyloxy, $C_2$-$C_6$-alkenylcarbonyl, $C_2$-$C_6$-alkenyloxycarbonyl, $C_2$-$C_6$-alkenyloxycarbonyl-$C_1$-$C_4$-alkyl, $C_2$-$C_6$-alkenylthiocarbonyl, $C_2$-$C_6$-alkenylaminocarbonyl, di($C_2$-$C_6$-alkenyl)aminocarbonyl: $C_3$-$C_6$-alkenyl as mentioned above, and also ethenyl;

$C_2$-$C_8$-alkenyl and the $C_2$-$C_8$-alkenyl moieties of $C_2$-$C_8$-alkenyloxy: $C_2$-$C_6$-alkenyl as mentioned above, and also, for example, 1-heptenyl, 2-heptenyl, 3-heptenyl, 2-methyl-1-hexenyl, 2-methyl-2-hexenyl, 2-methyl-3-hexenyl, 2-methyl-4-hexenyl, 2-methyl-5-hexenyl, 3-methyl-1-hexenyl, 3-methyl-2-hexenyl, 3-methyl-3-hexenyl, 3-methyl-4-hexenyl, 3-methyl-5-hexenyl, 2,2-dimethyl-3-pentenyl, 2,2-dimethyl-4-pentenyl, 2,3-dimethyl-1-pentenyl, 2,3-dimethyl-2-pentenyl, 2,3-dimethyl-3-pentenyl, 2,3-dimethyl-4-pentenyl, 2,4-dimethyl-1-pentenyl, 2,4-dimethyl-2-pentenyl, 3,3-dimethyl-1-pentenyl, 2,2-dimethyl-3-methyl-3-butentyl, 1-octenyl, 2-octenyl, 3-octenyl, 4-octenyl, 2-methyl-1-heptenyl, 2-methyl-2-heptenyl, 2-methyl-3-heptenyl, 2-methyl-4-heptenyl, 2-methyl-5-heptenyl, 2-methyl-6-heptenyl, 3-methyl-1-heptenyl, 3-methyl-2-heptenyl, 3-methyl-3-heptenyl, 3-methyl-4-heptenyl, 3-methyl-5-heptenyl, 3-methyl-6-heptenyl, 4-methyl-1-heptenyl, 4-methyl-2-heptenyl, 4-methyl-3-heptenyl, 2,2-dimethyl-3-hexenyl, 2,2-dimethyl-4-hexenyl, 2,2-dimethyl-5-hexenyl, 2,3-dimethyl-1-hexenyl, 2,3-dimethyl-2-hexenyl, 2,3-dimethyl-3-hexenyl, 2,3-dimethyl-4-hexenyl, 2,3-dimethyl-5-hexenyl, 2,4-dimethyl-1-hexenyl, 2,4-dimethyl-2-hexenyl, 2,4-dimethyl-3-hexenyl, 2,4-dimethyl-4-hexenyl, 2,4-dimethyl-5-hexenyl, 3,3-dimethyl-1-hexenyl, 3,3-dimethyl-4-hexenyl, 3,3-dimethyl-5-hexenyl, 2,2,3-trimethyl-3-pentenyl, 2,2,3-trimethyl-4-pentenyl, 2,3,3-trimethyl-1-pentenyl, 2,3,3-trimethyl-4-pentenyl, 2,3,4-trimethyl-1-pentenyl and 2,3,4-trimethyl-2-pentenyl;

$C_3$-$C_6$-alkynyl and the $C_3$-$C_6$-alkynyl moieties of $C_3$-$C_6$-alkynyloxy, $C_3$-$C_6$-alkynyl-carbonyl, $C_3$-$C_6$-alkynyloxycarbonyl, $C_3$-$C_6$-alkynylthiocarbonyl, $C_3$-$C_6$-alkynyl-aminocarbonyl, di($C_3$-$C_6$-alkynyl)aminocarbonyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_8$-alkynyl and the $C_3$-$C_8$-alkynyl moieties of $C_3$-$C_8$-alkynyloxy: $C_3$-$C_6$-alkynyl as mentioned above, and also, for example, 1-heptynyl, 2-heptynyl, 3-heptynyl, 2-methyl-3-hexynyl, 2-methyl-4-hexynyl, 2-methyl-5-hexynyl, 3-methyl-1-hexynyl, 3-methyl-4-hexynyl, 3-methyl-5-hexynyl, 2,2-dimethyl-3-pentynyl, 2,2-dimethyl-4-pentynyl, 2,3-dimethyl-4-pentynyl, 3,3-dimethyl-1-pentynyl, 1-octynyl, 2-octynyl, 3-octynyl, 4-octynyl, 2-methyl-3-heptynyl, 2-methyl-4-heptynyl, 2-methyl-5-heptynyl, 2-methyl-6-heptynyl, 3-methyl-1-heptynyl, 3-methyl-4-heptynyl, 3-methyl-5-heptynyl, 3-methyl-6-heptynyl, 4-methyl-1-heptynyl, 4-methyl-2-heptynyl, 2,2-dimethyl-3-hexynyl, 2,2-dimethyl-4-hexynyl, 2,2-dimethyl-5-hexynyl, 2,3-dimethyl-4-hexynyl, 2,3-dimethyl-5-hexynyl, 2,4-dimethyl-5-hexynyl, 3,3-dimethyl-1-hexynyl, 3,3-dimethyl-4-hexynyl, 3,3-dimethyl-5-hexynyl, 2,2,3-trimethyl-3-pentynyl, 2,2,3-trimethyl-4-pentynyl and 2,3,3-trimethyl-4-pentynyl;

$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl and the $C_1$-$C_6$-haloalkyl moieties of $C_1$-$C_6$-haloalkylthio, $C_1$-$C_6$-haloalkylsulfinyl, $C_1$-$C_6$-haloalkylsulfonyl, $C_1$-$C_6$-haloalkylcarbonyl, $C_1$-$C_6$-haloalkylthiocarbonyl, $C_1$-$C_6$-haloalkylaminocarbonyl, di($C_1$-$C_6$-haloalkyl)aminocarbonyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$-$C_8$-haloalkyl: $C_1$-$C_6$-haloalkyl as mentioned above, and also, for example, 7-fluoroheptyl, 7-chloroheptyl, 7-bromoheptyl, 7-iodoheptyl, perfluoroheptyl, 8-fluorooctyl, 8-chlorooctyl, 8-bromooctyl, 8-iodooctyl and perfluorooctyl;

$C_2$-$C_6$-haloalkenyl: a $C_2$-$C_6$-alkenyl radical as mentioned above which is partially or fully substituted by fluorine, chlorine, bromine and/or iodine, for example 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromovinyl, 2-bromoallyl, 3-bromoallyl, 2,3-dibromoallyl, 3,3-dibromoallyl, 2,3,3-tribromoallyl and 2,3-dibromobut-2-enyl;

$C_2$-$C_8$-haloalkenyl: a $C_2$-$C_6$-haloalkenyl radical as mentioned above, and also, for example, 2-chloro-1-heptenyl, 3-chloro-1-heptenyl, 2,3-dichloro-1-heptenyl, 3,3-dichloro-1-heptenyl, 2,3,3-trichloro-1-heptenyl, 2-bromo-1-heptenyl, 3-bromo-1-heptenyl, 2,3-dibromo-1-heptenyl, 3,3-dibromo-1-heptenyl, 2,3,3-tribromo-1-heptenyl, 2-chloro-1-octenyl, 3-chloro-1-octenyl, 2,3-dichloro-1-octenyl, 3,3-dichloro-1-octenyl, 2,3,3-trichloro-1-octenyl, 2-bromo-1-octenyl, 3-bromo-1-octenyl, 2,3-dibromo-1-octenyl, 3,3-dibromo-1-octenyl and 2,3,3-tribromo-1-octenyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl and 6-iodohex-5-yn-1-yl;

$C_1$-$C_4$-alkoxy and the $C_1$-$C_4$-alkoxy moieties of $C_1$-$C_4$-alkoxy-$C_1$-$C_4$-alkyl and phenyl-$C_1$-$C_4$-alkoxy: for example methoxy, ethoxy, propoxy, 1-methylethoxy, butoxy, 1-methylpropoxy, 2-methylpropoxy and 1,1-dimethylethoxy;

$C_1$-$C_6$-alkoxy and the $C_1$-$C_6$-alkoxy moieties of $C_1$-$C_6$-alkoxy-$C_1$-$C_4$-alkyl, $C_1$-$C_6$-alkoxycarbonyl, $C_1$-$C_6$-alkoxycarbonyl-$C_1$-$C_4$-alkyl, $C_1$-$C_6$-alkoxycarbonyl-$C_2$-$C_4$-alkenyl, $C_1$-$C_6$-alkoxysulfonyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_8$-alkoxy: $C_1$-$C_6$-alkoxy as mentioned above, and also, for example, heptoxy, 2-methylhexoxy, 3-methylhexoxy, 2,2-dimethylpentoxy, 2,3-dimethylpentoxy, 2,4-dimethylpentoxy, 3,3-dimethylpentoxy, 2,2-dimethyl-3-methylbutoxy, octoxy, 2-methylheptoxy, 3-methylheptoxy, 4-methylheptoxy, 2,2-dimethylhexoxy, 2,3-dimethylhexoxy, 2,4-dimethylhexoxy, 3,3-dimethylhexoxy, 2,2,3-trimethylpentoxy, 2,3,3-trimethylpentoxy, 2,3,4-trimethylpentoxy and 2,2,3,3-tetramethylbutoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2- bromoethoxy, 4-fluorobutoxy, 4-chlorobutoxy, 4-bromobutoxy and nonafluorobutoxy;

$C_1$-$C_6$-haloalkoxy and the $C_1$-$C_6$-haloalkoxy moieties of $C_1$-$C_6$-haloalkoxycarbonyl: $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkoxy-$C_1$-$C_4$-alkyl and the alkyl radicals of $C_1$-$C_6$-alkylthio-$C_1$-$C_4$-alkyl: a $C_1$-$C_4$-alkyl which is substituted by $C_1$-$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy) propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)-butyl, 2-(butoxy)butyl, 2-(1-methylpropoxy)butyl, 2-(2-methylpropoxy)butyl, 2-(1,1-dimethylethoxy)butyl, 3-(methoxy) butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl and 4-(1,1-dimethylethoxy)butyl;

$C_1$-$C_6$-alkoxycarbonyl-$C_1$-$C_4$-alkyl: $C_1$-$C_4$-alkyl which is substituted by $C_1$-$C_6$-alkoxycarbonyl as mentioned above, i.e., for example, methoxycarbonylmethyl, ethoxycarbonylmethyl, propoxycarbonylmethyl, (1-methylethoxycarbonyl)methyl, butoxycarbonylmethyl, (1-methylpropoxycarbonyl)methyl, (2-methylpropoxycarbonyl)methyl, (1,1-dimethylethoxycarbonyl)methyl, 2-(methoxycarbonyl)ethyl, 2-(ethoxycarbonyl)ethyl, 2-(propoxycarbonyl)ethyl, 2-(1-methylethoxycarbonyl)ethyl, 2-(butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(propoxycarbonyl)propyl, 2-(1-methylethoxycarbonyl)propyl, 2-(butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(propoxycarbonyl)propyl, 3-(1-methylethoxycarbonyl)propyl, 3-(butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(propoxycarbonyl)butyl, 2-(1-methylethoxycarbonyl)butyl, 2-(butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(propoxycarbonyl)butyl, 3-(1-methylethoxycarbonyl)butyl, 3-(butoxycarbonyl) butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(propoxycarbonyl)butyl, 4-(1-methylethoxycarbonyl)butyl, 4-(butoxycarbonyl) butyl, 4-(1-methylpropoxy)butoxy, 4-(2-methylpropoxy)butoxy and 4-(1,1-dimethylethoxycarbonyl)butyl;

$C_1$-$C_4$-alkylthio: for example methylthio, ethylthio, n-propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_8$-alkylthio: $C_1$-$C_6$-alkylthio as mentioned above and the alkylthio moieties of $C_1$-$C_8$-alkylthio-$C_1$-$C_8$-alkyl, and also, for example, heptylthio, 2-methylhexylthio, 3-methylhexylthio, 2,2-dimethylpentylthio, 2,3-dimethylpentylthio, 2,4-dimethylpentylthio, 3,3-dimethylpentylthio, 2,2-dimethyl-3-methylbutylthio, octylthio, 2-methylheptylthio, 3-methylheptylthio, 4-methylheptylthio, 2,2-dimethylhexylthio, 2,3-dimethylhexylthio, 2,4-dimethylhexylthio, 3,3-dimethylhexylthio, 2,2,3-trimethylpentylthio, 2,3,3-trimethylpentylthio, 2,3,4-trimethylpentylthio and 2,2,3,3-tetramethylbutylthio;

$C_1$-$C_6$-alkylamino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino and 1-ethyl-2-methylpropylamino;

di($C_1$-$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)-amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2- methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_6$-alkyl)amino and the dialkylamino moieties of di($C_1$-$C_6$-alkyl)amino-$C_1$-$C_6$-alkyl, di($C_1$-$C_6$-alkyl)aminocarbonyl and di($C_1$-$C_6$-alkyl)aminocarbonyl-$C_1$-$C_6$-alkyl: di($C_1$-$C_4$-alkyl)amino as mentioned above, for example, N,N-dipentylamino, N,N-dihexylamino, N-methyl-N-pentylamino, N-ethyl-N-pentylamino, N-methyl-N-hexylamino and N-ethyl-N-hexylamino;

aryl and the aryl moieties of aryloxy and aryl-$C_1$-$C_4$-alkyl: a monocyclic to tricyclic aromatic carbocycle having 6 to 14 ring members, such as, for example, phenyl, naphthyl and anthracenyl;

5- or 6-membered heteroaryl and the 5- or 6-membered heteroaryl moieties of 5- or 6-membered heteroaryl-$C_1$-$C_6$-alkyl: aromatic 5- or 6-membered heterocycles which, in addition to carbon atoms, may comprise one to four nitrogen atoms or one to three nitrogen atoms and one sulfur or oxygen atom or one oxygen or sulfur atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl and tetrazol-2-yl;

2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, 1,2,4-triazin-5-yl, 1,2,4-triazin-6-yl and 1,2,4,5-tetrazinyl.

In a particular embodiment, the variables of the compounds of the formula I are as defined below, these definitions being, both on their own and in combination with one another, particular embodiments of the compounds of the formula I:

Preference is given to the benzenesulfonamides of the formula I in which
$X^1$ is hydrogen, fluorine or chlorine;
particularly preferably hydrogen or fluorine;
especially preferably fluorine.

Preference is also given to the benzenesulfonamide derivatives of the formula I in which
$X^2$ is hydrogen, cyano, CS—$NH_2$ or halogen;
particularly preferably hydrogen, cyano or halogen such as fluorine and chlorine;
especially preferably chlorine.

Preference is also given to the benzenesulfonamide derivatives of the formula I in which
$X^1$ is hydrogen, fluorine or chlorine;
particularly preferably hydrogen or fluorine;
especially preferably fluorine; and
$X^2$ is hydrogen, cyano, CS—$NH_2$ or halogen;
particularly preferably hydrogen, cyano, halogen such as fluorine and chlorine;
especially preferably chlorine.

Preference is also given to the benzenesulfonamide derivatives of the formula I in which $X^3$ is hydrogen, cyano, $C_1$-$C_6$-alkyl or phenyl-$C_1$-$C_4$-alkyl;
particularly preferably hydrogen, cyano, $C_1$-$C_4$-alkyl, such as $CH_3$, and $C_2H_5$, or benzyl;
especially preferably hydrogen or cyano;
with extraordinary preference hydrogen.

Preference is also given to the benzenesulfonamide derivatives of the formula I in which
Y is a group C(A)B;
particularly preferably C(A)B, where A is oxygen;
especially preferably C(A)B, where A is oxygen and B is oxygen or sulfur;
with extraordinary preference C(A)B, where A and B are oxygen.

Preference is also given to the benzenesulfonamide derivatives of the formula I in which
Y is a group C(A)B;
particularly preferably C(A)B, where A is oxygen;
especially preferably C(A)B, where A is oxygen and B is $NR^2$.

Preference is also given to the benzenesulfonamide derivatives of the formula I in which
Y is a group C(A)B;
particularly preferably C(A)B, where A is oxygen;
especially preferably C(A)B, where A is oxygen and B is a bond.

Preference is also given to the benzenesulfonamide derivatives of the formula I in which
$R^1$ is hydrogen, hydroxyl, $C_1$-$C_8$-alkyl, $C_1$-$C_8$-haloalkyl, $C_3$-$C_7$-cycloalkyl, $C_3$-$C_7$-cycloalkyl-$C_1$-$C_4$-alkyl, $C_2$-$C_8$-alkenyl, $C_2$-$C_8$-haloalkenyl, $C_3$-$C_8$-alkynyl, $C_1$-$C_8$-alkoxy, $C_1$-$C_6$-alkoxy-$C_1$-$C_4$-alkyl, $C_1$-$C_6$-alkoxycarbonyl-$C_1$-$C_4$-alkyl, $C_1$-$C_6$-alkoxycarbonyl-$C_2$-$C_4$-alkenyl, $C_2$-$C_6$-alkenyloxycarbonyl-$C_1$-$C_4$-alkyl, $C_3$-$C_6$-alkynyloxycarbonyl-$C_1$-$C_4$-alkyl, $C_1$-$C_6$-alkylthio-$C_1$-$C_4$-alkyl, aryl, aryl-$C_1$-$C_4$-alkyl;

four- to six-membered heterocyclyl which may be partially or fully halogenated and/or may carry one to three radicals from the group consisting of $C_1$-$C_4$-alkyl and $C_1$-$C_4$-alkoxy;

four- to six-membered heterocyclyl-$C_1$-$C_4$-alkyl which may be partially or fully halogenated and/or may carry one to three radicals from the group consisting of $C_1$-$C_4$-alkyl and $C_1$-$C_4$-alkoxy;

five- or six-membered heteroaryl having one to four nitrogen atoms or having one to three nitrogen atoms and one oxygen or one sulfur atom or having one oxygen or sulfur atom, which radicals may be partially or fully halogenated and/or may carry one to three radicals from the group consisting of $C_1$-$C_4$-alkyl, $C_1$-$C_4$-haloalkyl, $C_1$-$C_4$-alkoxy, $C_1$-$C_4$-haloalkoxy, amino, $C_1$-$C_4$-alkylamino and di($C_1$-$C_4$-alkyl)amino;

five- or six-membered heteroaryl-$C_1$-$C_4$-alkyl having one to four nitrogen atoms or having one to three nitrogen atoms and one oxygen or one sulfur atom or having one oxygen or sulfur atom, which radicals may be partially or fully halogenated and/or may carry one to three radicals from the group consisting of $C_1$-$C_4$-alkyl and $C_1$-$C_4$-alkoxy;

particularly preferably
hydrogen, hydroxyl, $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl, $C_3$-$C_6$-alkynyl, $C_1$-$C_6$-alkoxy, $C_1$-$C_4$-alkoxy-$C_1$-$C_4$-alkyl, $C_1$-$C_4$-alkoxycarbonyl-$C_1$-$C_4$-alkyl, $C_1$-$C_4$-alkoxycarbonyl-$C_2$-$C_4$-alkenyl, $C_2$-$C_4$-alkenyloxycarbonyl-$C_1$-$C_4$-alkyl, $C_3$-$C_6$-alkynyloxycarbonyl-$C_1$-$C_4$-alkyl, $C_1$-$C_4$-alkylthio-$C_1$-$C_4$-alkyl, phenyl, benzyl;

five- or six-membered heterocyclyl which may be partially or fully halogenated and/or may carry one to three radicals from the group consisting of $C_1$-$C_4$-alkyl and $C_1$-$C_4$-alkoxy;

five- or six-membered heteroaryl having one to four nitrogen atoms or having one to three nitrogen atoms and one oxygen or one sulfur atom or having one oxygen or sulfur atom, which radicals may be partially or fully halogenated and/or may carry one to three radicals from the group consisting of $C_1$-$C_4$-alkyl, $C_1$-$C_4$-haloalkyl, $C_1$-$C_4$-alkoxy, $C_1$-$C_4$-haloalkoxy, amino, $C_1$-$C_4$-alkylamino and di($C_1$-$C_4$-alkyl)amino;

especially preferably $C_1$-$C_4$-alkyl, $C_1$-$C_4$-haloalkyl, $C_5$-$C_6$-cycloalkyl, $C_2$-$C_6$-alkenyl, $C_3$-$C_6$-alkynyl, $C_1$-$C_4$-alkoxy-$C_1$-$C_4$-alkyl, $C_1$-$C_4$-alkylthio-$C_1$-$C_4$-alkyl, phenyl, benzyl;

five- or six-membered heterocyclyl which may be partially or fully halogenated and/or may carry one to three radicals from the group consisting of $C_1$-$C_4$-alkyl and $C_1$-$C_4$-alkoxy;

five- or six-membered heteroaryl having one to four nitrogen atoms or having one to three nitrogen atoms and one oxygen or one sulfur atom or having one oxygen or sulfur atom, where the two last mentioned radicals may be partially or fully halogenated and/or may carry one to three radicals from the group consisting of $C_1$-$C_4$-alkyl and $C_1$-$C_4$-alkoxy;

with extraordinary preference $C_1$-$C_4$-alkyl, such as $C_3$, $C_2H_5$, $CH(CH_3)_2$, —$CH_2$—$CH_2$—$CH_3$, $C_1$-$C_4$-haloalkyl, such as $CF_3$, $C_5$-$C_6$-cycloalkyl, $C_2$-$C_4$-alkenyl, $C_3$-$C_4$-alkynyl, $C_1$-$C_4$-alkoxy-$C_1$-$C_4$-alkyl, $C_1$-$C_4$-alkylthio-$C_1$-$C_4$-alkyl, phenyl, benzyl, five- or six-membered heterocyclyl or five- or six-membered heteroaryl having one to four nitrogen atoms, where the two last mentioned radicals may be partially or fully halogenated and/or may carry one to three radicals from the group consisting of $C_1$-$C_4$-alkyl and $C_1$-$C_4$-alkoxy.

Preference is also given to the benzenesulfonamide derivatives of the formula I in which $R^2$ is hydrogen, $C_1$-$C_8$-alkyl or $C_2$-$C_8$-alkenyl, particularly preferably hydrogen, $C_1$-$C_6$-alkyl or $C_2$-$C_6$-alkenyl, especially preferably hydrogen or $C_1$-$C_4$-alkyl, with extraordinary preference hydrogen, $CH_3$, $C_2H_5$ or $CH(CH_3)_2$, with most extraordinary preference hydrogen or $CH_3$.

Preference is also given to the benzenesulfonamide derivatives of the formula I in which $R^1$ and $R^2$ together with the nitrogen atom to which they are attached form a three- to seven-membered heterocycle which for its part may be partially or fully halogenated and/or may carry one to three radicals from the group consisting of $C_1$-$C_6$-alkyl, $C_1$-$C_6$-haloalkyl and $C_1$-$C_6$-alkoxy;

particularly preferably a three- to seven-membered heterocycle which for its part may be partially or fully halogenated and/or may carry one to three radicals from the group consisting of $C_1$-$C_4$-alkyl and $C_1$-$C_4$-alkoxy;

especially preferably a five- to seven-membered heterocycle which for its part may be partially or fully halogenated and/or may carry one to three radicals from the group consisting of $C_1$-$C_4$-alkyl and $C_1$-$C_4$-alkoxy;

with extraordinary preference a five- or six-membered heterocycle which for its part may be partially or fully halogenated and/or may carry one to three radicals from the group consisting of $C_1$-$C_4$-alkyl and $C_1$-$C_4$-alkoxy;

with most extraordinary preference a heterocycle from the group consisting of pyrrolidin-1-yl, 2,3-dihydropyrrol-1-yl, 2,5-dihydropyrrol-1-yl, piperidin-1-yl, 1,2,3,4-tetrahydropyridin-1-yl, 1,2,3,6-tetrahydropyridin-1-yl, piperazin-1-yl, morpholin-4-yl, which heterocycle may for its part be partially or fully halogenated and/or may carry one to three radicals from the group consisting of $C_1$-$C_4$-alkyl and $C_1$-$C_4$-alkoxy.

Preference is also given to the benzenesulfonamide derivatives of the formula I in which Y is C(A)B, where A and B are oxygen; and $R^1$ has the preferred meanings mentioned above.

Preference is also given to the benzenesulfonamide derivatives of the formula I in which Y is C(A)B, where A is oxygen and B is $NR^2$; and $R^2$ is hydrogen, $C_1$-$C_8$-alkyl or $C_2$-$C_8$-alkenyl, particularly preferably hydrogen, $C_1$-$C_6$-alkyl or $C_2$-$C_6$-alkenyl, especially preferably hydrogen or $C_1$-$C_4$-alkyl, with extraordinary preference hydrogen, $CH_3$, $C_2H_5$ or $CH(CH_3)_2$; with most extraordinary preference hydrogen or $CH_3$;

with particular preference

Y is C(=A)B, where A is oxygen and B is $NR^2$;

$R^2$ is hydrogen, $C_1$-$C_8$-alkyl or $C_2$-$C_8$-alkenyl, particularly preferably hydrogen, $C_1$-$C_6$-alkyl or $C_2$-$C_6$-alkenyl, especially preferably hydrogen or $C_1$-$C_4$-alkyl, with extraordinary preference hydrogen, $CH_3$, $C_2H_5$ or $CH(CH_3)_2$;

with most extraordinary preference hydrogen or $CH_3$; and $R^1$ has the preferred meanings mentioned above.

Preference is also given to the benzenesulfonamide derivatives of the formula I in which Y is C(A)B where A is oxygen and B is $NR^2$; and $R^1$ and $R^2$ together with the nitrogen atom to which they are attached, form a three- to seven-membered heterocycle which for its part may be partially or fully halogenated and/or may carry one to three radicals from the group consisting of $C_1$-$C_6$-alkyl, $C_1$-$C_6$-haloalkyl and $C_1$-$C_6$-alkoxy;

particularly preferably a three- to seven-membered heterocycle which for its part may be partially or fully halogenated and/or may carry one to three radicals from the group consisting of $C_1$-$C_4$-alkyl and $C_1$-$C_4$-alkoxy;

especially preferably a five- to seven-membered heterocycle which for its part may be partially or fully halogenated and/or may carry one to three radicals from the group consisting of $C_1$-$C_4$-alkyl and $C_1$-$C_4$-alkoxy;

with extraordinary preference a five- or six-membered heterocycle which for its part may be partially or fully halogenated and/or may carry one to three radicals from the group consisting of $C_1$-$C_4$-alkyl and $C_1$-$C_4$-alkoxy;

with most extraordinary preference a heterocycle from the group consisting of pyrrolidin-1-yl, 2,3-dihydropyrrol-1-yl, 2,5-dihydropyrrol-1-yl, piperidin-1-yl, 1,2,3,4-tetrahydropyridin-1-yl, 1,2,3,6-tetrahydropy-
ridin-1-yl, piperazin-1-yl, morpholin-4-yl, which for
its part may be partially or fully halogenated and/or
may carry one to three radicals from the group con-
sisting of $C_1$-$C_4$-alkyl and $C_1$-$C_4$-alkoxy.

Preference is also given to the benzenesulfonamide deriva-
tives of the formula I in which
Y is C(A)B, where A is oxygen and B is a bond; and
$R^1$ has the preferred meanings mentioned above.

Preference is also given to the benzenesulfonamide deriva-
tives of the formula I in which
Y is a group $SO_2$;
particularly preferably
Y is $SO_2$; and
$R^1$ has the preferred meanings mentioned above.

Preference is also given to the benzenesulfonamide deriva-
tives of the formula I in which
Y is a group $SO_2NR^2$;
particularly preferably
Y is $SO_2NR^2$; and
$R^2$ is hydrogen, $C_1$-$C_8$-alkyl or $C_2$-$C_8$-alkenyl,
particularly preferably hydrogen, $C_1$-$C_6$-alkyl or $C_2$-$C_6$-alkenyl,
especially preferably hydrogen or $C_1$-$C_4$-alkyl,
with extraordinary preference hydrogen, $CH_3$, $C_2H_5$ or $CH(CH_3)_2$;
with most extraordinary preference hydrogen or $CH_3$;
especially preferably
Y is $SO_2NR^2$;
$R^2$ is hydrogen, $C_1$-$C_8$-alkyl or $C_2$-$C_8$-alkenyl,
particularly preferably hydrogen, $C_1$-$C_6$-alkyl or $C_2$-$C_6$-alkenyl,
especially preferably hydrogen or $C_1$-$C_4$-alkyl,
with extraordinary preference hydrogen, $CH_3$, $C_2H_5$ or $CH(CH_3)_2$;
with most extraordinary preference hydrogen or $CH_3$;
and
$R^1$ has the preferred meanings mentioned above.

Preference is also given to the benzenesulfonamide deriva-
tives of the formula I in which
Q is $Q^1$, $Q^2$, $Q^5$, $Q^7$, $Q^8$, $Q^{10}$, $Q^{12}$, $Q^{13}$, $Q^{17}$, $Q^{20}$, $Q^{21}$, $Q^{22}$, $Q^{23}$, $Q^{24}$, $Q^{27}$, $Q^{31}$, $Q^{32}$, $Q^{34}$, $Q^{38}$ or $Q^{39}$;
particularly preferably $Q^1$, $Q^2$, $Q^5$, $Q^7$, $Q^8$, $Q^{10}$, $Q^{12}$, $Q^{13}$, $Q^{17}$, $Q^{20}$, $Q^{21}$, $Q^{22}$, $Q^{24}$, $Q^{27}$, $Q^{31}$, $Q^{32}$, $Q^{38}$ or $Q^{39}$;
especially preferably $Q^5$, $Q^7$, $Q^{21}$, $Q^{22}$, $Q^{27}$, $Q^{32}$, $Q^{38}$ or $Q^{39}$;
with extraordinary preference $Q^{21}$, $Q^{32}$ or $Q^{38}$.

Preference is also given to the benzenesulfonamide deriva-
tives of the formula I in which
Q is $Q^1$, $Q^2$, $Q^3$, $Q^4$, $Q^6$, $Q^7$, $Q^8$, $Q^9$, $Q^{10}$, $Q^{11}$, $Q^{12}$, $Q^{13}$, $Q^{14}$, $Q^{15}$, $Q^{16}$, $Q^{17}$, $Q^{18}$, $Q^{19}$, $Q^{20}$, $Q^{21}$, $Q^{22}$, $Q^{23}$, $Q^{24}$, $Q^{25}$, $Q^{26}$, $Q^{27}$, $Q^{28}$, $Q^{29}$, $Q^{30}$, $Q^{31}$, $Q^{32}$, $Q^{33}$, $Q^{34}$, $Q^{35}$, $Q^{36}$, $Q^{37}$, $Q^{38}$ or $Q^{39}$,
particularly preferably $Q^1$, $Q^2$, $Q^7$, $Q^8$, $Q^{10}$, $Q^{12}$, $Q^{13}$, $Q^{17}$, $Q^{20}$, $Q^{21}$, $Q^{22}$, $Q^{23}$, $Q^{24}$, $Q^{27}$, $Q^{31}$, $Q^{32}$, $Q^{34}$, $Q^{38}$ or $Q^{39}$,
especially preferably $Q^1$, $Q^2$, $Q^7$, $Q^8$, $Q^{10}$, $Q^{12}$, $Q^{13}$, $Q^{17}$, $Q^{20}$, $Q^{21}$, $Q^{22}$, $Q^{24}$, $Q^{27}$, $Q^{31}$, $Q^{32}$, $Q^{38}$ or $Q^{39}$,
with extraordinary preference $Q^7$, $Q^{21}$, $Q^{22}$, $Q^{27}$, $Q^{32}$, $Q^{38}$ or $Q^{39}$,
with most extraordinary preference $Q^{21}$, $Q^{32}$ or $Q^{38}$.

Preference is also given to the benzenesulfonamide deriva-
tives of the formula I in which
Q is $Q^7$, $Q^{21}$, $Q^{22}$, $Q^{27}$, $Q^{32}$, $Q^{38}$ or $Q^{39}$;
particularly preferably
$Q^7$, where Y is $SO_2$, $SO_2NR^2$ or C(A)B where B=oxygen or $NR^2$;
$Q^{21}$, where Y is $SO_2$, $SO_2NR^2$ or C(A)B where B=oxygen, sulfur or $NR^2$,
preferably Y is $SO_2NR^2$ or C(A)B where B=oxygen or $NR^2$,
more preferably Y is $SO_2NR^2$ or C(A)B where B=oxygen or $NR^2$, and $X^2$ is hydrogen, cyano or halogen, such as fluorine or chlorine;
$Q^{22}$; $Q^{27}$;
$Q^{32}$, where Y is $SO_2$, $SO_2NR^2$ or C(A)B where B=oxygen, sulfur or $NR^2$;
$Q^{38}$ or $Q^{39}$;
especially preferably
$Q^{21}$, where Y is $SO_2$, $SO_2NR^2$ or C(A)B where B=oxygen, sulfur or $NR^2$,
preferably Y is $SO_2NR^2$ or C(A)B where B=oxygen or $NR^2$,
more preferably Y is $SO_2NR^2$ or C(A)B where B=oxygen or $NR^2$, and $X^2$ is hydrogen, cyano or halogen, such as fluorine or chlorine;
$Q^{32}$, where Y is $SO_2$, $SO_2NR^2$ or C(A)B where B=oxygen, sulfur or $NR^2$; or
$Q^{38}$.

Preference is also given to the benzenesulfonamide deriva-
tives of the formula I in which
$X^1$ is hydrogen, fluorine or chlorine;
particularly preferably hydrogen or fluorine;
especially preferably fluorine;
$X^2$ is hydrogen, cyano, $CS$—$NH_2$ or halogen;
particularly preferably hydrogen, halogen, such as fluorine or chlorine;
especially preferably chlorine; and
Q is $Q^1$, $Q^2$, $Q^5$, $Q^7$, $Q^8$, $Q^{10}$, $Q^{12}$, $Q^{13}$, $Q^{17}$, $Q^{20}$, $Q^{21}$, $Q^{22}$, $Q^{23}$, $Q^{24}$, $Q^{27}$, $Q^{31}$, $Q^{32}$, $Q^{34}$, $Q^{38}$ or $Q^{39}$,
particularly preferably $Q^1$, $Q^2$, $Q^5$, $Q^7$, $Q^8$, $Q^{10}$, $Q^{12}$, $Q^{13}$, $Q^{17}$, $Q^{20}$, $Q^{21}$, $Q^{22}$, $Q^{24}$, $Q^{27}$, $Q^{31}$, $Q^{32}$, $Q^{38}$ or $Q^{39}$,
especially preferably $Q^5$, $Q^7$, $Q^{21}$, $Q^{22}$, $Q^{27}$, $Q^{32}$, $Q^{38}$ or $Q^{39}$,
with extraordinary preference $Q^{21}$, $Q^{32}$ or $Q^{38}$.

Preference is also given to the benzenesulfonamide deriva-
tives of the formula I in which
Q is $Q^1$ to $Q^{39}$; and
$R^3$, $R^4$, $R^7$, $R^8$, $R^{11}$, $R^{12}$, $R^{18}$, $R^{19}$, $R^{27}$, $R^{29}$, $R^{32}$, $R^{33}$, $R^{38}$, $R^{39}$, $R^{44}$, $R^{45}$, $R^{46}$ and $R^{47}$ are hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfonyl or amino;
preferably hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl or amino;
especially preferably hydrogen, $CH_3$, $C_2H_5$, $CF_3$, $CHF_2$, $CH_2CF_3$, $OCH_3$, $OCHF_2$, $OCF_2CHF_2$, $SO_2CH_3$ or amino;
$R^5$, $R^6$, $R^9$, $R^{10}$, $R^{15}$, $R^{16}$, $R^{20}$, $R^{21}$, $R^{30}$, $R^{31}$, $R^{35}$, $R^{36}$, $R^{41}$, $R^{42}$ and $R^{43}$
are hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfonyl or amino;
preferably hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl or amino;
especially preferably hydrogen, $CH_3$, $C_2H_5$, $CF_3$, $CHF_2$, $OCH_3$, $OCHF_2$, $SO_2CH_3$ or amino;
$R^{13}$, $R^{14}$, $R^{22}$, $R^{23}$, $R^{25}$ and $R^{26}$
are hydrogen, halogen or $C_1$-$C_4$-alkyl;
particularly preferably hydrogen, halogen or $CH_3$;

especially preferably hydrogen, chlorine or bromine;

$R^{17}, R^{28}, R^{34}, R^{37}$ or $R^{40}$
 are hydrogen, halogen or $C_1$-$C_4$-alkyl;
 particularly preferably hydrogen, halogen or $CH_3$;
 especially preferably hydrogen, chlorine or bromine.

Preference is also given to the benzenesulfonamide derivatives of the formula I in which Q is $Q^5, Q^7, Q^{21}, Q^{22}, Q^{27}, Q^{32}, Q^{38}$ or $Q^{39}$,
 particularly preferably $Q^{21}, Q^{32}$ or $Q^{38}$;

$A^1, A^8, A^9, A^{10}, A^{11}, A^{12}, A^{13}, A^{15}, A^{16}$ and $A^{17}$ are oxygen;

$R^7, R^8, R^{29}, R^{32}, R^{33}, R^{38}, R^{39}, R^{44}, R^{45}, R^{46}, R^{47}$
 are hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfonyl or amino;
 preferably hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl or amino;
 especially preferably hydrogen, $CH_3$, $C_2H_5$, $CF_3$, $CHF_2$, $CH_2CF_3$, $OCH_3$, $OCHF_2$, $OCF_2CHF_2$, $SO_2CH_3$ or amino;

$R^{30}, R^{31}, R^{35}, R^{36}, R^{41}, R^{42}, R^{43}$
 are hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfonyl or amino;
 preferably hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl or amino;
 especially preferably hydrogen, $CH_3$, $C_2H_5$, $CF_3$, $CHF_2$, $OCH_3$, $OCHF_2$, $SO_2CH_3$ or amino; and $R^{34}, R^{37}, R^{40}$
 are hydrogen, halogen or $C_1$-$C_4$-alkyl;
 particularly preferably hydrogen, halogen or $CH_3$;
 especially preferably hydrogen, chlorine or bromine.

Preference is also given to the benzenesulfonamide derivatives of the formula I in which Q is $Q^1, Q^7, Q^8, Q^{10}, Q^{12}, Q^{13}, Q^{21}, Q^{23}, Q^{24}, Q^{31}$ or $Q^{34}$;
$A^1, A^2, A^3, A^4, A^5, A^6, A^7, A^8, A^9, A^{14}, A^{16}$ and $A^{17}$ are oxygen; and $R^3$ and $R^4$, $R^5$ and $R^6$, $R^9$ and $R^{10}$, $R^{15}$ and $R^{16}$, $R^{18}$ and $R^{19}$, $R^{20}$ and $R^{21}$, $R^{30}$ and $R^{31}$ or $R^{46}$ and $R^{47}$ together with the atoms to which they are attached form a three- to seven-membered heterocycle which for its part may be partially or fully halogenated and/or may carry one to three radicals from the group consisting of $C_1$-$C_6$-alkyl and $C_1$-$C_6$-alkoxy;

particularly preferably

Q is $Q^1, Q^7, Q^8, Q^{10}, Q^{12}, Q^{13}, Q^{21}, Q^{24}$ or $Q^{31}$;
$A^1, A^2, A^3, A^4, A^6, A^8, A^9, A^{16}$ and $A^{17}$ are oxygen; and $R^3$ and $R^4$, $R^5$ and $R^6$, $R^9$ and $R^{10}$, $R^{15}$ and $R^{16}$, $R^{18}$ and $R^{19}$, $R^{20}$ and $R^{21}$, $R^{30}$ and $R^{31}$ or $R^{46}$ and $R^{47}$ together with the atoms to which they are attached form a three- to seven-membered heterocycle which for its part may be partially or fully halogenated and/or may carry one to three radicals from the group consisting of $C_1$-$C_6$-alkyl and $C_1$-$C_6$-alkoxy;

especially preferably

Q is $Q^7$ or $Q^{21}$,
$A^8, A^9, A^{16}$ and $A^{17}$ are oxygen;
$R^{29}$ is hydrogen, $C_1$-$C_6$-alkyl or amino; and
$R^{30}$ and $R^{31}$ or $R^{46}$ and $R^{47}$ together with the atoms to which they are attached form a three- to seven-membered heterocycle which for its part may be partially or fully halogenated and/or may carry one to three radicals from the group consisting of $C_1$-$C_6$-alkyl and $C_1$-$C_6$-alkoxy.

Extraordinary preference is given to the compounds of the formula I.1 [corresponds to formula I where $X^1$=fluorine; $X^2$=chlorine; $X^3$=hydrogen; Y=—C(A)B (where A=oxygen, B=$NR^2$); Q=$Q^{21}$ (where $A^8$, $A^9$=oxygen, $R^{29}$=methyl, $R^{30}$=trifluoromethyl and $R^{31}$=hydrogen)], in particular to the compounds of the formulae I.1.1 to I.1.689 of Table 1, where the definitions of the variables $X^1, X^2, X^3, Y, A, B, R^1, R^2$ and Q are of particular importance for the compounds according to the invention not only in combination with one another but in each case also on their own.

TABLE 1

I.1

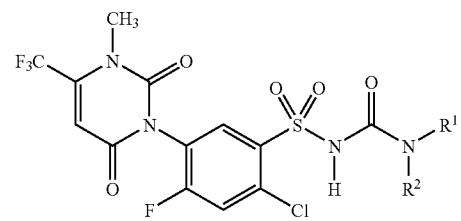

| No. | $R^1$ | $R^2$ |
|---|---|---|
| I.1.1 | $CH_3$ | H |
| I.1.2 | $C_2H_5$ | H |
| I.1.3 | $CH_2CH_2CH_3$ | H |
| I.1.4 | $CH_2CH_2CH_2CH_3$ | H |
| I.1.5 | $CH(CH_3)_2$ | H |
| I.1.6 | $CH(CH_3)CH_2CH_3$ | H |
| I.1.7 | $CH_2CH(CH_3)_2$ | H |
| I.1.8 | $C(CH_3)_3$ | H |
| I.1.9 | $CH(CH_3)CH_2CH_2CH_3$ | H |
| I.1.10 | $CH_2CH(CH_3)CH_2CH_3$ | H |
| I.1.11 | $CH_2CH_2CH(CH_3)_2$ | H |
| I.1.12 | $CH_2CHF_2$ | H |
| I.1.13 | $CH_2CF_3$ | H |
| I.1.14 | $CH_2CH_2Cl$ | H |
| I.1.15 | $CH_2CH_2Br$ | H |

TABLE 1-continued

I.1

[Structure: pyrimidine-2,4-dione with CH3 on N, F3C group, connected to phenyl ring bearing F, Cl, and SO2-NH-C(O)-N(R1)(R2) sulfonylurea group]

| No. | R¹ | R² |
|---|---|---|
| I.1.16 | CH₂CH₂CN | H |
| I.1.17 | CH(CH₃)CN | H |
| I.1.18 | CH₂CH(CH₃)CN | H |
| I.1.19 | cyclopropyl | H |
| I.1.20 | CH₂-cyclopropyl | H |
| I.1.21 | cyclopentyl | H |
| I.1.22 | CH₂-cyclopentyl | H |
| I.1.23 | cyclohexyl | H |
| I.1.24 | CH₂CH=CH₂ | H |
| I.1.25 | C(CH₃)=CH₂ | H |
| I.1.26 | CH=CHCH₃ | H |
| I.1.27 | CH₂CH=CHCH₃ | H |
| I.1.28 | CH₂CF=CF₂ | H |
| I.1.29 | CH₂C≡CH | H |
| I.1.30 | CH(CH₃)—C≡CH | H |
| I.1.31 | CH₂—CO—OCH₃ | H |
| I.1.32 | CH₂CH₂—CO—OCH₃ | H |
| I.1.33 | CH₂—CO—OC₂H₅ | H |
| I.1.34 | CH(CH₃)—CO—OCH₃ | H |
| I.1.35 | C(CH₃)₂—CO—OCH₃ | H |
| I.1.36 | CH=CH—CO—OCH₃ | H |
| I.1.37 | C(CH₃)₂—CO—OCH₂—CH=CH₂ | H |
| I.1.38 | CH₂CH₂OCH₃ | H |
| I.1.39 | CH₂CH₂OC₂H₅ | H |
| I.1.40 | CH₂CH₂SCH₃ | H |
| I.1.41 | CH₂CH₂S(O)CH₃ | H |
| I.1.42 | CH₂CH₂SO₂CH₃ | H |
| I.1.43 | CH₂(1,3-dioxolanyl) | H |
| I.1.44 | CH₂(2-furyl) | H |
| I.1.45 | CH₂(3-furyl) | H |
| I.1.46 | CH₂(2-thienyl) | H |
| I.1.47 | CH₂(3-thienyl) | H |
| I.1.48 | phenyl | H |
| I.1.49 | 2-chlorophenyl | H |
| I.1.50 | 3-chlorophenyl | H |
| I.1.51 | 4-chlorophenyl | H |
| I.1.52 | 2-fluorophenyl | H |
| I.1.53 | 3-fluorophenyl | H |
| I.1.54 | 4-fluorophenyl | H |
| I.1.55 | 2-methylphenyl | H |
| I.1.56 | 3-methylphenyl | H |
| I.1.57 | 4-methylphenyl | H |
| I.1.58 | 2-methoxyphenyl | H |
| I.1.59 | 3-methoxyphenyl | H |
| I.1.60 | 4-methoxyphenyl | H |
| I.1.61 | 2-(methoxycarbonyl)phenyl | H |
| I.1.62 | 3-(methoxycarbonyl)phenyl | H |
| I.1.63 | 4-(methoxycarbonyl)phenyl | H |
| I.1.64 | 2-nitrophenyl | H |
| I.1.65 | 3-nitrophenyl | H |
| I.1.66 | 4-nitrophenyl | H |
| I.1.67 | 2-(dimethylamino)phenyl | H |
| I.1.68 | 3-(dimethylamino)phenyl | H |
| I.1.69 | 4-(dimethylamino)phenyl | H |
| I.1.70 | 2-(trifluoromethyl)phenyl | H |
| I.1.71 | 3-(trifluoromethyl)phenyl | H |
| I.1.72 | 4-(trifluoromethyl)phenyl | H |
| I.1.73 | 3-(phenoxy)phenyl | H |
| I.1.74 | 4-(phenoxy)phenyl | H |
| I.1.75 | 2,4-difluorophenyl | H |
| I.1.76 | 2,4-dichlorophenyl | H |
| I.1.77 | 3,4-difluorophenyl | H |
| I.1.78 | 3,4-dichlorophenyl | H |
| I.1.79 | 3,5-difluorophenyl | H |

TABLE 1-continued

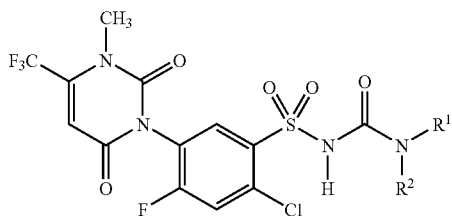

I.1

| No. | R¹ | R² |
|---|---|---|
| I.1.80 | 3,5-dichlorophenyl | H |
| I.1.81 | 2-pyridyl | H |
| I.1.82 | 3-pyridyl | H |
| I.1.83 | 4-pyridyl | H |
| I.1.84 | α-naphthyl | H |
| I.1.84 | benzyl | H |
| I.1.86 | 2-chlorobenzyl | H |
| I.1.87 | 3-chlorobenzyl | H |
| I.1.88 | 4-chlorobenzyl | H |
| I.1.89 | 2-methoxybenzyl | H |
| I.1.90 | 3-methoxybenzyl | H |
| I.1.91 | 4-methoxybenzyl | H |
| I.1.92 | 4-chloro-6-methoxy-1,3-pyrimidin-2-yl | H |
| I.1.93 | 4-methyl-6-rnethoxy-1,3-pyrimidin-2-yl | H |
| I.1.94 | 4-methyl-6-methylamino-1,3-pyrimidin-2-yl | H |
| I.1.95 | 4,6-dimethyl-1,3-pyrimidin-2-yl | H |
| I.1.96 | 4-trifluoromethyl-6-methoxy-1,3-pyrimidin-2-yl | H |
| I.1.97 | 4-methoxy-6-methylamino-1,3-pyrimidin-2-yl | H |
| I.1.98 | 4-difluoromethoxy-6-methyl-1,3-pyrimidin-2-yl | H |
| I.1.99 | 4,6-bis(difluoromethoxy)-1,3-pyrimidin-2-yl | H |
| I.1.100 | 4-methyl-6-methoxy-1,3,5-triazin-2-yl | H |
| I.1.101 | 4,6-dimethyl-1,3,5-triazin-2-yl | H |
| I.1.102 | 4-methylamino-6-methoxy-1,3,5-triazin-2-yl | H |
| I.1.103 | 4-trifluoromethyl-6-methoxy-1,3,5-triazin-2-yl | H |
| I.1.104 | 4,6-dimethoxy-1 3,5-triazin-2-yl | H |
| I.1.105 | $CH_3$ | $CH_3$ |
| I.1.106 | $C_2H_5$— | $CH_3$ |
| I.1.107 | $CH_2CH_2CH_3$ | $CH_3$ |
| I.1.108 | $CH_2CH_2CH_2CH_3$ | $CH_3$ |
| I.1.109 | $CH(CH_3)_2$ | $CH_3$ |
| I.1.110 | $CH(CH_3)C_2H_5$ | $CH_3$ |
| I.1.111 | $CH_2CH(CH_3)_2$ | $CH_3$ |
| I.1.112 | $C(CH_3)_3$ | $CH_3$ |
| I.1.113 | $CH(CH_3)CH_2CH_3$ | $CH_3$ |
| I.1.114 | $CH_2CH(CH_3)CH_2CH_3$ | $CH_3$ |
| I.1.115 | $CH_2CH_2CH(CH_3)_2$ | $CH_3$ |
| I.1.116 | $CH_2CHF_2$ | $CH_3$ |
| I.1.117 | $CH_2CF_3$ | $CH_3$ |
| I.1.118 | $CH_2CH_2Cl$ | $CH_3$ |
| I.1.119 | $CH_2CH_2Br$ | $CH_3$ |
| I.1.120 | $CH_2CH_2CN$ | $CH_3$ |
| I.1.121 | $CH(CH_3)CN$ | $CH_3$ |
| I.1.122 | $CH_2CH(CH_3)CN$ | $CH_3$ |
| I.1.123 | cyclopropyl | $CH_3$ |
| I.1.124 | $CH_2$-cyclopropyl | $CH_3$ |
| I.1.125 | cyclopentyl | $CH_3$ |
| I.1.126 | $CH_2$-cyclopentyl | $CH_3$ |
| I.1.127 | cyclohexyl | $CH_3$ |
| I.1.128 | $CH_2CH=CH_2$ | $CH_3$ |
| I.1.129 | $C(CH_3)=CH_2$ | $CH_3$ |
| I.1.130 | $CH=CHCH_3$ | $CH_3$ |
| I.1.131 | $CH_2CH=CHCH_3$ | $CH_3$ |
| I.1.132 | $CH_2CF=CF_2$ | $CH_3$ |
| I.1.133 | $CH_2C\equiv CH$ | $CH_3$ |
| I.1.134 | $CH(CH_3)-C\equiv CH$ | $CH_3$ |
| I.1.135 | OH | $CH_3$ |
| I.1.136 | $OCH_3$ | $CH_3$ |
| I.1.137 | $CH_2-CO-OCH_3$ | $CH_3$ |
| I.1.138 | $CH_2CH_2-CO-OCH_3$ | $CH_3$ |
| I.1.139 | $CH_2-CO-OC_2H_5$ | $CH_3$ |
| I.1.140 | $CH(CH_3)-CO-OCH_3$ | $CH_3$ |
| I.1.141 | $C(CH_3)_2-CO-OCH_3$ | $CH_3$ |
| I.1.142 | $CH=CH-CO-OCH_3$ | $CH_3$ |
| I.1.143 | $C(CH_3)_2-CO-OCH_2-CH=CH_2$ | $CH_3$ |

TABLE 1-continued

I.1

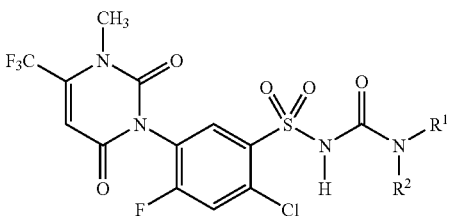

| No. | R¹ | R² |
|---|---|---|
| I.1.144 | CH₂CH₂OCH₃ | CH₃ |
| I.1.145 | CH₂CH₂OC₂H₅ | CH₃ |
| I.1.146 | CH₂CH₂SCH₃ | CH₃ |
| I.1.147 | CH₂CH₂S(O)CH₃ | CH₃ |
| I.1.148 | CH₂CH₂SO₂CH₃ | CH₃ |
| I.1.149 | CH₂(1,3-dioxolanyl) | CH₃ |
| I.1.150 | CH₂(2-furyl) | CH₃ |
| I.1.151 | CH₂(3-furyl) | CH₃ |
| I.1.152 | CH₂(2-thienyl) | CH₃ |
| I.1.153 | CH₂(3-thienyl) | CH₃ |
| I.1.154 | phenyl | CH₃ |
| I.1.155 | 2-chlorophenyl | CH₃ |
| I.1.156 | 3-chlorophenyl | CH₃ |
| I.1.157 | 4-chlorophenyl | CH₃ |
| I.1.158 | 2-fluorophenyl | CH₃ |
| I.1.159 | 3-fluorophenyl | CH₃ |
| I.1.160 | 4-fluorophenyl | CH₃ |
| I.1.161 | 2-methylphenyl | CH₃ |
| I.1.162 | 3-methylphenyl | CH₃ |
| I.1.163 | 4-methylphenyl | CH₃ |
| I.1.164 | 2-methoxyphenyl | CH₃ |
| I.1.165 | 3-methoxyphenyl | CH₃ |
| I.1.166 | 4-methoxyphenyl | CH₃ |
| I.1.167 | 2-(methoxycarbonyl)phenyl | CH₃ |
| I.1.168 | 3-(methoxycarbonyl)phenyl | CH₃ |
| I.1.169 | 4-(methoxycarbonyl)phenyl | CH₃ |
| I.1.170 | 2-nitrophenyl | CH₃ |
| I.1.171 | 3-nitrophenyl | CH₃ |
| I.1.172 | 4-nitrophenyl | CH₃ |
| I.1.173 | 2-(dimethylamino)phenyl | CH₃ |
| I.1.174 | 3-(dimethylamino)phenyl | CH₃ |
| I.1.175 | 4-(dimethylamino)phenyl | CH₃ |
| I.1.176 | 2-(trifluoromethyl)phenyl | CH₃ |
| I.1.177 | 3-(trifluoromethyl)phenyl | CH₃ |
| I.1.178 | 4-(trifluoromethyl)phenyl | CH₃ |
| I.1.179 | 3-(phenoxy)phenyl | CH₃ |
| I.1.180 | 4-(phenoxy)phenyl | CH₃ |
| I.1.181 | 2,4-difluorophenyl | CH₃ |
| I.1.182 | 2,4-dichlorophenyl | CH₃ |
| I.1.183 | 3,4-difluorophenyl | CH₃ |
| I.1.184 | 3,4-dichlorophenyl | CH₃ |
| I.1.185 | 3,5-difluorophenyl | CH₃ |
| I.1.186 | 3,5-dichlorophenyl | CH₃ |
| I.1.187 | 2-pyridyl | CH₃ |
| I.1.188 | 3-pyridyl | CH₃ |
| I.1.189 | 4-pyridyl | CH₃ |
| I.1.190 | α-naphthyl | CH₃ |
| I.1.191 | benzyl | CH₃ |
| I.1.192 | 2-chlorobenzyl | CH₃ |
| I.1.193 | 3-chlorobenzyl | CH₃ |
| I.1.194 | 4-chlorobenzyl | CH₃ |
| I.1.195 | 2-methoxybenzyl | CH₃ |
| I.1.196 | 3-methoxybenzyl | CH₃ |
| I.1.197 | 4-methoxybenzyl | CH₃ |
| I.1.198 | C₂H₅ | C₂H₅ |
| I.1.199 | CH₂CH₂CH₃ | C₂H₅ |
| I.1.200 | CH₂CH₂CH₂CH₃ | C₂H₅ |
| I.1.201 | CH(CH₃)₂ | C₂H₅ |
| I.1.202 | CH(CH₃)CH₂CH₃ | C₂H₅ |
| I.1.203 | CH₂CH(CH₃)₂ | C₂H₅ |
| I.1.204 | C(CH₃)₃ | C₂H₅ |
| I.1.205 | CH(CH₃)CH₂CH₂CH₃ | C₂H₅ |
| I.1.206 | CH₂CH(CH₃)CH₂CH₃ | C₂H₅ |
| I.1.207 | CH₂CH₂CH(CH₃)₂ | C₂H₅ |

TABLE 1-continued

I.1

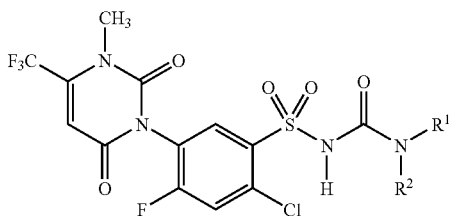

| No. | R¹ | R² |
|---|---|---|
| I.1.208 | $CH_2CHF_2$ | $C_2H_5$ |
| I.1.209 | $CH_2CF_3$ | $C_2H_5$ |
| I.1.210 | $CH_2CH_2Cl$ | $C_2H_5$ |
| I.1.211 | $CH_2CH_2Br$ | $C_2H_5$ |
| I.1.212 | $CH_2CH_2CN$ | $C_2H_5$ |
| I.1.213 | $CH(CH_3)CN$ | $C_2H_5$ |
| I.1.214 | $CH_2CH(CH_3)CN$ | $C_2H_5$ |
| I.1.215 | cyclopropyl | $C_2H_5$ |
| I.1.216 | $CH_2$-cyclopropyl | $C_2H_5$ |
| I.1.217 | cyclopentyl | $C_2H_5$ |
| I.1.218 | $CH_2$-cyclopentyl | $C_2H_5$ |
| I.1.219 | cyclohexyl | $C_2H_5$ |
| I.1.220 | $CH_2CH=CH_2$ | $C_2H_5$ |
| I.1.221 | $C(CH_3)=CH_2$ | $C_2H_5$ |
| I.1.222 | $CH=CHCH_3$ | $C_2H_5$ |
| I.1.223 | $CH_2CH=CHCH_3$ | $C_2H_5$ |
| I.1.224 | $CH_2-CF=CF_2$ | $C_2H_5$ |
| I.1.225 | $CH_2-C\equiv CH$ | $C_2H_5$ |
| I.1.226 | $CH(CH_3)-C\equiv CH$ | $C_2H_5$ |
| I.1.227 | OH | $C_2H_5$ |
| I.1.228 | $OCH_3$ | $C_2H_5$ |
| I.1.229 | $CH_2-CO-OCH_3$ | $C_2H_5$ |
| I.1.230 | $CH_2-CH_2-CO-OCH_3$ | $C_2H_5$ |
| I.1.231 | $CH_2-CO-OC_2H_5$ | $C_2H_5$ |
| I.1.232 | $CH(CH_3)-CO-OCH_3$ | $C_2H_5$ |
| I.1.233 | $C(CH_3)_2-CO-OCH_3$ | $C_2H_5$ |
| I.1.234 | $CH=CH-CO-OCH_3$ | $C_2H_5$ |
| I.1.235 | $C(CH_3)_2-CO-OCH_2-CH=CH_2$ | $C_2H_5$ |
| I.1.236 | $CH_2CH_2OCH_3$ | $C_2H_5$ |
| I.1.237 | $CH_2CH_2OC_2H_5$ | $C_2H_5$ |
| I.1.238 | $CH_2CH_2SCH_3$ | $C_2H_5$ |
| I.1.239 | $CH_2CH_2S(O)CH_3$ | $C_2H_5$ |
| I.1.240 | $CH_2CH_2SO_2CH_3$ | $C_2H_5$ |
| I.1.241 | $CH_2$(1,3-dioxolanyl) | $C_2H_5$ |
| I.1.242 | $CH_2$(2-furyl) | $C_2H_5$ |
| I.1.243 | $CH_2$(3-furyl) | $C_2H_5$ |
| I.1.244 | $CH_2$(2-thienyl) | $C_2H_5$ |
| I.1.245 | $CH_2$(3-thienyl) | $C_2H_5$ |
| I.1.246 | phenyl | $C_2H_5$ |
| I.1.247 | 2-chlorophenyl | $C_2H_5$ |
| I.1.248 | 3-chlorophenyl | $C_2H_5$ |
| I.1.249 | 4-chlorophenyl | $C_2H_5$ |
| I.1.250 | 2-fluorophenyl | $C_2H_5$ |
| I.1.251 | 3-fluorophenyl | $C_2H_5$ |
| I.1.252 | 4-fluorophenyl | $C_2H_5$ |
| I.1.253 | 2-methylphenyl | $C_2H_5$ |
| I.1.254 | 3-methylphenyl | $C_2H_5$ |
| I.1.255 | 4-methylphenyl | $C_2H_5$ |
| I.1.256 | 2-methoxyphenyl | $C_2H_5$ |
| I.1.257 | 3-methoxyphenyl | $C_2H_5$ |
| I.1.258 | 4-methoxyphenyl | $C_2H_5$ |
| I.1.259 | 2-(methoxycarbonyl)phenyl | $C_2H_5$ |
| I.1.260 | 3-(methoxycarbonyl)phenyl | $C_2H_5$ |
| I.1.261 | 4-(methoxycarbonyl)phenyl | $C_2H_5$ |
| I.1.262 | 2-nitrophenyl | $C_2H_5$ |
| I.1.263 | 3-nitrophenyl | $C_2H_5$ |
| I.1.264 | 4-nitrophenyl | $C_2H_5$ |
| I.1.265 | 2-(dimethylamino)phenyl | $C_2H_5$ |
| I.1.266 | 3-(dimethylamino)phenyl | $C_2H_5$ |
| I.1.267 | 4-(dimethylamino)phenyl | $C_2H_5$ |
| I.1.268 | 2-(trifluoromethyl)phenyl | $C_2H_5$ |
| I.1.269 | 3-(trifluoromethyl)phenyl | $C_2H_5$ |
| I.1.270 | 4-(trifluoromethyl)phenyl | $C_2H_5$ |
| I.1.271 | 3-(phenoxy)phenyl | $C_2H_5$ |

TABLE 1-continued

I.1

| No. | R¹ | R² |
|---|---|---|
| I.1.272 | 4-(phenoxy)phenyl | $C_2H_5$ |
| I.1.273 | 2,4-difluorophenyl | $C_2H_5$ |
| I.1.274 | 2,4-dichlorophenyl | $C_2H_5$ |
| I.1.275 | 3,4-difluorophenyl | $C_2H_5$ |
| I.1.276 | 3,4-dichlorophenyl | $C_2H_5$ |
| I.1.277 | 3,5-difluorophenyl | $C_2H_5$ |
| I.1.278 | 3,5-dichlorophenyl | $C_2H_5$ |
| I.1.279 | 2-pyridyl | $C_2H_5$ |
| I.1.280 | 3-pyridyl | $C_2H_5$ |
| I.1.281 | 4-pyridyl | $C_2H_5$ |
| I.1.282 | α-naphthyl | $C_2H_5$ |
| I.1.283 | benzyl | $C_2H_5$ |
| I.1.284 | 2-chlorobenzyl | $C_2H_5$ |
| I.1.285 | 3-chlorobenzyl | $C_2H_5$ |
| I.1.286 | 4-chlorobenzyl | $C_2H_5$ |
| I.1.287 | 2-methoxybenzyl | $C_2H_5$ |
| I.1.288 | 3-methoxybenzyl | $C_2H_5$ |
| I.1.289 | 4-methoxybenzyl | $C_2H_5$ |
| I.1.290 | $CH_2CH_2CH_3$ | $CH_2CH_2CH_3$ |
| I.1.291 | $CH_2CH_2CH_2CH_3$ | $CH_2CH_2CH_3$ |
| I.1.292 | $CH(CH_3)_2$ | $CH_2CH_2CH_3$ |
| I.1.293 | $CH(CH_3)CH_2CH_3$ | $CH_2CH_2CH_3$ |
| I.1.294 | $CH_2CH(CH_3)_2$ | $CH_2CH_2CH_3$ |
| I.1.295 | $C(CH_3)_3$ | $CH_2CH_2CH_3$ |
| I.1.296 | $CH(CH_3)CH_2CH_2CH_3$ | $CH_2CH_2CH_3$ |
| I.1.297 | $CH_2CH(CH_3)CH_2CH_3$ | $CH_2CH_2CH_3$ |
| I.1.298 | $CH_2CH_2CH(CH_3)_2$ | $CH_2CH_2CH_3$ |
| I.1.299 | $CH_2CHF_2$ | $CH_2CH_2CH_3$ |
| I.1.300 | $CH_2CF_3$ | $CH_2CH_2CH_3$ |
| I.1.301 | $CH_2CH_2Cl$ | $CH_2CH_2CH_3$ |
| I.1.302 | $CH_2CH_2Br$ | $CH_2CH_2CH_3$ |
| I.1.303 | $CH_2CH_2CN$ | $CH_2CH_2CH_3$ |
| I.1.304 | $CH(CH_3)CN$ | $CH_2CH_2CH_3$ |
| I.1.305 | $CH_2CH(CH_3)CN$ | $CH_2CH_2CH_3$ |
| I.1.306 | cyclopropyl | $CH_2CH_2CH_3$ |
| I.1.307 | $CH_2$-cyclopropyl | $CH_2CH_2CH_3$ |
| I.1.308 | cyclopentyl | $CH_2CH_2CH_3$ |
| I.1.309 | $CH_2$-cyclopentyl | $CH_2CH_2CH_3$ |
| I.1.310 | cyclohexyl | $CH_2CH_2CH_3$ |
| I.1.311 | $CH_2CH=CH_2$ | $CH_2CH_2CH_3$ |
| I.1.312 | $C(CH_3)=CH_2$ | $CH_2CH_2CH_3$ |
| I.1.313 | $CH=CHCH_3$ | $CH_2CH_2CH_3$ |
| I.1.314 | $CH_2CH=CHCH_3$ | $CH_2CH_2CH_3$ |
| I.1.315 | $CH_2CF=CF_2$ | $CH_2CH_2CH_3$ |
| I.1.316 | $CH_2-C\equiv CH$ | $CH_2CH_2CH_3$ |
| I.1.317 | $CH(CH_3)-C\equiv CH$ | $CH_2CH_2CH_3$ |
| I.1.318 | OH | $CH_2CH_2CH_3$ |
| I.1.319 | $OCH_3$ | $CH_2CH_2CH_3$ |
| I.1.320 | $CH_2-CO-OCH_3$ | $CH_2CH_2CH_3$ |
| I.1.321 | $CH_2-CH_2-CO-OCH_3$ | $CH_2CH_2CH_3$ |
| I.1.322 | $CH_2-CO-OC_2H_5$ | $CH_2CH_2CH_3$ |
| I.1.323 | $CH(CH_3)-CO-OCH_3$ | $CH_2CH_2CH_3$ |
| I.1.324 | $C(CH_3)_2-CO-OCH_3$ | $CH_2CH_2CH_3$ |
| I.1.325 | $CH=CH-CO-OCH_3$ | $CH_2CH_2CH_3$ |
| I.1.326 | $C(CH_3)_2-CO-OCH_2-CH=CH_2$ | $CH_2CH_2CH_3$ |
| I.1.327 | $CH_2CH_2OCH_3$ | $CH_2CH_2CH_3$ |
| I.1.328 | $CH_2CH_2OC_2H_5$ | $CH_2CH_2CH_3$ |
| I.1.329 | $CH_2CH_2SCH_3$ | $CH_2CH_2CH_3$ |
| I.1.330 | $CH_2CH_2S(O)CH_3$ | $CH_2CH_2CH_3$ |
| I.1.331 | $CH_2CH_2SO_2CH_3$ | $CH_2CH_2CH_3$ |
| I.1.332 | $CH_2(1,3$-dioxolanyl) | $CH_2CH_2CH_3$ |
| I.1.333 | $CH_2(2$-furyl) | $CH_2CH_2CH_3$ |
| I.1.334 | $CH_2(3$-furyl) | $CH_2CH_2CH_3$ |
| I.1.335 | $CH_2(2$-thienyl) | $CH_2CH_2CH_3$ |

TABLE 1-continued

I.1

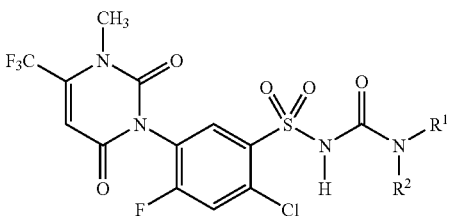

| No. | R¹ | R² |
|---|---|---|
| I.1.336 | CH₂(3-thienyl) | CH₂CH₂CH₃ |
| I.1.337 | phenyl | CH₂CH₂CH₃ |
| I.1.338 | 2-chlorophenyl | CH₂CH₂CH₃ |
| I.1.339 | 3-chlorophenyl | CH₂CH₂CH₃ |
| I.1.340 | 4-chlorophenyl | CH₂CH₂CH₃ |
| I.1.341 | 2-fluorophenyl | CH₂CH₂CH₃ |
| I.1.342 | 3-fluorophenyl | CH₂CH₂CH₃ |
| I.1.343 | 4-fluorophenyl | CH₂CH₂CH₃ |
| I.1.344 | 2-methylphenyl | CH₂CH₂CH₃ |
| I.1.345 | 3-methylphenyl | CH₂CH₂CH₃ |
| I.1.346 | 4-methylphenyl | CH₂CH₂CH₃ |
| I.1.347 | 2-methoxyphenyl | CH₂CH₂CH₃ |
| I.1.348 | 3-methoxyphenyl | CH₂CH₂CH₃ |
| I.1.349 | 4-methoxyphenyl | CH₂CH₂CH₃ |
| I.1.350 | 2-(methoxycarbonyl)phenyl | CH₂CH₂CH₃ |
| I.1.351 | 3-(methoxycarbonyl)phenyl | CH₂CH₂CH₃ |
| I.1.352 | 4-(methoxycarbonyl)phenyl | CH₂CH₂CH₃ |
| I.1.353 | 2-nitrophenyl | CH₂CH₂CH₃ |
| I.1.354 | 3-nitrophenyl | CH₂CH₂CH₃ |
| I.1.355 | 4-nitrophenyl | CH₂CH₂CH₃ |
| I.1.356 | 2-(dimethylamino)phenyl | CH₂CH₂CH₃ |
| I.1.357 | 3-(dimethylamino)phenyl | CH₂CH₂CH₃ |
| I.1.358 | 4-(dimethylamino)phenyl | CH₂CH₂CH₃ |
| I.1.359 | 2-(trifluoromethyl)phenyl | CH₂CH₂CH₃ |
| I.1.360 | 3-(trifluoromethyl)phenyl | CH₂CH₂CH₃ |
| I.1.361 | 4-(trifluoromethyl)phenyl | CH₂CH₂CH₃ |
| I.1.362 | 3-(phenoxy)phenyl | CH₂CH₂CH₃ |
| I.1.363 | 4-(phenoxy)phenyl | CH₂CH₂CH₃ |
| I.1.364 | 2,4-difluorophenyl | CH₂CH₂CH₃ |
| I.1.365 | 2,4-dichlorophenyl | CH₂CH₂CH₃ |
| I.1.366 | 3,4-difluorophenyl | CH₂CH₂CH₃ |
| I.1.367 | 3,4-dichlorophenyl | CH₂CH₂CH₃ |
| I.1.368 | 3,5-difluorophenyl | CH₂CH₂CH₃ |
| I.1.369 | 3,5-dichlorophenyl | CH₂CH₂CH₃ |
| I.1.370 | 2-pyridyl | CH₂CH₂CH₃ |
| I.1.371 | 3-pyridyl | CH₂CH₂CH₃ |
| I.1.372 | 4-pyridyl | CH₂CH₂CH₃ |
| I.1.373 | α-naphthyl | CH₂CH₂CH₃ |
| I.1.374 | benzyl | CH₂CH₂CH₃ |
| I.1.375 | 2-chlorobenzyl | CH₂CH₂CH₃ |
| I.1.376 | 3-chlorobenzyl | CH₂CH₂CH₃ |
| I.1.377 | 4-chlorobenzyl | CH₂CH₂CH₃ |
| I.1.378 | 2-methoxybenzyl | CH₂CH₂CH₃ |
| I.1.379 | 3-methoxybenzyl | CH₂CH₂CH₃ |
| I.1.380 | 4-methoxybenzyl | CH₂CH₂CH₃ |
| I.1.381 | CH₂CH₂CH₂CH₃ | CH(CH₃)₂ |
| I.1.382 | CH(CH₃)₂ | CH(CH₃)₂ |
| I.1.383 | CH(CH₃)CH₂CH₃ | CH(CH₃)₂ |
| I.1.384 | CH₂CH(CH₃)₂ | CH(CH₃)₂ |
| I.1.385 | C(CH₃)₃ | CH(CH₃)₂ |
| I.1.386 | CH(CH₃)CH₂CH₂CH₃ | CH(CH₃)₂ |
| I.1.387 | CH₂CH(CH₃)CH₂CH₃ | CH(CH₃)₂ |
| I.1.388 | CH₂CH₂CH(CH₃)₂ | CH(CH₃)₂ |
| I.1.389 | CH₂CHF₂ | CH(CH₃)₂ |
| I.1.390 | CH₂CF₃ | CH(CH₃)₂ |
| I.1.391 | CH₂CH₂Cl | CH(CH₃)₂ |
| I.1.392 | CH₂CH₂Br | CH(CH₃)₂ |
| I.1.393 | CH₂CH₂CN | CH(CH₃)₂ |
| I.1.394 | CH(CH₃)CN | CH(CH₃)₂ |
| I.1.395 | CH₂CH(CH₃)CN | CH(CH₃)₂ |
| I.1.396 | cyclopropyl | CH(CH₃)₂ |
| I.1.397 | CH₂-cyclopropyl | CH(CH₃)₂ |
| I.1.398 | cyclopentyl | CH(CH₃)₂ |
| I.1.399 | CH₂-cyclopentyl | CH(CH₃)₂ |

TABLE 1-continued

I.1

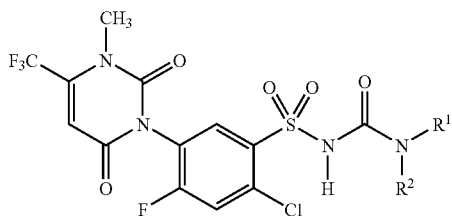

| No. | R$^1$ | R$^2$ |
|---|---|---|
| I.1.400 | cyclohexyl | CH(CH$_3$)$_2$ |
| I.1.401 | CH$_2$CH=CH$_2$ | CH(CH$_3$)$_2$ |
| I.1.402 | C(CH$_3$)=CH$_2$ | CH(CH$_3$)$_2$ |
| I.1.403 | CH=CHCH$_3$ | CH(CH$_3$)$_2$ |
| I.1.404 | CH$_2$CH=CHCH$_3$ | CH(CH$_3$)$_2$ |
| I.1.405 | CH$_2$CF=CF$_2$ | CH(CH$_3$)$_2$ |
| I.1.406 | CH$_2$—C≡CH | CH(CH$_3$)$_2$ |
| I.1.407 | CH(CH$_3$)—C≡CH | CH(CH$_3$)$_2$ |
| I.1.408 | OH | CH(CH$_3$)$_2$ |
| I.1.409 | OCH$_3$ | CH(CH$_3$)$_2$ |
| I.1.410 | CH$_2$—CO—OCH$_3$ | CH(CH$_3$)$_2$ |
| I.1.411 | CH$_2$—CH$_2$—CO—OCH$_3$ | CH(CH$_3$)$_2$ |
| I.1.412 | CH$_2$—CO—OC$_2$H$_5$ | CH(CH$_3$)$_2$ |
| I.1.413 | CH(CH$_3$)—CO—OCH$_3$ | CH(CH$_3$)$_2$ |
| I.1.414 | C(CH$_3$)$_2$—CO—OCH$_3$ | CH(CH$_3$)$_2$ |
| I.1.415 | CH=CH—CO—OCH$_3$ | CH(CH$_3$)$_2$ |
| I.1.416 | C(CH$_3$)$_2$—CO—OCH$_2$—CH=CH$_2$ | CH(CH$_3$)$_2$ |
| I.1.417 | CH$_2$CH$_2$OCH$_3$ | CH(CH$_3$)$_2$ |
| I.1.418 | CH$_2$CH$_2$OC$_2$H$_5$ | CH(CH$_3$)$_2$ |
| I.1.419 | CH$_2$CH$_2$SCH$_3$ | CH(CH$_3$)$_2$ |
| I.1.420 | CH$_2$CH$_2$S(O)CH$_3$ | CH(CH$_3$)$_2$ |
| I.1.421 | CH$_2$CH$_2$SO$_2$CH$_3$ | CH(CH$_3$)$_2$ |
| I.1.422 | CH$_2$(1,3-dioxolanyl) | CH(CH$_3$)$_2$ |
| I.1.423 | CH$_2$(2-furyl) | CH(CH$_3$)$_2$ |
| I.1.424 | CH$_2$(3-furyl) | CH(CH$_3$)$_2$ |
| I.1.425 | CH$_2$(2-thienyl) | CH(CH$_3$)$_2$ |
| I.1.426 | CH$_2$(3-thienyl) | CH(CH$_3$)$_2$ |
| I.1.427 | phenyl | CH(CH$_3$)$_2$ |
| I.1.428 | 2-chlorophenyl | CH(CH$_3$)$_2$ |
| I.1.429 | 3-chlorophenyl | CH(CH$_3$)$_2$ |
| I.1.430 | 4-chlorophenyl | CH(CH$_3$)$_2$ |
| I.1.431 | 2-fluorophenyl | CH(CH$_3$)$_2$ |
| I.1.432 | 3-fluorophenyl | CH(CH$_3$)$_2$ |
| I.1.433 | 4-fluorophenyl | CH(CH$_3$)$_2$ |
| I.1.434 | 2-methylphenyl | CH(CH$_3$)$_2$ |
| I.1.435 | 3-methylphenyl | CH(CH$_3$)$_2$ |
| I.1.436 | 4-methylphenyl | CH(CH$_3$)$_2$ |
| I.1.437 | 2-methoxyphenyl | CH(CH$_3$)$_2$ |
| I.1.438 | 3-methoxyphenyl | CH(CH$_3$)$_2$ |
| I.1.439 | 4-methoxyphenyl | CH(CH$_3$)$_2$ |
| I.1.440 | 2-(methoxycarbonyl)phenyl | CH(CH$_3$)$_2$ |
| I.1.441 | 3-(methoxycarbonyl)phenyl | CH(CH$_3$)$_2$ |
| I.1.442 | 4-(methoxycarbonyl)phenyl | CH(CH$_3$)$_2$ |
| I.1.443 | 2-nitrophenyl | CH(CH$_3$)$_2$ |
| I.1.444 | 3-nitrophenyl | CH(CH$_3$)$_2$ |
| I.1.445 | 4-nitrophenyl | CH(CH$_3$)$_2$ |
| I.1.446 | 2-(dimethylamino)phenyl | CH(CH$_3$)$_2$ |
| I.1.447 | 3-(dimethylamino)phenyl | CH(CH$_3$)$_2$ |
| I.1.448 | 4-(dimethylamino)phenyl | CH(CH$_3$)$_2$ |
| I.1.449 | 2-(trifluoromethyl)phenyl | CH(CH$_3$)$_2$ |
| I.1.450 | 3-(trifluoromethyl)phenyl | CH(CH$_3$)$_2$ |
| I.1.451 | 4-(trifluoromethyl)phenyl | CH(CH$_3$)$_2$ |
| I.1.452 | 3-(phenoxy)phenyl | CH(CH$_3$)$_2$ |
| I.1.453 | 4-(phenoxy)phenyl | CH(CH$_3$)$_2$ |
| I.1.454 | 2,4-difluorophenyl | CH(CH$_3$)$_2$ |
| I.1.455 | 2,4-dichlorophenyl | CH(CH$_3$)$_2$ |
| I.1.456 | 3,4-difluorophenyl | CH(CH$_3$)$_2$ |
| I.1.457 | 3,4-dichlorophenyl | CH(CH$_3$)$_2$ |
| I.1.458 | 3,5-difluorophenyl | CH(CH$_3$)$_2$ |
| I.1.459 | 3,5-dichlorophenyl | CH(CH$_3$)$_2$ |
| I.1.460 | 2-pyridyl | CH(CH$_3$)$_2$ |
| I.1.461 | 3-pyridyl | CH(CH$_3$)$_2$ |
| I.1.462 | 4-pyridyl | CH(CH$_3$)$_2$ |
| I.1.463 | α-naphthyl | CH(CH$_3$)$_2$ |

TABLE 1-continued

I.1

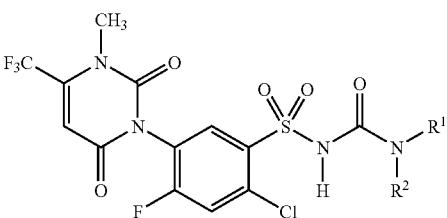

| No. | $R^1$ | $R^2$ |
|---|---|---|
| I.1.464 | benzyl | $CH(CH_3)_2$ |
| I.1.465 | 2-chlorobenzyl | $CH(CH_3)_2$ |
| I.1.466 | 3-chlorobenzyl | $CH(CH_3)_2$ |
| I.1.467 | 4-chlorobenzyl | $CH(CH_3)_2$ |
| I.1.468 | 2-methoxybenzyl | $CH(CH_3)_2$ |
| I.1.469 | 3-methoxybenzyl | $CH(CH_3)_2$ |
| I.1.470 | 4-methoxybenzyl | $CH(CH_3)_2$ |
| I.1.471 | $CH(CH_3)CH_2CH_3$ | $CH_2CH_2CH_2CH_3$ |
| I.1.472 | $CH_2CH(CH_3)_2$ | $CH_2CH_2CH_2CH_3$ |
| I.1.473 | $C(CH_3)_3$ | $CH_2CH_2CH_2CH_3$ |
| I.1.474 | $CH(CH_3)CH_2CH_2CH_3$ | $CH_2CH_2CH_2CH_3$ |
| I.1.475 | $CH_2CH(CH_3)CH_2CH_3$ | $CH_2CH_2CH_2CH_3$ |
| I.1.476 | $CH_2CH_2CH(CH_3)_2$ | $CH_2CH_2CH_2CH_3$ |
| I.1.477 | $CH_2CHF_2$ | $CH_2CH_2CH_2CH_3$ |
| I.1.478 | $CH_2CF_3$ | $CH_2CH_2CH_2CH_3$ |
| I.1.479 | $CH_2CH_2Cl$ | $CH_2CH_2CH_2CH_3$ |
| I.1.480 | $CH_2CH_2Br$ | $CH_2CH_2CH_2CH_3$ |
| I.1.481 | $CH_2CH_2CN$ | $CH_2CH_2CH_2CH_3$ |
| I.1.482 | $CH(CH_3)CN$ | $CH_2CH_2CH_2CH_3$ |
| I.1.483 | $CH_2CH(CH_3)CN$ | $CH_2CH_2CH_2CH_3$ |
| I.1.484 | cyclopropyl | $CH_2CH_2CH_2CH_3$ |
| I.1.485 | $CH_2$-cyclopropyl | $CH_2CH_2CH_2CH_3$ |
| I.1.486 | cyclopentyl | $CH_2CH_2CH_2CH_3$ |
| I.1.487 | $CH_2$-cyclopentyl | $CH_2CH_2CH_2CH_3$ |
| I.1.488 | cyclohexyl | $CH_2CH_2CH_2CH_3$ |
| I.1.489 | $CH_2CH=CH_2$ | $CH_2CH_2CH_2CH_3$ |
| I.1.490 | $C(CH_3)=CH_2$ | $CH_2CH_2CH_2CH_3$ |
| I.1.491 | $CH=CHCH_3$ | $CH_2CH_2CH_2CH_3$ |
| I.1.492 | $CH_2CH=CHCH_3$ | $CH_2CH_2CH_2CH_3$ |
| I.1.493 | $CH_2CF=CF_2$ | $CH_2CH_2CH_2CH_3$ |
| I.1.494 | $CH_2-C\equiv CH$ | $CH_2CH_2CH_2CH_3$ |
| I.1.495 | $CH(CH_3)-C\equiv CH$ | $CH_2CH_2CH_2CH_3$ |
| I.1.496 | OH | $CH_2CH_2CH_2CH_3$ |
| I.1.497 | $OCH_3$ | $CH_2CH_2CH_2CH_3$ |
| I.1.498 | $CH_2-CO-OCH_3$ | $CH_2CH_2CH_2CH_3$ |
| I.1.499 | $CH_2-CH_2-CO-OCH_3$ | $CH_2CH_2CH_2CH_3$ |
| I.1.500 | $CH_2-CO-OC_2H_5$ | $CH_2CH_2CH_2CH_3$ |
| I.1.501 | $CH(CH_3)-CO-OCH_3$ | $CH_2CH_2CH_2CH_3$ |
| I.1.502 | $C(CH_3)_2-CO-OCH_3$ | $CH_2CH_2CH_2CH_3$ |
| I.1.503 | $CH=CH-CO-OCH_3$ | $CH_2CH_2CH_2CH_3$ |
| I.1.504 | $C(CH_3)_2-CO-OCH_2-CH=CH_2$ | $CH_2CH_2CH_2CH_3$ |
| I.1.505 | $CH_2CH_2OCH_3$ | $CH_2CH_2CH_2CH_3$ |
| I.1.506 | $CH_2CH_2OC_2H_5$ | $CH_2CH_2CH_2CH_3$ |
| I.1.507 | $CH_2CH_2SCH_3$ | $CH_2CH_2CH_2CH_3$ |
| I.1.508 | $CH_2CH_2S(O)CH_3$ | $CH_2CH_2CH_2CH_3$ |
| I.1.509 | $CH_2CH_2SO_2CH_3$ | $CH_2CH_2CH_2CH_3$ |
| I.1.510 | $CH_2(1,3$-dioxolanyl) | $CH_2CH_2CH_2CH_3$ |
| I.1.511 | $CH_2(2$-furyl) | $CH_2CH_2CH_2CH_3$ |
| I.1.512 | $CH_2(3$-furyl) | $CH_2CH_2CH_2CH_3$ |
| I.1.513 | $CH_2(2$-thienyl) | $CH_2CH_2CH_2CH_3$ |
| I.1.514 | $CH_2(3$-thienyl) | $CH_2CH_2CH_2CH_3$ |
| I.1.515 | phenyl | $CH_2CH_2CH_2CH_3$ |
| I.1.516 | 2-chlorophenyl | $CH_2CH_2CH_2CH_3$ |
| I.1.517 | 3-chlorophenyl | $CH_2CH_2CH_2CH_3$ |
| I.1.518 | 4-chlorophenyl | $CH_2CH_2CH_2CH_3$ |
| I.1.519 | 2-fluorophenyl | $CH_2CH_2CH_2CH_3$ |
| I.1.520 | 3-fluorophenyl | $CH_2CH_2CH_2CH_3$ |
| I.1.521 | 4-fluorophenyl | $CH_2CH_2CH_2CH_3$ |
| I.1.522 | 2-methylphenyl | $CH_2CH_2CH_2CH_3$ |
| I.1.523 | 3-methylphenyl | $CH_2CH_2CH_2CH_3$ |
| I.1.524 | 4-methylphenyl | $CH_2CH_2CH_2CH_3$ |
| I.1.525 | 2-methoxyphenyl | $CH_2CH_2CH_2CH_3$ |
| I.1.526 | 3-methoxyphenyl | $CH_2CH_2CH_2CH_3$ |
| I.1.527 | 4-methoxyphenyl | $CH_2CH_2CH_2CH_3$ |

TABLE 1-continued

I.1

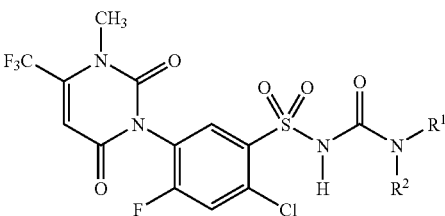

| No. | R¹ | R² |
|---|---|---|
| I.1.528 | 2-(methoxycarbonyl)phenyl | $CH_2CH_2CH_2CH_3$ |
| I.1.529 | 3-(methoxycarbonyl)phenyl | $CH_2CH_2CH_2CH_3$ |
| I.1.530 | 4-(methoxycarbonyl)phenyl | $CH_2CH_2CH_2CH_3$ |
| I.1.531 | 2-nitrophenyl | $CH_2CH_2CH_2CH_3$ |
| I.1.532 | 3-nitrophenyl | $CH_2CH_2CH_2CH_3$ |
| I.1.689 | 4-nitrophenyl | $CH_2CH_2CH_2CH_3$ |
| I.1.534 | 2-(dimethylamino)phenyl | $CH_2CH_2CH_2CH_3$ |
| I.1.535 | 3-(dimethylamino)phenyl | $CH_2CH_2CH_2CH_3$ |
| I.1.536 | 4-(dimethylamino)phenyl | $CH_2CH_2CH_2CH_3$ |
| I.1.537 | 2-(trifluoromethyl)phenyl | $CH_2CH_2CH_2CH_3$ |
| I.1.538 | 3-(trifluoromethyl)phenyl | $CH_2CH_2CH_2CH_3$ |
| I.1.539 | 4-(trifluoromethyl)phenyl | $CH_2CH_2CH_2CH_3$ |
| I.1.540 | 3-(phenoxy)phenyl | $CH_2CH_2CH_2CH_3$ |
| I.1.541 | 4-(phenoxy)phenyl | $CH_2CH_2CH_2CH_3$ |
| I.1.542 | 2,4-difluorophenyl | $CH_2CH_2CH_2CH_3$ |
| I.1.543 | 2,4-dichlorophenyl | $CH_2CH_2CH_2CH_3$ |
| I.1.544 | 3,4-difluorophenyl | $CH_2CH_2CH_2CH_3$ |
| I.1.545 | 3,4-dichlorophenyl | $CH_2CH_2CH_2CH_3$ |
| I.1.546 | 3,5-difluorophenyl | $CH_2CH_2CH_2CH_3$ |
| I.1.547 | 3,5-dichlorophenyl | $CH_2CH_2CH_2CH_3$ |
| I.1.548 | 2-pyridyl | $CH_2CH_2CH_2CH_3$ |
| I.1.549 | 3-pyridyl | $CH_2CH_2CH_2CH_3$ |
| I.1.550 | 4-pyridyl | $CH_2CH_2CH_2CH_3$ |
| I.1.551 | α-naphthyl | $CH_2CH_2CH_2CH_3$ |
| I.1.552 | benzyl | $CH_2CH_2CH_2CH_3$ |
| I.1.553 | 2-chlorobenzyl | $CH_2CH_2CH_2CH_3$ |
| I.1.554 | 3-chlorobenzyl | $CH_2CH_2CH_2CH_3$ |
| I.1.555 | 4-chlorobenzyl | $CH_2CH_2CH_2CH_3$ |
| I.1.556 | 2-methoxybenzyl | $CH_2CH_2CH_2CH_3$ |
| I.1.557 | 3-methoxybenzyl | $CH_2CH_2CH_2CH_3$ |
| I.1.558 | 4-methoxybenzyl | $CH_2CH_2CH_2CH_3$ |
| I.1.559 | $CH(CH_3)CH_2CH_3$ | $CH_2CH(CH_3)_2$ |
| I.1.560 | $CH_2CH(CH_3)_2$ | $CH_2CH(CH_3)_2$ |
| I.1.561 | $CH(CH_3)CH_2CH_2CH_3$ | $CH_2CH(CH_3)_2$ |
| I.1.562 | $CH_2CH(CH_3)CH_2CH_3$ | $CH_2CH(CH_3)_2$ |
| I.1.563 | $CH_2CH_2CH(CH_3)_2$ | $CH_2CH(CH_3)_2$ |
| I.1.564 | $CH_2CHF_2$ | $CH_2CH(CH_3)_2$ |
| I.1.565 | $CH_2CF_3$ | $CH_2CH(CH_3)_2$ |
| I.1.566 | $CH_2CH_2Cl$ | $CH_2CH(CH_3)_2$ |
| I.1.567 | $CH_2CH_2Br$ | $CH_2CH(CH_3)_2$ |
| I.1.568 | $CH_2CH_2CN$ | $CH_2CH(CH_3)_2$ |
| I.1.569 | $CH(CH_3)CN$ | $CH_2CH(CH_3)_2$ |
| I.1.570 | $CH_2CH(CH_3)CN$ | $CH_2CH(CH_3)_2$ |
| I.1.571 | cyclopropyl | $CH_2CH(CH_3)_2$ |
| I.1.572 | $CH_2$-cyclopropyl | $CH_2CH(CH_3)_2$ |
| I.1.573 | cyclopentyl | $CH_2CH(CH_3)_2$ |
| I.1.574 | $CH_2$-cyclopentyl | $CH_2CH(CH_3)_2$ |
| I.1.575 | cyclohexyl | $CH_2CH(CH_3)_2$ |
| I.1.576 | $CH_2CH{=}CH_2$ | $CH_2CH(CH_3)_2$ |
| I.1.577 | $C(CH_3){=}CH_2$ | $CH_2CH(CH_3)_2$ |
| I.1.578 | $CH{=}CHCH_3$ | $CH_2CH(CH_3)_2$ |
| I.1.579 | $CH_2CH{=}CHCH_3$ | $CH_2CH(CH_3)_2$ |
| I.1.580 | $CH_2CF{=}CF_2$ | $CH_2CH(CH_3)_2$ |
| I.1.581 | $CH_2{-}C{\equiv}CH$ | $CH_2CH(CH_3)_2$ |
| I.1.582 | $CH(CH_3){-}C{\equiv}CH$ | $CH_2CH(CH_3)_2$ |
| I.1.583 | OH | $CH_2CH(CH_3)_2$ |
| I.1.584 | $OCH_3$ | $CH_2CH(CH_3)_2$ |
| I.1.585 | $CH_2{-}CO{-}OCH_3$ | $CH_2CH(CH_3)_2$ |
| I.1.586 | $CH_2{-}CH_2{-}CO{-}OCH_3$ | $CH_2CH(CH_3)_2$ |
| I.1.587 | $CH_2{-}CO{-}OC_2H_5$ | $CH_2CH(CH_3)_2$ |
| I.1.588 | $CH(CH_3){-}CO{-}OCH_3$ | $CH_2CH(CH_3)_2$ |
| I.1.589 | $C(CH_3)_2{-}CO{-}OCH_3$ | $CH_2CH(CH_3)_2$ |
| I.1.590 | $CH{=}CH{-}CO{-}OCH_3$ | $CH_2CH(CH_3)_2$ |
| I.1.591 | $C(CH_3)_2{-}CO{-}OCH_2{-}CH{=}CH_2$ | $CH_2CH(CH_3)_2$ |

TABLE 1-continued

I.1

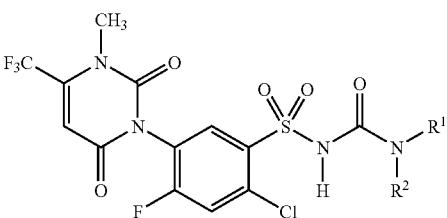

| No. | R$^1$ | R$^2$ |
|---|---|---|
| I.1.592 | CH$_2$CH$_2$OCH$_3$ | CH$_2$CH(CH$_3$)$_2$ |
| I.1.593 | CH$_2$CH$_2$OC$_2$H$_5$ | CH$_2$CH(CH$_3$)$_2$ |
| I.1.594 | CH$_2$CH$_2$SCH$_3$ | CH$_2$CH(CH$_3$)$_2$ |
| I.1.595 | CH$_2$CH$_2$S(O)CH$_3$ | CH$_2$CH(CH$_3$)$_2$ |
| I.1.596 | CH$_2$CH$_2$SO$_2$CH$_3$ | CH$_2$CH(CH$_3$)$_2$ |
| I.1.597 | CH(CH$_3$)C$_2$H$_5$ | CH(CH$_3$)CH$_2$CH$_3$ |
| I.1.598 | CH(CH$_3$)CH$_2$CH$_2$CH$_3$ | CH(CH$_3$)CH$_2$CH$_3$ |
| I.1.599 | CH$_2$CH(CH$_3$)CH$_2$CH$_3$ | CH(CH$_3$)CH$_2$CH$_3$ |
| I.1.600 | CH$_2$CH$_2$CH(CH$_3$)$_2$ | CH(CH$_3$)CH$_2$CH$_3$ |
| I.1.601 | CH$_2$CHF$_2$ | CH(CH$_3$)CH$_2$CH$_3$ |
| I.1.602 | CH$_2$CF$_3$ | CH(CH$_3$)CH$_2$CH$_3$ |
| I.1.603 | CH$_2$CH—Cl | CH(CH$_3$)CH$_2$CH$_3$ |
| I.1.604 | CH$_2$CH$_2$Br | CH(CH$_3$)CH$_2$CH$_3$ |
| I.1.605 | CH$_2$CH$_2$CN | CH(CH$_3$)CH$_2$CH$_3$ |
| I.1.606 | CH(CH$_3$)CN | CH(CH$_3$)CH$_2$CH$_3$ |
| I.1.607 | CH$_2$CH(CH$_3$)CN | CH(CH$_3$)CH$_2$CH$_3$ |
| I.1.608 | cyclopropyl | CH(CH$_3$)CH$_2$CH$_3$ |
| I.1.609 | CH$_2$—cyclopropyl | CH(CH$_3$)CH$_2$CH$_3$ |
| I.1.610 | cyclopentyl | CH(CH$_3$)CH$_2$CH$_3$ |
| I.1.611 | CH$_2$-cyclopentyl | CH(CH$_3$)CH$_2$CH$_3$ |
| I.1.612 | cyclohexyl | CH(CH$_3$)CH$_2$CH$_3$ |
| I.1.613 | CH$_2$CH=CH$_2$ | CH(CH$_3$)CH$_2$CH$_3$ |
| I.1.614 | C(CH$_3$)=CH$_2$ | CH(CH$_3$)CH$_2$CH$_3$ |
| I.1.615 | CH=CHCH$_3$ | CH(CH$_3$)CH$_2$CH$_3$ |
| I.1.616 | CH$_2$CH=CHCH$_3$ | CH(CH$_3$)CH$_2$CH$_3$ |
| I.1.617 | CH$_2$CF=CF$_2$ | CH(CH$_3$)CH$_2$CH$_3$ |
| I.1.618 | CH$_2$—C≡CH | CH(CH$_3$)CH$_2$CH$_3$ |
| I.1.619 | CH(CH$_3$)—C≡CH | CH(CH$_3$)CH$_2$CH$_3$ |
| I.1.620 | OH | CH(CH$_3$)CH$_2$CH$_3$ |
| I.1.621 | OCH$_3$ | CH(CH$_3$)CH$_2$CH$_3$ |
| I.1.622 | CH$_2$—CO—OCH$_3$ | CH(CH$_3$)CH$_2$CH$_3$ |
| I.1.623 | CH$_2$—CH$_2$—CO—OCH$_3$ | CH(CH$_3$)CH$_2$CH$_3$ |
| I.1.624 | CH$_2$—CO—OC$_2$H$_5$ | CH(CH$_3$)CH$_2$CH$_3$ |
| I.1.625 | CH(CH$_3$)—CO—OCH$_3$ | CH(CH$_3$)CH$_2$CH$_3$ |
| I.1.626 | C(CH$_3$)$_2$—CO—OCH$_3$ | CH(CH$_3$)CH$_2$CH$_3$ |
| I.1.627 | CH=CH—CO—OCH$_3$ | CH(CH$_3$)CH$_2$CH$_3$ |
| I.1.628 | C(CH$_3$)$_2$—CO—OCH$_2$—CH=CH$_2$ | CH(CH$_3$)CH$_2$CH$_3$ |
| I.1.629 | CH$_2$CH$_2$OCH$_3$ | CH(CH$_3$)CH$_2$CH$_3$ |
| I.1.630 | CH$_2$CH$_2$OC$_2$H$_5$ | CH(CH$_3$)CH$_2$CH$_3$ |
| I.1.631 | CH$_2$CH$_2$SCH$_3$ | CH(CH$_3$)CH$_2$CH$_3$ |
| I.1.632 | CH$_2$CH$_2$S(O)CH$_3$ | CH(CH$_3$)CH$_2$CH$_3$ |
| I.1.633 | CH$_2$CH$_2$SO$_2$CH$_3$ | CH(CH$_3$)CH$_2$CH$_3$ |
| I.1.634 | CH(CH$_3$)C$_2$H$_5$ | C(CH$_3$)$_3$ |
| I.1.635 | CH$_2$CH(CH$_3$)$_2$ | C(CH$_3$)$_3$ |
| I.1.636 | C(CH$_3$)$_3$ | C(CH$_3$)$_3$ |
| I.1.637 | CH(CH$_3$)CH$_2$CH$_2$CH$_3$ | C(CH$_3$)$_3$ |
| I.1.638 | CH$_2$CH(CH$_3$)CH$_2$CH$_3$ | C(CH$_3$)$_3$ |
| I.1.639 | CH$_2$CH$_2$CH(CH$_3$)$_2$ | C(CH$_3$)$_3$ |
| I.1.640 | CH$_2$CHF$_2$ | C(CH$_3$)$_3$ |
| I.1.641 | CH$_2$CF$_3$ | C(CH$_3$)$_3$ |
| I.1.642 | CH$_2$CH$_2$Cl | C(CH$_3$)$_3$ |
| I.1.643 | CH$_2$CH$_2$Br | C(CH$_3$)$_3$ |
| I.1.644 | CH$_2$CH$_2$CN | C(CH$_3$)$_3$ |
| I.1.645 | CH(CH$_3$)CN | C(CH$_3$)$_3$ |
| I.1.646 | CH$_2$CH(CH$_3$)CN | C(CH$_3$)$_3$ |
| I.1.647 | cyclopropyl | C(CH$_3$)$_3$ |
| I.1.648 | CH$_2$-cyclopropyl | C(CH$_3$)$_3$ |
| I.1.649 | cyclopentyl | C(CH$_3$)$_3$ |
| I.1.650 | CH$_2$-cyclopentyl | C(CH$_3$)$_3$ |
| I.1.651 | cyclohexyl | C(CH$_3$)$_3$ |
| I.1.652 | CH$_2$CH=CH$_2$ | C(CH$_3$)$_3$ |
| I.1.653 | C(CH$_3$)=CH$_2$ | C(CH$_3$)$_3$ |
| I.1.654 | CH=CHCH$_3$ | C(CH$_3$)$_3$ |
| I.1.655 | CH$_2$CH=CHCH$_3$ | C(CH$_3$)$_3$ |

TABLE 1-continued

I.1

[Structure of formula I.1: A pyrimidine-2,4-dione with N-CH3, CF3, substituted on a phenyl ring bearing F, Cl, and a sulfonylurea group -SO2-NH-C(O)-N(R1)(R2)]

| No. | R¹ | R² |
|---|---|---|
| I.1.656 | CH₂CF=CF₂ | C(CH₃)₃ |
| I.1.657 | CH₂—C≡CH | C(CH₃)₃ |
| I.1.658 | CH(CH₃)—C≡CH | C(CH₃)₃ |
| I.1.659 | OH | C(CH₃)₃ |
| I.1.660 | OCH₃ | C(CH₃)₃ |
| I.1.661 | CH₂—CO—OCH₃ | C(CH₃)₃ |
| I.1.662 | CH₂—CH₂—CO—OCH₃ | C(CH₃)₃ |
| I.1.663 | CH₂—CO—OC₂H₅ | C(CH₃)₃ |
| I.1.664 | CH(CH₃)—CO—OCH₃ | C(CH₃)₃ |
| I.1.665 | C(CH₃)₂—CO—OCH₃ | C(CH₃)₃ |
| I.1.666 | CH=CH—CO—OCH₃ | C(CH₃)₃ |
| I.1.667 | C(CH₃)₂—CO—OCH₂—CHCH₂ | C(CH₃)₃ |
| I.1.668 | CH₂CH₂OCH₃ | C(CH₃)₃ |
| I.1.669 | CH₂CH₂OC₂H₅ | C(CH₃)₃ |
| I.1.670 | CH₂CH₂SCH₃ | C(CH₃)₃ |
| I.1.671 | CH₂CH₂S(O)CH₃ | C(CH₃)₃ |
| I.1.672 | CH₂CH₂—SO₂—CH₃ | C(CH₃)₃ |
| I.1.673 | —CH₂—CH₂—CH₂—CH₂— | |
| I.1.674 | —CH₂—CH₂—CH₂—CH₂—CH₂— | |
| I.1.675 | —CH₂—CH₂—CH₂—CH₂—CH(CH₃)— | |
| I.1.676 | —CH₂—CH₂—CH₂—CH(CH₃)—CH₂— | |
| I.1.677 | —CH₂—CH₂—CH(CH₃)—CH₂—CH₂— | |
| I.1.678 | —CH₂—CH₂—CH₂—CH₂—CH(CH₂CH₂Cl)— | |
| I.1.679 | —CH₂—CH₂—CH₂—CH(CH₂CH₂Cl)—CH₂— | |
| I.1.680 | —CH₂—CH₂—CH(CH₂CH₂Cl)—CH₂—CH₂— | |
| I.1.681 | —CH=CH—CH₂—CH₂— | |
| I.1.682 | —CH₂—CH=CH—CH₂— | |
| I.1.683 | —CH=CH—CH₂—CH₂—CH₂— | |
| I.1.684 | CH₂—CH=CH=CH₂—CH₂— | |
| I.1.685 | —CH₂—CH₂—O—CH₂—CH₂— | |
| I.1.686 | —CH₂—CH₂—O—CH(CH₃)—CH₂— | |
| I.1.687 | —CH₂—CH₂—O—CH₂—CH(CH₃)— | |
| I.1.688 | —CH₂—CH(CH₃)—O—CH(CH₃)—CH₂— | |
| I.1.689 | —CH₂—CH₂—N(CH₃)—CH₂—CH₂— | |

Extraordinary preference is also given to the compounds of the formula I.2, in particular to the compounds of the formulae I.2.1 to I.2.689 which differ from the corresponding compounds of the formulae I.1.1 to I.1.689 in that B is oxygen.

Extraordinary preference is also given to the compounds of the formula I.3, in particular to the compounds of the formulae I.3.1 to I.3.689, which differ from the corresponding compounds of the formulae I.1.1 to I.1.689 in that B is sulfur.

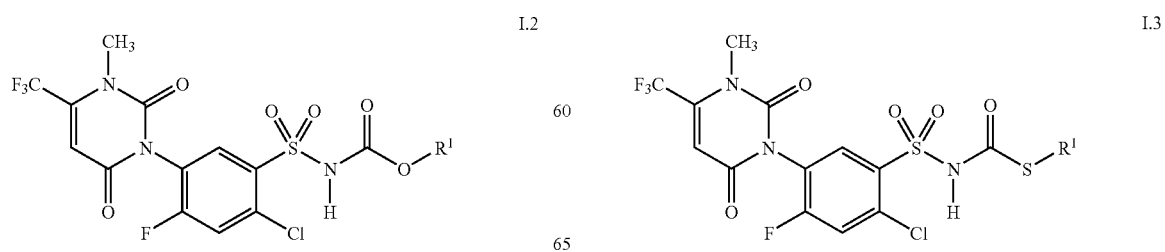

Extraordinary preference is also given to the compounds of the formula I.4, in particular to the compounds of the formulae I.4.1 to I.4.689, which differ from the corresponding compounds of the formulae I.1.1 to I.1.689 in that B is a bond.

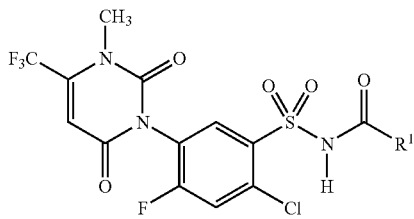

I.4

Extraordinary preference is also given to the compounds of the formula I.5, in particular to the compounds of the formulae I.5.1 to I.5.689, which differ from the corresponding compounds of the formulae I.1.1 to I.1.689 in that Y is $SO_2$.

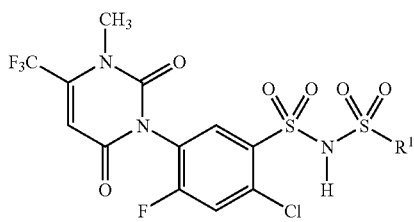

I.5

Extraordinary preference is also given to the compounds of the formula I.6, in particular to the compounds of the formulae I.6.1 to I.6.689, which differ from the corresponding compounds of the formulae I.1.1 to I.1.689 in that Y is $SO_2NR^2$.

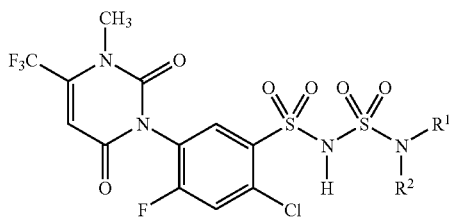

I.6

Extraordinary preference is also given to the compounds of the formula I.7, in particular to the compounds of the formulae I.7.1 to I.7.689, which differ from the corresponding compounds of the formulae I.1.1 to I.1.689 in that $R^{29}$ is amino.

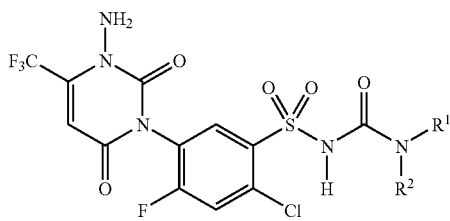

I.7

Extraordinary preference is also given to the compounds of the formula I.8, in particular to the compounds of the formulae I.8.1 to I.8.689, which differ from the corresponding compounds of the formulae I.1.1 to I.1.689 in that B is oxygen and $R^{29}$ is amino.

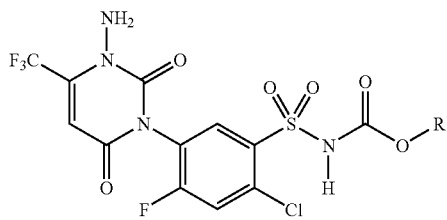

I.8

Extraordinary preference is also given to the compounds of the formula I.9, in particular to the compounds of the formulae I.9.1 to I.9.689, which differ from the corresponding compounds of the formulae I.1.1 to I.1.689 in that B is sulfur and $R^{29}$ is amino.

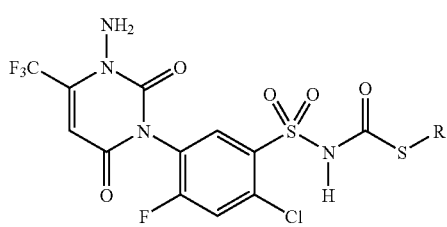

I.9

Extraordinary preference is also given to the compounds of the formula I.10, in particular to the compounds of the formulae I.10.1 to I.10.689, which differ from the corresponding compounds of the formulae I.1.1 to I.1.689 in that B is a bond and $R^{29}$ is amino.

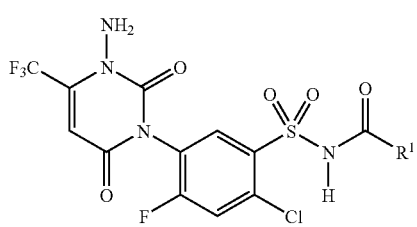

I.10

Extraordinary preference is also given to the compounds of the formula I.11, in particular to the compounds of the formulae I.11.1 to I.11.689, which differ from the corresponding compounds of the formulae I.1.1 to I.1.689 in that Y is $SO_2$ and $R^{29}$ is amino.

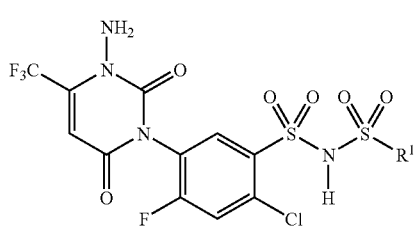

I.11

Extraordinary preference is also given to the compounds of the formula I.12, in particular to the compounds of the formulae I.12.1 to I.12.689, which differ from the corresponding compounds of the formulae I.1.1 to I.1.689 in that Y is $SO_2NR^2$ and $R^{29}$ is amino.

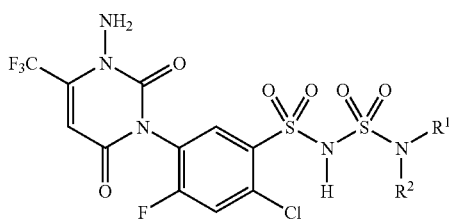

I.12

Extraordinary preference is also given to the compounds of the formula I.13, in particular to the compounds of the formulae I.13.1 to I.13.689, which differ from the corresponding compounds of the formulae I.1.1 to I.1.689 in that $X^1$ is hydrogen.

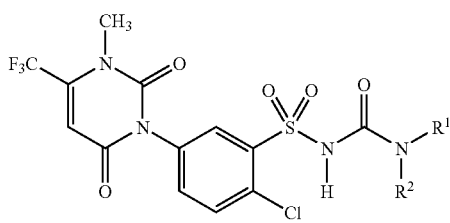

I.13

Extraordinary preference is also given to the compounds of the formula I.14, in particular to the compounds of the formulae I.14.1 to I.14.689, which differ from the corresponding compounds of the formulae I.1.1 to I.1.689 in that $X^1$ is hydrogen and B is oxygen.

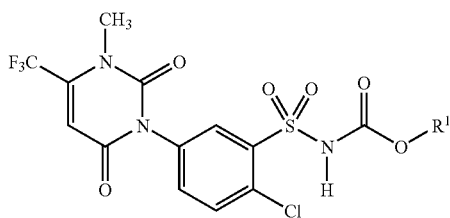

I.14

Extraordinary preference is also given to the compounds of the formula I.15, in particular to the compounds of the formulae I.15.1 to I.15.689, which differ from the corresponding compounds of the formulae I.1.1 to I.1.689 in that $X^1$ is hydrogen and B is sulfur.

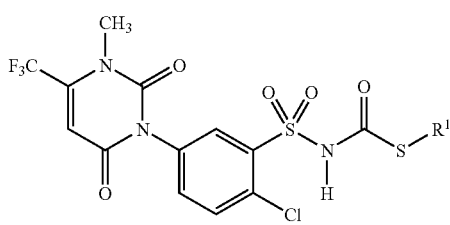

I.15

Extraordinary preference is also given to the compounds of the formula I.16, in particular to the compounds of the formulae I.16.1 to I.16.689, which differ from the corresponding compounds of the formulae I.1.1 to I.1.689 in that $X^1$ is hydrogen and B is a bond.

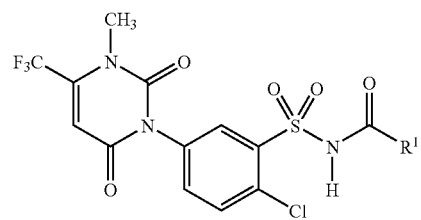

I.16

Extraordinary preference is also given to the compounds of the formula I.17, in particular to the compounds of the formulae I.17.1 to I.17.689, which differ from the corresponding compounds of the formulae I.1.1 to I.1.689 in that $X^1$ is hydrogen and Y is $SO_2$.

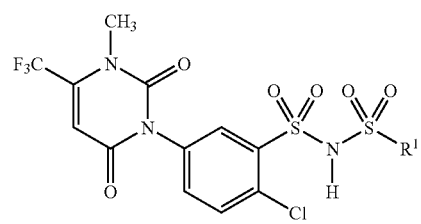

I.17

Extraordinary preference is also given to the compounds of the formula I.18, in particular to the compounds of the formulae I.18.1 to I.18.689, which differ from the corresponding compounds of the formulae I.1.1 to I.1.689 in that $X^1$ is hydrogen and Y is $SO_2NR^2$.

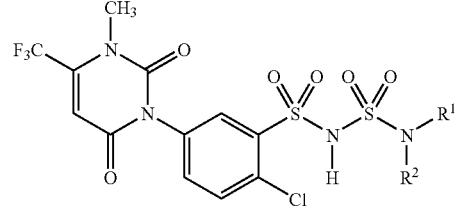

I.18

Extraordinary preference is also given to the compounds of the formula I.19, in particular to the compounds of the formulae I.19.1 to I.19.689, which differ from the corresponding compounds of the formulae I.1.1 to I.1.689 in that $X^1$ is hydrogen and $R^{29}$ is amino.

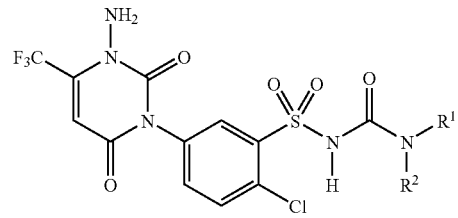

I.19

Extraordinary preference is also given to the compounds of the formula I.20, in particular to the compounds of the formulae I.20.1 to I.20.689, which differ from the corresponding compounds of the formulae I.1.1 to I.1.689 in that $X^1$ is hydrogen, B is oxygen and $R^{29}$ is amino.

I.20
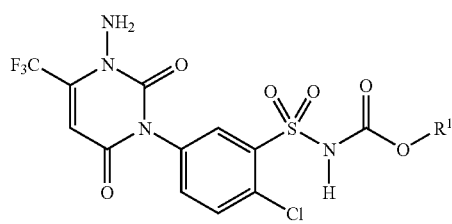

Extraordinary preference is also given to the compounds of the formula I.21, in particular to the compounds of the formulae I.21.1 to I.21.689, which differ from the corresponding compounds of the formulae I.1.1 to I.1.689 in that $X^1$ is hydrogen, B is sulfur and $R^{29}$ is amino.

I.21
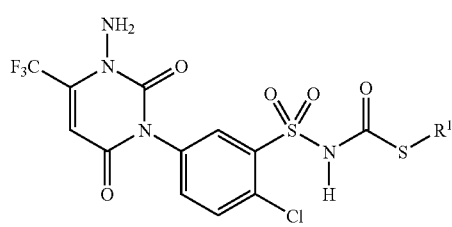

Extraordinary preference is also given to the compounds of the formula I.22, in particular to the compounds of the formulae I.22.1 to I.22.689, which differ from the corresponding compounds of the formulae I.1.1 to I.1.689 in that $X^1$ is hydrogen, B is a bond and $R^{29}$ is amino.

I.22
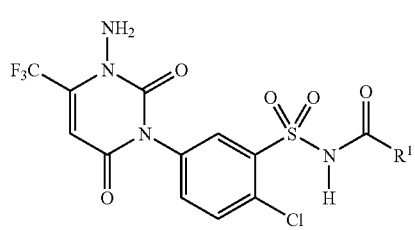

Extraordinary preference is also given to the compounds of the formula I.23, in particular to the compounds of the formulae I.23.1 to I.23.689, which differ from the corresponding compounds of the formulae I.1.1 to I.1.689 in that $X^1$ is hydrogen, Y is $SO_2$ and $R^{29}$ is amino.

I.23
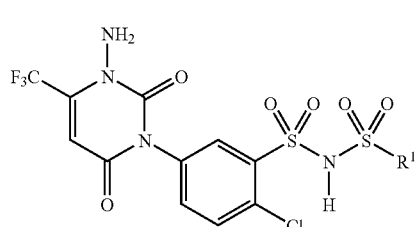

Extraordinary preference is also given to the compounds of the formula I.24, in particular to the compounds of the formulae I.24.1 to I.24.689, which differ from the corresponding compounds of the formulae I.1.1 to I.1.689 in that $X^1$ is hydrogen, Y is $SO_2NR^2$ and $R^{29}$ is amino.

I.24
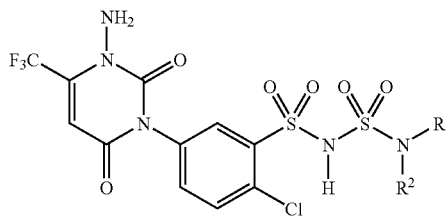

Extraordinary preference is also given to the compounds of the formula I.25, in particular to the compounds of the formulae I.25.1 to I.25.689, which differ from the corresponding compounds of the formulae I.1.1 to I.1.689 in that Q is $Q^5$ (where $A^1$=oxygen, $R^7$=difluoromethyl and $R^8$=methyl).

I.25
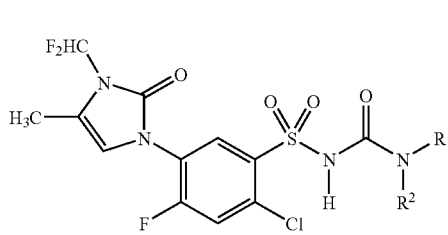

Extraordinary preference is also given to the compounds of the formula I.26, in particular to the compounds of the formulae I.26.1 to I.26.689, which differ from the corresponding compounds of the formulae I.1.1 to I.1.689 in that B is oxygen and Q is $Q^5$ (where $A^1$=oxygen, $R^7$=difluoromethyl and $R^8$=methyl).

I.26
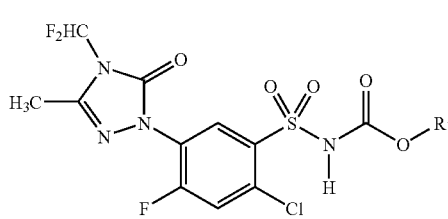

Extraordinary preference is also given to the compounds of the formula I.27, in particular to the compounds of the formulae I.27.1 to I.27.689, which differ from the corresponding compounds of the formulae I.1.1 to I.1.689 in that B is sulfur and Q is $Q^5$ (where $A^1$=oxygen, $R^7$=difluoromethyl and $R^8$=methyl).

I.27
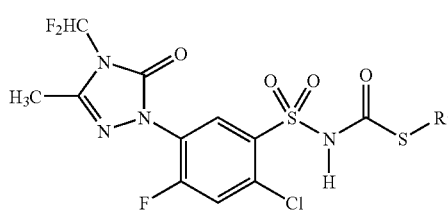

Extraordinary preference is also given to the compounds of the formula I.28, in particular to the compounds of the formulae I.28.1 to I.28.689, which differ from the corresponding compounds of the formulae I.1.1 to I.1.689 in that B is a bond and Q is $Q^5$ (where $A^1$=oxygen, $R^7$=difluoromethyl and $R^8$=methyl).

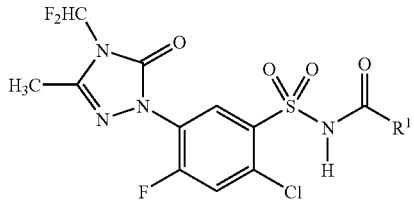

I.28

Extraordinary preference is also given to the compounds of the formula I.29, in particular to the compounds of the formulae I.29.1 to I.29.689, which differ from the corresponding compounds of the formulae I.1.1 to I.1.689 in that Y is $SO_2$ and Q is $Q^5$ (where $A^1$=oxygen, $R^7$=difluoromethyl and $R^8$=methyl).

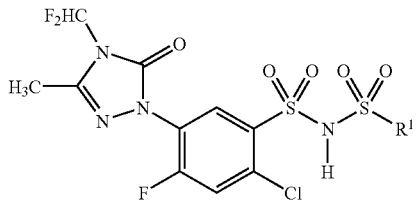

I.29

Extraordinary preference is also given to the compounds of the formula I.30, in particular to the compounds of the formulae I.30.1 to I.30.689, which differ from the corresponding compounds of the formulae I.1.1 to I.1.689 in that Y is $SO_2NR^2$ and Q is $Q^5$ (where $A^1$=oxygen, $R^7$=difluoromethyl and $R^8$=methyl).

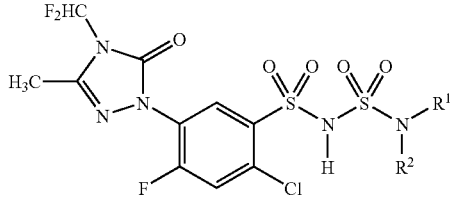

I.30

Extraordinary preference is also given to the compounds of the formula I.31, in particular to the compounds of the formulae I.31.1 to I.31.689, which differ from the corresponding compounds of the formulae I.1.1 to I.1.689 in that $X^1$ is chlorine and Q is $Q^5$ (where $A^1$=oxygen, $R^7$=difluoromethyl and $R^8$=methyl).

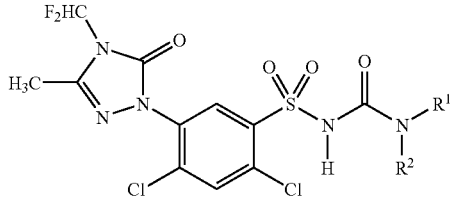

I.31

Extraordinary preference is also given to the compounds of the formula I.32, in particular to the compounds of the formulae I.32.1 to I.32.689, which differ from the corresponding compounds of the formulae I.1.1 to I.1.689 in that $X^1$ is chlorine, B is oxygen and Q is $Q^5$ (where $A^1$=oxygen, $R^7$=difluoromethyl and $R^8$=methyl).

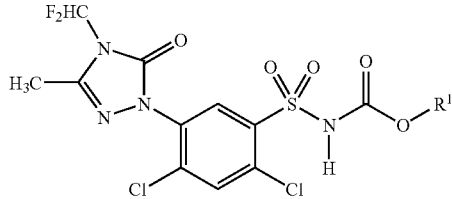

I.32

Extraordinary preference is also given to the compounds of the formula I.33, in particular to the compounds of the formulae I.33.1 to I.33.689, which differ from the corresponding compounds of the formulae I.1.1 to I.1.689 in that $X^1$ is chlorine, B is sulfur and Q is $Q^5$ (where $A^1$=oxygen, $R^7$=difluoromethyl and $R^8$=methyl).

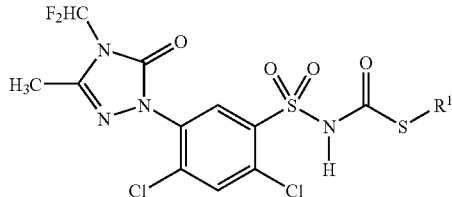

I.33

Extraordinary preference is also given to the compounds of the formula I.34, in particular to the compounds of the formulae I.34.1 to I.34.689, which differ from the corresponding compounds of the formulae I.1.1 to I.1.689 in that $X^1$ is chlorine, B is a bond and Q is $Q^5$ (where $A^1$=oxygen, $R^7$=difluoromethyl and $R^8$=methyl).

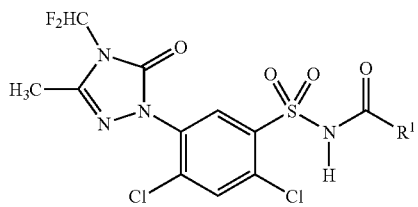

I.34

Extraordinary preference is also given to the compounds of the formula I.35, in particular to the compounds of the formulae I.35.1 to I.35.689, which differ from the corresponding compounds of the formulae I.1.1 to I.1.689 in that $X^1$ is chlorine, Y is $SO_2$ and Q is $Q^5$ (where $A^1$=oxygen, $R^7$=difluoromethyl and $R^8$=methyl).

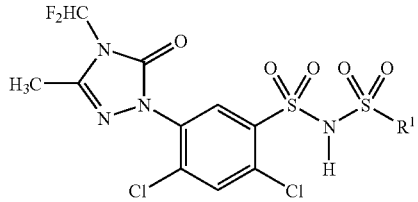

I.35

Extraordinary preference is also given to the compounds of the formula I.36, in particular to the compounds of the formulae I.36.1 to I.36.689, which differ from the corresponding compounds of the formulae I.1.1 to I.1.689 in that $X^1$ is chlorine, Y is $SO_2NR^2$ and Q is $Q^5$ (where $A^1$=oxygen, $R^7$=difluoromethyl and $R^8$=methyl).

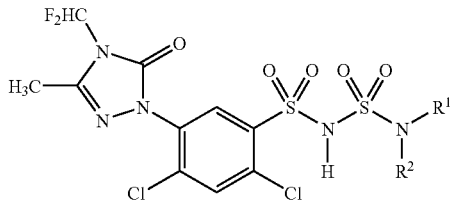

I.36

Extraordinary preference is also given to the compounds of the formula I.37, in particular to the compounds of the formulae I.37.1 to I.37.689, which differ from the corresponding compounds of the formulae I.1.1 to I.1.689 in that Q is $Q^{22}$ (where $A^{10}$ and $A^{11}$=oxygen, $A^{12}$=sulfur and $R^{32}$, $R^{33}$=methyl).

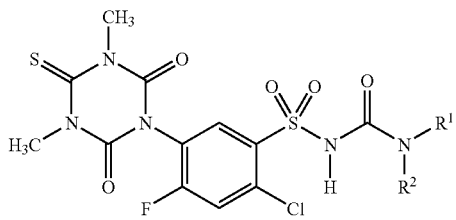

I.37

Extraordinary preference is also given to the compounds of the formula I.38, in particular to the compounds of the formulae I.38.1 to I.38.689, which differ from the corresponding compounds of the formulae I.1.1 to I.1.689 in that B is oxygen and Q is $Q^{22}$ (where $A^{10}$ and $A^{11}$=oxygen, $A^{12}$=sulfur and $R^{32}$, $R^{33}$=methyl).

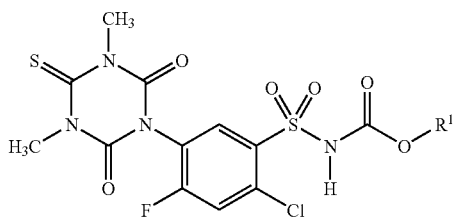

I.38

Extraordinary preference is also given to the compounds of the formula I.39, in particular to the compounds of the formulae I.39.1 to I.39.689, which differ from the corresponding compounds of the formulae I.1.1 to I.1.689 in that B is sulfur and Q is $Q^{22}$ (where $A^{10}$ and $A^{11}$=oxygen, $A^{12}$=sulfur and $R^{32}$, $R^{33}$=methyl).

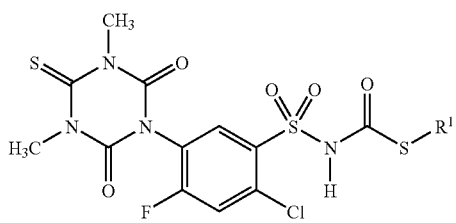

I.39

Extraordinary preference is also given to the compounds of the formula I.40, in particular to the compounds of the formulae I.40.1 to I.40.689, which differ from the corresponding compounds of the formulae I.1.1 to I.1.689 in that B is a bond and Q is $Q^{22}$ (where $A^{10}$ and $A^{11}$=oxygen, $A^{12}$=sulfur and $R^{32}$, $R^{33}$=methyl).

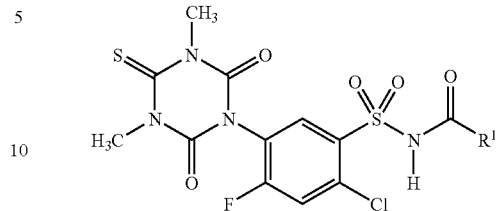

I.40

Extraordinary preference is also given to the compounds of the formula I.41, in particular to the compounds of the formulae I.41.1 to I.41.689, which differ from the corresponding compounds of the formulae I.1.1 to I.1.689 in that Y is $SO_2$ and Q is $Q^{22}$ (where $A^{10}$ and $A^{11}$=oxygen, $A^{12}$=sulfur and $R^{32}$, $R^{33}$=methyl).

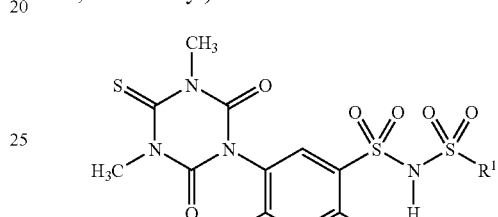

I.41

Extraordinary preference is also given to the compounds of the formula I.42, in particular to the compounds of the formulae I.42.1 to I.42.689, which differ from the corresponding compounds of the formulae I.1.1 to I.1.689 in that Y is $SO_2NR^2$ and Q is $Q^{22}$ (where $A^{10}$ and $A^{11}$=oxygen, $A^{12}$=sulfur and $R^{32}$, $R^{33}$=methyl).

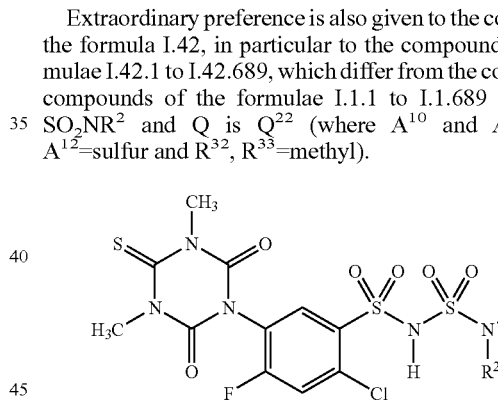

I.42

Extraordinary preference is also given to the compounds of the formula I.43, in particular to the compounds of the formulae I.43.1 to I.43.689, which differ from the corresponding compounds of the formulae I.1.1 to I.1.689 in that Q is $Q^{22}$ (where $A^{10}$, $A^{11}$, $A^{12}$=oxygen and $R^{32}$, $R^{33}$=methyl).

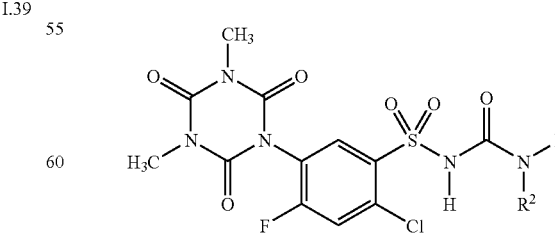

I.43

Extraordinary preference is also given to the compounds of the formula I.44, in particular to the compounds of the formulae I.44.1 to I.44.689, which differ from the corresponding compounds of the formulae I.1.1 to I.1.689 in that B is oxygen and Q is $Q^{22}$ (where $A^{10}$, $A^{11}$, $A^{12}$=oxygen and $R^{32}$, $R^{33}$=methyl).

I.44

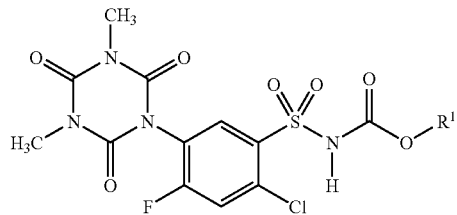

Extraordinary preference is also given to the compounds of the formula I.45, in particular to the compounds of the formulae I.45.1 to I.45.689, which differ from the corresponding compounds of the formulae I.1.1 to I.1.689 in that B is sulfur and Q is $Q^{22}$ (where $A^{10}$, $A^{11}$, $A^{12}$=oxygen and $R^{32}$, $R^{33}$=methyl).

I.45

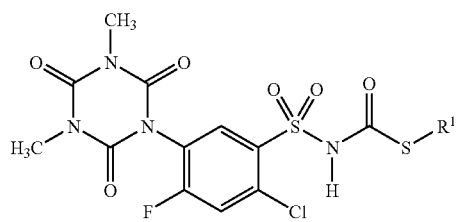

Extraordinary preference is also given to the compounds of the formula I.46, in particular to the compounds of the formulae I.46.1 to I.46.689, which differ from the corresponding compounds of the formulae I.1.1 to I.1.689 in that B is a bond and Q is $Q^{22}$ (where $A^{10}$, $A^{11}$, $A^{12}$=oxygen and $R^{32}$, $R^{33}$=methyl).

I.46

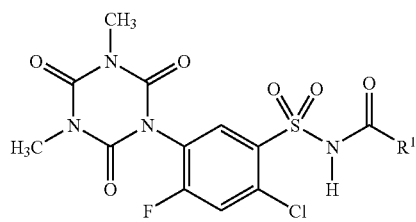

Extraordinary preference is also given to the compounds of the formula I.47, in particular to the compounds of the formulae I.47.1 to I.47.689, which differ from the corresponding compounds of the formulae I.1.1 to I.1.689 in that Y is $SO_2$ and Q is $Q^{22}$ (where $A^{10}$, $A^{11}$, $A^{12}$=oxygen and $R^{32}$, $R^{33}$=methyl).

I.47

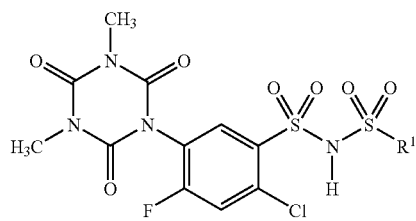

Extraordinary preference is also given to the compounds of the formula I.48, in particular to the compounds of the formulae I.48.1 to I.48.689, which differ from the corresponding compounds of the formulae I.1.1 to I.1.689 in that Y is $SO_2NR^2$ and Q is $Q^{22}$ (where $A^{10}$, $A^{11}$, $A^{12}$=oxygen and $R^{32}$, $R^{33}$=methyl).

I.48

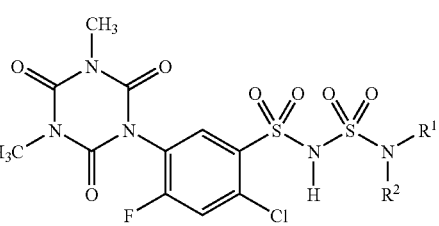

Extraordinary preference is also given to the compounds of the formula I.49, in particular to the compounds of the formulae I.49.1 to I.49.689, which differ from the corresponding compounds of the formulae I.1.1 to I.1.689 in that Q is $Q^{27}$ (where $A^{13}$=oxygen, $R^{34}$, $R^{36}$=hydrogen, $R^{35}$=trifluoromethyl).

I.49

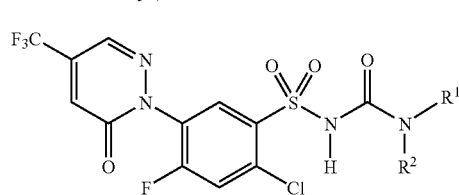

Extraordinary preference is also given to the compounds of the formula I.50, in particular to the compounds of the formulae I.50.1 to I.50.689, which differ from the corresponding compounds of the formulae I.1.1 to I.1.689 in that B is oxygen and Q is $Q^{27}$ (where $A^{13}$=oxygen, $R^{34}$, $R^{36}$=hydrogen, $R^{35}$=trifluoromethyl).

I.50

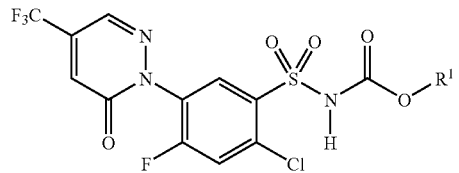

Extraordinary preference is also given to the compounds of the formula I.51, in particular to the compounds of the formulae I.51.1 to I.51.689, which differ from the corresponding compounds of the formulae I.1.1 to I.1.689 in that B is sulfur and Q is $Q^{27}$ (where $A^{13}$=oxygen, $R^{34}$, $R^{36}$=hydrogen, $R^{35}$=trifluoromethyl).

I.51

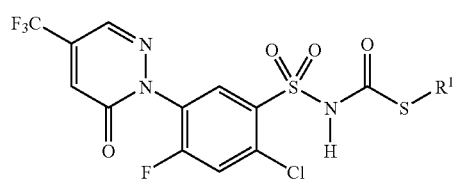

Extraordinary preference is also given to the compounds of the formula I.52, in particular to the compounds of the formulae I.52.1 to I.52.689, which differ from the corresponding compounds of the formulae I.1.1 to I.1.689 in that B is a bond and Q is Q (where $A^{13}$=oxygen, $R^{34}$, $R^{36}$=hydrogen, $R^{35}$=trifluoromethyl).

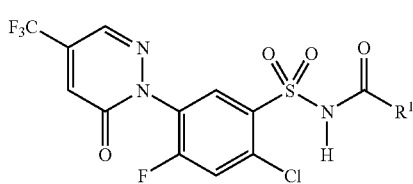

I.52

Extraordinary preference is also given to the compounds of the formula I.53, in particular to the compounds of the formulae I.53.1 to I.53.689, which differ from the corresponding compounds of the formulae I.1.1 to I.1.689 in that Y is $SO_2$ and Q is $Q^{27}$ (where $A^{13}$=oxygen, $R^{34}$, $R^{36}$=hydrogen, $R^{35}$=trifluoromethyl).

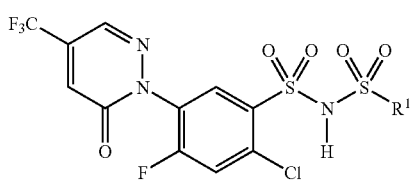

I.53

Extraordinary preference is also given to the compounds of the formula I.54, in particular to the compounds of the formulae I.54.1 to I.54.689, which differ from the corresponding compounds of the formulae I.1.1 to I.1.689 in that Y is $SO_2NR^2$ and Q is $Q^{27}$ (where $A^{13}$=oxygen, $R^{34}$, $R^{36}$=hydrogen, $R^{35}$=trifluoromethyl).

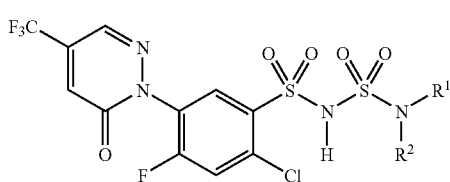

I.54

Extraordinary preference is also given to the compounds of the formula I.55, in particular to the compounds of the formulae I.55.1 to I.55.689, which differ from the corresponding compounds of the formulae I.1.1 to I.1.689 in that Q is $Q^{27}$ (where $A^{13}$=oxygen, $R^{34}$=hydrogen, $R^{35}$=trifluoromethyl, $R^{36}$=methyl).

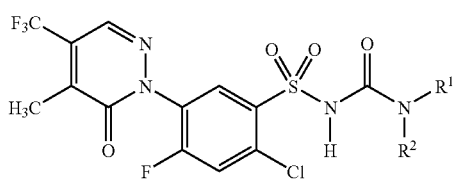

I.55

Extraordinary preference is also given to the compounds of the formula I.56, in particular to the compounds of the formulae I.56.1 to I.56.689, which differ from the corresponding compounds of the formulae I.1.1 to I.1.689 in that B is oxygen and Q is $Q^{27}$ (where $A^{13}$=oxygen, $R^{34}$=hydrogen, $R^{35}$=trifluoromethyl, $R^{36}$=methyl).

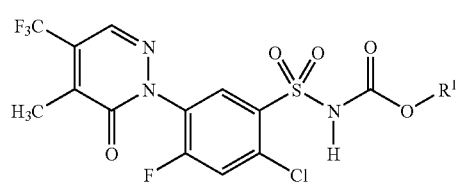

I.56

Extraordinary preference is also given to the compounds of the formula I.57, in particular to the compounds of the formulae I.57.1 to I.57.689, which differ from the corresponding compounds of the formulae I.1.1 to I.1.689 in that B is sulfur and Q is $Q^{27}$ (where $A^{13}$=oxygen, $R^{34}$=hydrogen, $R^{35}$=trifluoromethyl, $R^{36}$=methyl).

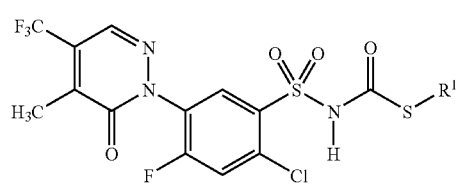

I.57

Extraordinary preference is also given to the compounds of the formula I.58, in particular to the compounds of the formulae I.58.1 to I.58.689, which differ from the corresponding compounds of the formulae I.1.1 to I.1.689 in that B is a bond and Q is $Q^{27}$ (where $A^{13}$=oxygen, $R^{34}$=hydrogen, $R^{35}$=trifluoromethyl, $R^{36}$=methyl).

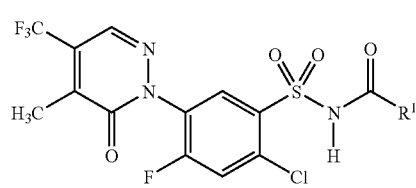

I.58

Extraordinary preference is also given to the compounds of the formula I.59, in particular to the compounds of the formulae I.59.1 to I.59.689, which differ from the corresponding compounds of the formulae I.1.1 to I.1.689 in that Y is $SO_2$ and Q is $Q^{27}$ (where $A^{13}$=oxygen, $R^{34}$=hydrogen, $R^{35}$=trifluoromethyl, $R^{36}$=methyl).

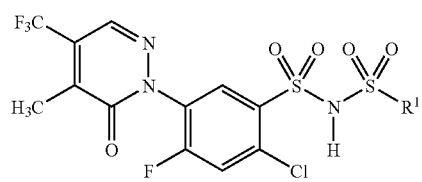

I.59

Extraordinary preference is also given to the compounds of the formula I.60, in particular to the compounds of the formulae I.60.1 to I.60.689, which differ from the corresponding compounds of the formulae I.1.1 to I.1.689 in that Y is SO$_2$NR$^2$ and Q is Q$^{27}$ (where A$^{13}$=oxygen, R$^{34}$=hydrogen, R$^{35}$=trifluoromethyl, R$^{36}$=methyl).

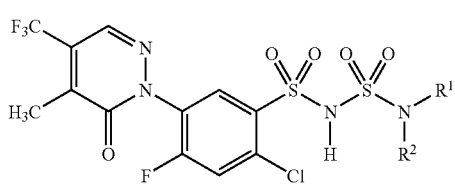

I.60

Extraordinary preference is also given to the compounds of the formula I.61, in particular to the compounds of the formulae I.61.1 to I.61.689, which differ from the corresponding compounds of the formulae I.1.1 to I.1.689 in that Y is SO$_2$NR$^2$ and Q is Q$^{27}$ (where A$^{13}$=oxygen, R$^{34}$=hydrogen, R$^{35}$=methylsulfonyl, R$^{36}$=amino).

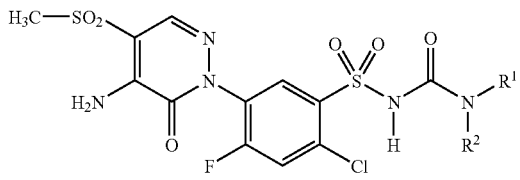

I.61

Extraordinary preference is also given to the compounds of the formula I.62, in particular to the compounds of the formulae I.62.1 to I.62.689, which differ from the corresponding compounds of the formulae I.1.1 to I.1.689 in that B is oxygen and Q is Q$^{27}$ (where A$^{13}$=oxygen, R$^{34}$=hydrogen, R$^{35}$=methylsulfonyl, R$^{36}$=amino).

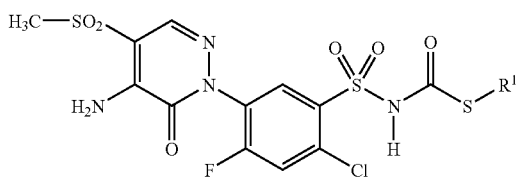

I.62

Extraordinary preference is also given to the compounds of the formula I.63, in particular to the compounds of the formulae I.63.1 to I.63.689, which differ from the corresponding compounds of the formulae I.1.1 to I.1.689 in that B is sulfur and Q is Q$^{27}$ (where A$^{13}$=oxygen, R$^{34}$=hydrogen, R$^{35}$=methylsulfonyl, R$^{36}$=amino).

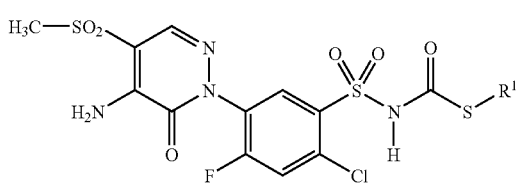

I.63

Extraordinary preference is also given to the compounds of the formula I.64, in particular to the compounds of the formulae I.64.1 to I.64.689, which differ from the corresponding compounds of the formulae I.1.1 to I.1.689 in that B is a bond and Q is Q$^{27}$ (where A$^{13}$=oxygen, R$^{34}$=hydrogen, R$^{35}$=methylsulfonyl, R$^{36}$=amino).

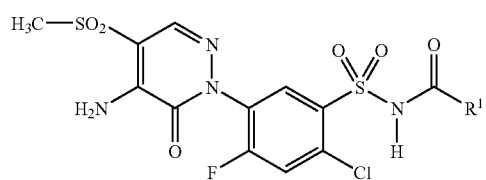

I.64

Extraordinary preference is also given to the compounds of the formula I.65, in particular to the compounds of the formulae I.65.1 to I.65.689, which differ from the corresponding compounds of the formulae I.1.1 to I.1.689 in that Y is SO$_2$ and Q is Q$^{27}$ (where A$^{13}$=oxygen, R$^{34}$=hydrogen, R$^{35}$=methylsulfonyl, R$^{36}$=amino).

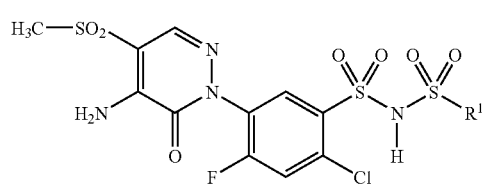

I.65

Extraordinary preference is also given to the compounds of the formula I.66, in particular to the compounds of the formulae I.66.1 to I.66.689, which differ from the corresponding compounds of the formulae I.1.1 to I.1.689 in that Y is SO$_2$NR$^2$ and Q is Q$^{27}$ (where A$^{13}$=oxygen, R$^{34}$=hydrogen, R$^{35}$=methylsulfonyl, R$^{36}$=amino).

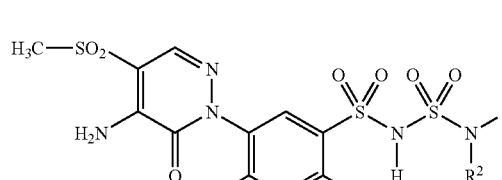

I.66

Extraordinary preference is also given to the compounds of the formula I.67, in particular to the compounds of the formulae I.67.1 to I.67.689, which differ from the corresponding compounds of the formulae I.1.1 to I.1.689 in that Q is Q$^{32}$ (where R$^{37}$=chlorine, R$^{38}$=difluoromethoxy, R$^{39}$=methyl).

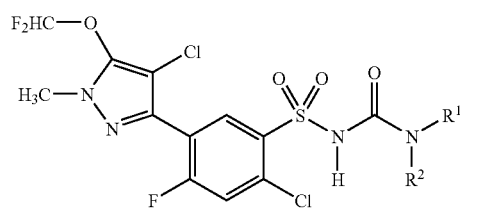

I.67

Extraordinary preference is also given to the compounds of the formula I.68, in particular to the compounds of the formulae I.68.1 to I.68.689, which differ from the corresponding compounds of the formulae I.1.1 to I.1.689 in that B is oxygen and Q is $Q^{32}$ (where $R^{37}$=chlorine, $R^{38}$=difluoromethoxy, $R^{39}$=methyl).

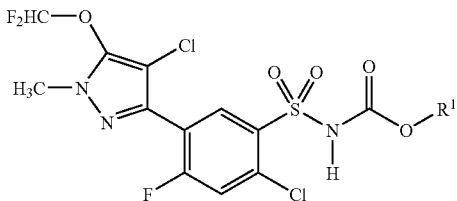

I.68

Extraordinary preference is also given to the compounds of the formula I.69, in particular to the compounds of the formulae I.69.1 to I.69.689, which differ from the corresponding compounds of the formulae I.1.1 to I.1.689 in that B is sulfur and Q is $Q^{32}$ (where $R^{37}$=chlorine, $R^{38}$=difluoromethoxy, $R^{39}$=methyl).

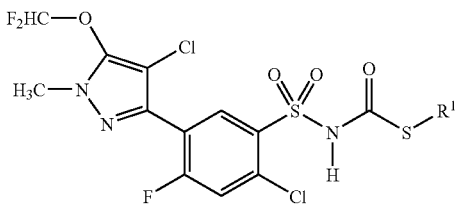

I.69

Extraordinary preference is also given to the compounds of the formula I.70, in particular to the compounds of the formulae I.70.1 to I.70.689, which differ from the corresponding compounds of the formulae I.1.1 to I.1.689 in that B is a bond and Q is $Q^{32}$ (where $R^{37}$=chlorine, $R^{38}$=difluoromethoxy, $R^{39}$=methyl).

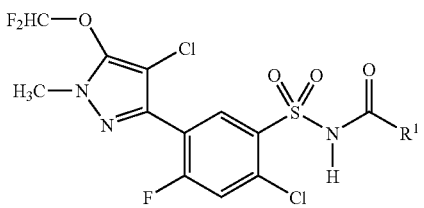

I.70

Extraordinary preference is also given to the compounds of the formula I.71, in particular to the compounds of the formulae I.71.1 to I.71.689, which differ from the corresponding compounds of the formulae I.1.1 to I.1.689 in that Y is $SO_2$ and Q is $Q^{32}$ (where $R^{37}$=chlorine, $R^{38}$=difluoromethoxy, $R^{39}$=methyl).

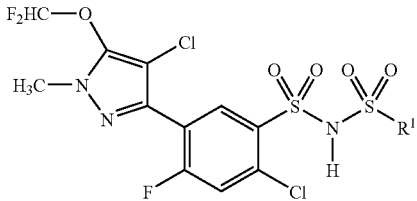

I.71

Extraordinary preference is also given to the compounds of the formula I.72, in particular to the compounds of the formulae I.72.1 to I.72.689, which differ from the corresponding compounds of the formulae I.1.1 to I.1.689 in that Y is $SO_2NR^2$ and Q is $Q^{32}$ (where $R^{37}$=chlorine, $R^{38}$=difluoromethoxy, $R^{39}$=methyl).

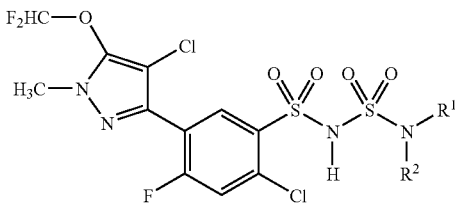

I.72

Extraordinary preference is also given to the compounds of the formula I.73, in particular to the compounds of the formulae I.73.1 to I.73.689, which differ from the corresponding compounds of the formulae I.1.1 to I.1.689 in that Q is $Q^{32}$ (where $R^{37}$=bromine, $R^{38}$=difluoromethoxy, $R^{39}$=methyl).

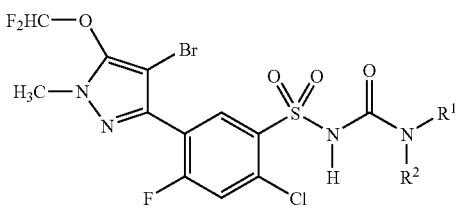

I.73

Extraordinary preference is also given to the compounds of the formula I.74, in particular to the compounds of the formulae I.74.1 to I.74.689, which differ from the corresponding compounds of the formulae I.1.1 to I.1.689 in that B is oxygen and Q is $Q^{32}$ (where $R^{37}$=bromine, $R^{38}$=difluoromethoxy, $R^{39}$=methyl).

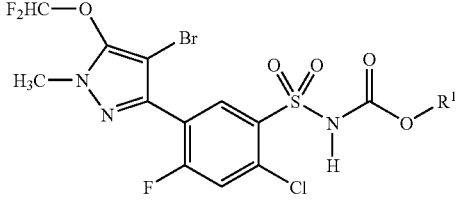

I.74

Extraordinary preference is also given to the compounds of the formula I.75, in particular to the compounds of the formulae I.75.1 to I.75.689, which differ from the corresponding compounds of the formulae I.1.1 to I.1.689 in that B is sulfur and Q is $Q^{32}$ (where $R^{37}$=bromine, $R^{38}$=difluoromethoxy, $R^{39}$=methyl).

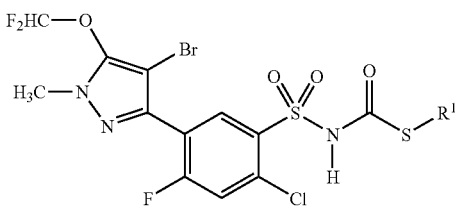

I.75

Extraordinary preference is also given to the compounds of the formula I.76, in particular to the compounds of the formulae I.76.1 to I.76.689, which differ from the corresponding compounds of the formulae I.1.1 to I.1.689 in that B is a bond and Q is $Q^{32}$ (where $R^{37}$=bromine, $R^{38}$=difluoromethoxy, $R^{39}$=methyl).

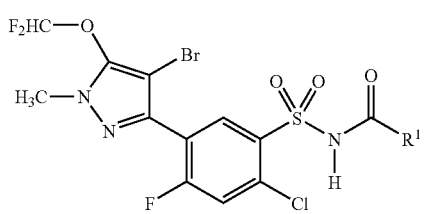
I.76

Extraordinary preference is also given to the compounds of the formula I.77, in particular to the compounds of the formulae I.77.1 to I.77.689, which differ from the corresponding compounds of the formulae I.1.1 to I.1.689 in that Y is $SO_2$ and Q is $Q^{32}$ (where $R^{37}$=bromine, $R^{38}$=difluoromethoxy, $R^{39}$=methyl).

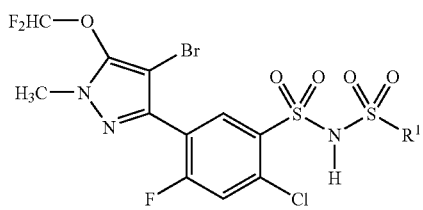
I.77

Extraordinary preference is also given to the compounds of the formula I.78, in particular to the compounds of the formulae I.78.1 to I.78.689, which differ from the corresponding compounds of the formulae I.1.1 to I.1.689 in that Y is $SO_2NR^2$ and Q is $Q^{32}$ (where $R^{37}$=bromine, $R^{38}$=difluoromethoxy, $R^{39}$=methyl).

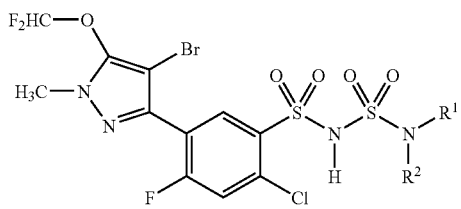
I.78

Extraordinary preference is also given to the compounds of the formula I.79, in particular to the compounds of the formulae I.79.1 to I.79.689, which differ from the corresponding compounds of the formulae I.1.1 to I.1.689 in that $X^1$ is chlorine and Q is $Q^{32}$ (where $R^{37}$=bromine, $R^{38}$=difluoromethoxy, $R^{39}$=methyl).

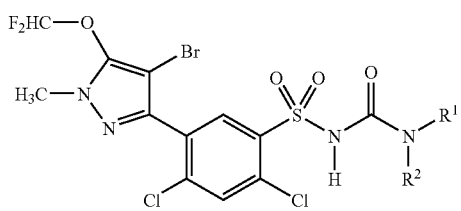
I.79

Extraordinary preference is also given to the compounds of the formula I.80, in particular to the compounds of the formulae I.80.1 to I.80.689, which differ from the corresponding compounds of the formulae I.1.1 to I.1.689 in that $X^1$ is chlorine, B is oxygen and Q is $Q^{32}$ (where $R^{37}$=bromine, $R^{38}$=difluoromethoxy, $R^{39}$=methyl).

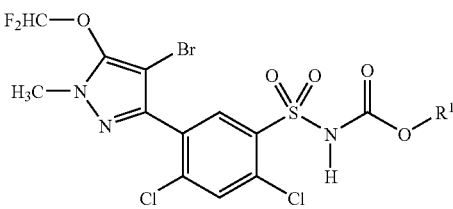
I.80

Extraordinary preference is also given to the compounds of the formula I.81, in particular to the compounds of the formulae I.81.1 to I.81.689, which differ from the corresponding compounds of the formulae I.1.1 to I.1.689 in that $X^1$ is chlorine, B is sulfur and Q is $Q^{32}$ (where $R^{37}$=bromine, $R^{38}$=difluoromethoxy, $R^{39}$=methyl).

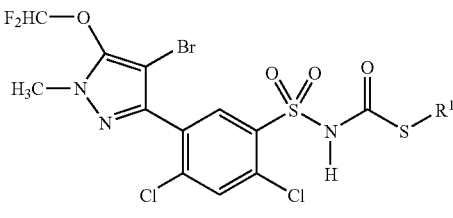
I.81

Extraordinary preference is also given to the compounds of the formula I.82, in particular to the compounds of the formulae I.82.1 to I.82.689, which differ from the corresponding compounds of the formulae I.1.1 to I.1.689 in that $X^1$ is chlorine, B is a bond and Q is $Q^{32}$ (where $R^{31}$=bromine, $R^{38}$=difluoromethoxy, $R^{39}$=methyl).

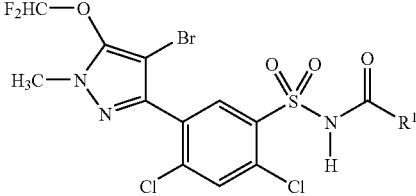
I.82

Extraordinary preference is also given to the compounds of the formula I.83, in particular to the compounds of the formulae I.83.1 to I.83.689, which differ from the corresponding compounds of the formulae I.1.1 to I.1.689 in that $X^1$ is chlorine, Y is $SO_2$ and Q is $Q^{32}$ (where $R^{37}$=bromine, $R^{38}$=difluoromethoxy, $R^{39}$=methyl).

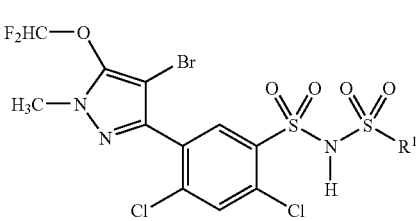
I.83

Extraordinary preference is also given to the compounds of the formula I.84, in particular to the compounds of the formulae I.84.1 to I.84.689, which differ from the corresponding compounds of the formulae I.1.1 to I.1.689 in that $X^1$ is chlorine, Y is $SO_2NR^2$ and Q is $Q^{32}$ (where $R^{37}$=bromine, $R^{38}$=difluoromethoxy, $R^{39}$=methyl).

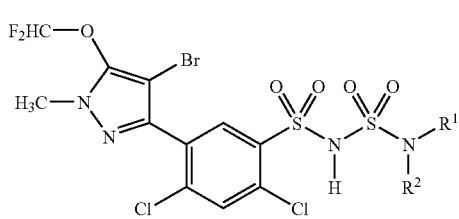

I.84

Extraordinary preference is also given to the compounds of the formula I.85, in particular to the compounds of the formulae I.85.1 to I.85.689, which differ from the corresponding compounds of the formulae I.1.1 to I.1.689 in that Q is $Q^{32}$ (where $R^{37}$=chlorine, $R^{38}$=trifluoromethyl, $R^{39}$=methyl).

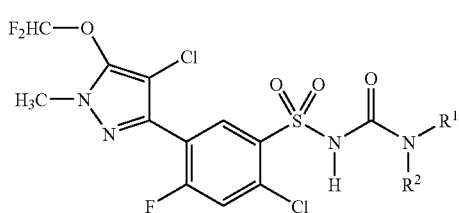

I.85

Extraordinary preference is also given to the compounds of the formula I.86, in particular to the compounds of the formulae I.86.1 to I.86.689, which differ from the corresponding compounds of the formulae I.1.1 to I.1.689 in that B is oxygen and Q is $Q^{32}$ (where $R^{37}$=chlorine, $R^{38}$=trifluoromethyl, $R^{39}$=methyl).

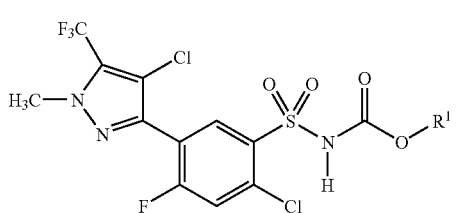

I.86

Extraordinary preference is also given to the compounds of the formula I.87, in particular to the compounds of the formulae I.87.1 to I.87.689, which differ from the corresponding compounds of the formulae I.1.1 to I.1.689 in that B is sulfur and Q is $Q^{32}$ (where $R^{37}$=chlorine, $R^{38}$=trifluoromethyl, $R^{39}$=methyl).

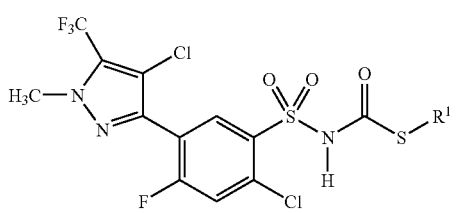

I.87

Extraordinary preference is also given to the compounds of the formula I.88, in particular to the compounds of the formulae I.88.1 to I.88.689, which differ from the corresponding compounds of the formulae I.1.1 to I.1.689 in that B is a bond and Q is $Q^{32}$ (where $R^{37}$=chlorine, $R^{38}$=trifluoromethyl, $R^{39}$=methyl).

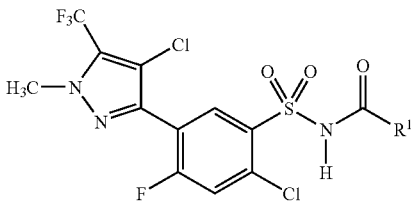

I.88

Extraordinary preference is also given to the compounds of the formula I.89, in particular to the compounds of the formulae I.89.1 to I.89.689, which differ from the corresponding compounds of the formulae I.1.1 to I.1.689 in that Y is $SO_2$ and Q is $Q^{32}$ (where $R^{37}$=chlorine, $R^{38}$=trifluoromethyl, $R^{39}$=methyl).

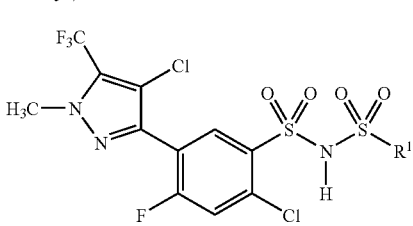

I.89

Extraordinary preference is also given to the compounds of the formula I.90, in particular to the compounds of the formulae I.90.1 to I.90.689, which differ from the corresponding compounds of the formulae I.1.1 to I.1.689 in that Y is $SO_2NR^2$ and Q is $Q^{32}$ (where $R^{37}$=chlorine, $R^{38}$=trifluoromethyl, $R^{39}$=methyl).

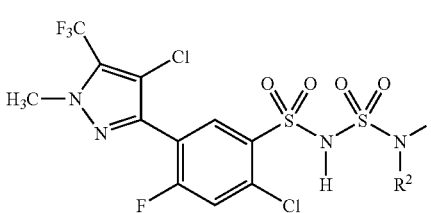

I.90

Extraordinary preference is also given to the compounds of the formula I.91, in particular to the compounds of the formulae I.91.1 to I.91.689, which differ from the corresponding compounds of the formulae I.1.1 to I.1.689 in that Q is $Q^{32}$ (where $R^{37}$=bromine, $R^{38}$=trifluoromethyl, $R^{39}$=methyl).

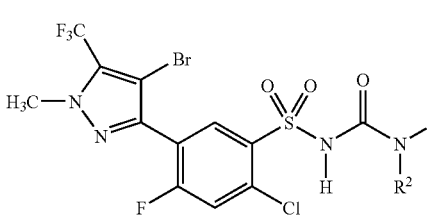

I.91

Extraordinary preference is also given to the compounds of the formula I.92, in particular to the compounds of the formulae I.92.1 to I.92.689, which differ from the corresponding compounds of the formulae I.1.1 to I.1.689 in that B is oxygen and Q is $Q^{32}$ (where $R^{37}$=bromine, $R^{38}$=trifluoromethyl, $R^{39}$=methyl).

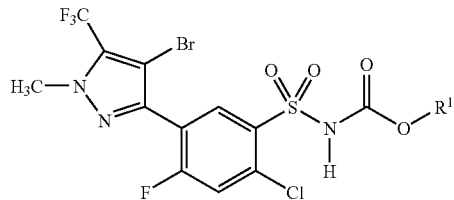

Extraordinary preference is also given to the compounds of the formula I.93, in particular to the compounds of the formulae I.93.1 to I.93.689, which differ from the corresponding compounds of the formulae I.1.1 to I.1.689 in that B is sulfur and Q is $Q^{32}$ (where $R^{37}$=bromine, $R^{38}$=trifluoromethyl, $R^{39}$=methyl).

I.93
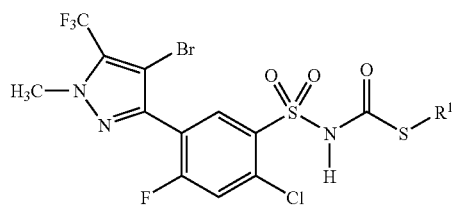

Extraordinary preference is also given to the compounds of the formula I.94, in particular to the compounds of the formulae I.94.1 to I.94.689, which differ from the corresponding compounds of the formulae I.1.1 to I.1.689 in that B is a bond and Q is $Q^{32}$ (where $R^{37}$=bromine, $R^{38}$=trifluoromethyl, $R^{39}$=methyl).

I.94
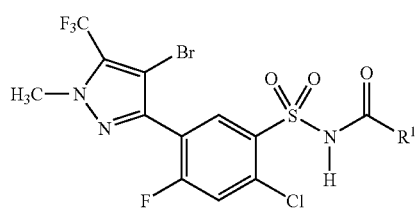

Extraordinary preference is also given to the compounds of the formula I.95, in particular to the compounds of the formulae I.95.1 to I.95.689, which differ from the corresponding compounds of the formulae I.1.1 to I.1.689 in that Y is $SO_2$ and Q is $Q^{32}$ (where $R^{37}$=bromine, $R^{38}$=trifluoromethyl, $R^{39}$=methyl).

I.95
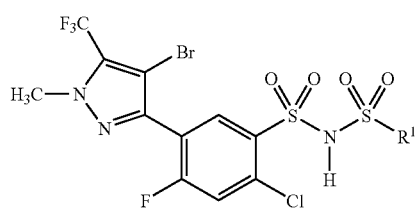

Extraordinary preference is also given to the compounds of the formula I.96, in particular to the compounds of the formulae I.96.1 to I.96.689, which differ from the corresponding compounds of the formulae I.1.1 to I.1.689 in that Y is $SO_2NR^2$ and Q is $Q^{32}$ (where $R^{37}$=bromine, $R^{38}$=trifluoromethyl, $R^{39}$=methyl).

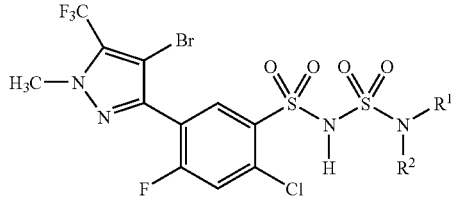

Extraordinary preference is also given to the compounds of the formula I.97, in particular to the compounds of the formulae I.97.1 to I.97.689, which differ from the corresponding compounds of the formulae I.1.1 to I.1.689 in that $X^1$ is chlorine and Q is $Q^{32}$ (where $R^{37}$=bromine, $R^{38}$=trifluoromethyl, $R^{39}$=methyl).

I.97
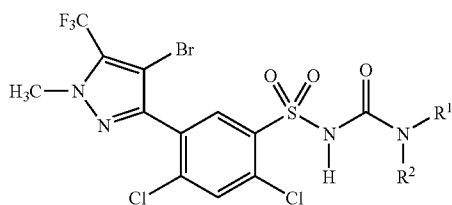

Extraordinary preference is also given to the compounds of the formula I.98, in particular to the compounds of the formulae I.98.1 to I.98.689, which differ from the corresponding compounds of the formulae I.1.1 to I.1.689 in that $X^1$ is chlorine, B is oxygen and Q is $Q^{32}$ (where $R^{37}$=bromine, $R^{38}$=trifluoromethyl, $R^{39}$=methyl).

I.98
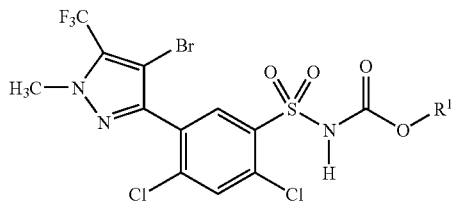

Extraordinary preference is also given to the compounds of the formula I.99, in particular to the compounds of the formulae I.99.1 to I.99.689, which differ from the corresponding compounds of the formulae I.1.1 to I.1.689 in that $X^1$ is chlorine, B is sulfur and Q is $Q^{32}$ (where $R^{37}$=bromine, $R^{38}$=trifluoromethyl, $R^{39}$=methyl).

I.99
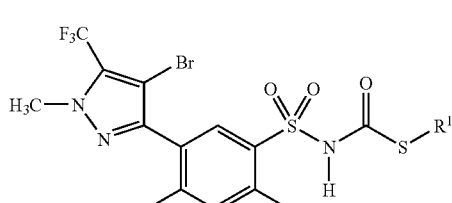

Extraordinary preference is also given to the compounds of the formula I.100, in particular to the compounds of the formulae I.100.1 to I.100.689, which differ from the corresponding compounds of the formulae I.1.1 to I.1.689 in that $X^1$ is chlorine, B is a bond and Q is $Q^{32}$ (where $R^{37}$=bromine, $R^{38}$=trifluoromethyl, $R^{39}$=methyl).

I.100

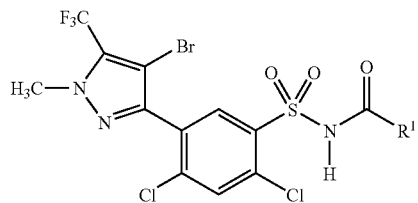

Extraordinary preference is also given to the compounds of the formula I.101, in particular to the compounds of the formulae I.101.1 to I.101.689, which differ from the corresponding compounds of the formulae I.1.1 to I.1.689 in that $X^1$ is chlorine, Y is $SO_2$ and Q is $Q^{32}$ (where $R^{37}$=bromine, $R^{38}$=trifluoromethyl, $R^{39}$=methyl).

I.101

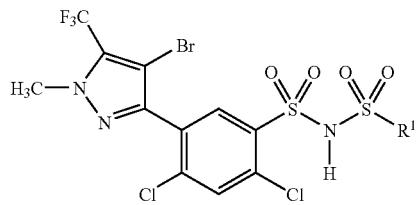

Extraordinary preference is also given to the compounds of the formula I.102, in particular to the compounds of the formulae I.102.1 to I.102.689, which differ from the corresponding compounds of the formulae I.1.1 to I.1.689 in that $X^1$ is chlorine, Y is $SO_2NR^2$ and Q is $Q^{32}$ (where $R^{37}$=bromine, $R^{38}$=trifluoromethyl, $R^{39}$=methyl).

I.102

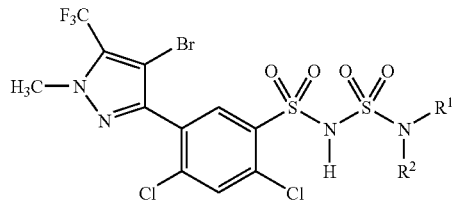

Extraordinary preference is also given to the compounds of the formula I.103, in particular to the compounds of the formulae I.103.1 to I.103.689, which differ from the corresponding compounds of the formulae I.1.1 to I.1.689 in that Q is $Q^{32}$ (where $R^{37}$=chlorine, $R^{38}$=methylsulfonyl, $R^{39}$=methyl).

I.103

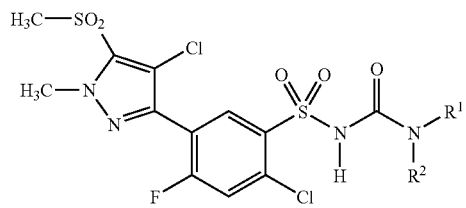

Extraordinary preference is also given to the compounds of the formula I.104, in particular to the compounds of the formulae I.104.1 to I.104.689, which differ from the corresponding compounds of the formulae I.1.1 to I.1.689 in that B is oxygen and Q is $Q^{32}$ (where $R^{37}$=chlorine, $R^{38}$=methylsulfonyl, $R^{39}$=methyl).

I.104

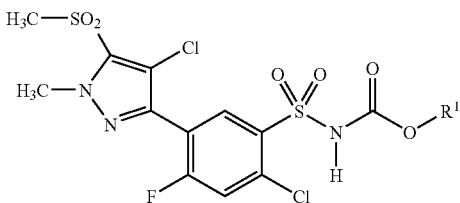

Extraordinary preference is also given to the compounds of the formula I.105, in particular to the compounds of the formulae I.105.1 to I.105.689, which differ from the corresponding compounds of the formulae I.1.1 to I.1.689 in that B is sulfur and Q is $Q^{32}$ (where $R^{37}$=chlorine, $R^{38}$=methylsulfonyl, $R^{39}$=methyl).

I.105

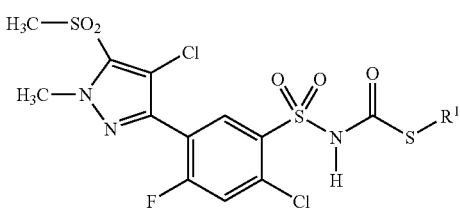

Extraordinary preference is also given to the compounds of the formula I.106, in particular to the compounds of the formulae I.106.1 to I.106.689, which differ from the corresponding compounds of the formulae I.1.1 to I.1.689 in that B is a bond and Q is $Q^{32}$ (where $R^{37}$=chlorine, $R^{38}$=methylsulfonyl, $R^{39}$=methyl).

I.106

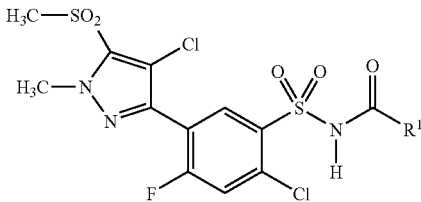

Extraordinary preference is also given to the compounds of the formula I.107, in particular to the compounds of the formulae I.107.1 to I.107.689, which differ from the corresponding compounds of the formulae I.1.1 to I.1.689 in that Y is $SO_2$ and Q is $Q^{32}$ (where $R^{37}$=chlorine, $R^{38}$=methylsulfonyl, $R^{39}$=methyl).

I.107

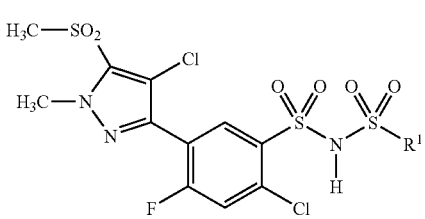

Extraordinary preference is also given to the compounds of the formula I.108, in particular to the compounds of the formulae I.108.1 to I.108.689, which differ from the corresponding compounds of the formulae I.1.1 to I.1.689 in that Y is $SO_2NR^2$ and Q is $Q^{32}$ (where $R^{37}$=chlorine, $R^{38}$=methylsulfonyl, $R^{39}$=methyl).

I.108

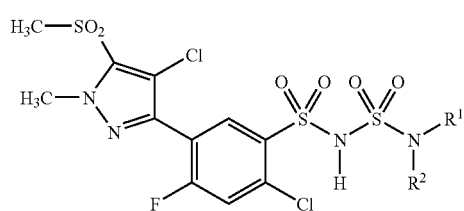

Extraordinary preference is also given to the compounds of the formula I.109, in particular to the compounds of the formulae I.109.1 to I.109.689, which differ from the corresponding compounds of the formulae I.1.1 to I.1.689 in that Q is $Q^{32}$ (where $R^{37}$=bromine, $R^{38}$=methylsulfonyl, $R^{39}$=methyl).

I.109

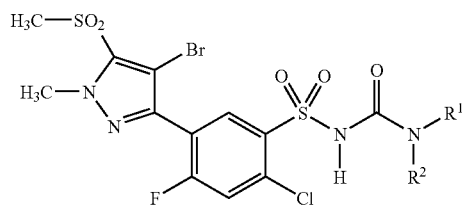

Extraordinary preference is also given to the compounds of the formula I.110, in particular to the compounds of the formulae I.110.1 to I.110.689, which differ from the corresponding compounds of the formulae I.1.1 to I.1.689 in that B is oxygen and Q is $Q^{32}$ (where $R^{37}$=bromine, $R^{38}$=methylsulfonyl, $R^{39}$=methyl).

I.110

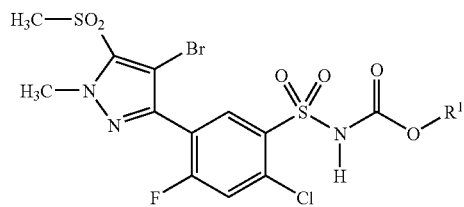

Extraordinary preference is also given to the compounds of the formula I.111, in particular to the compounds of the formulae I.111.1 to I.111.689, which differ from the corresponding compounds of the formulae I.1.1 to I.1.689 in that B is sulfur and Q is $Q^{32}$ (where $R^{37}$=bromine, $R^{38}$=methylsulfonyl, $R^{39}$=methyl).

I.111

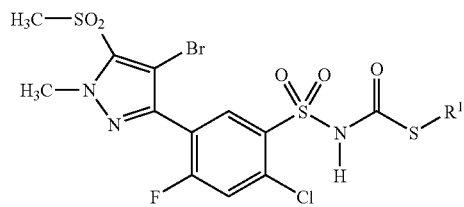

Extraordinary preference is also given to the compounds of the formula I.112, in particular to the compounds of the formulae I.112.1 to I.112.689, which differ from the corresponding compounds of the formulae I.1.1 to I.1.689 in that B is a bond and Q is $Q^{32}$ (where $R^{37}$=bromine, $R^{38}$=methylsulfonyl, $R^{39}$=methyl).

I.112

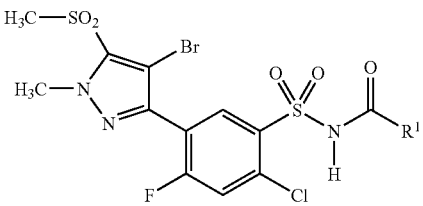

Extraordinary preference is also given to the compounds of the formula I.113, in particular to the compounds of the formulae I.113.1 to I.113.689, which differ from the corresponding compounds of the formulae I.1.1 to I.1.689 in that Y is $SO_2$ and Q is $Q^{32}$ (where $R^{37}$=bromine, $R^{38}$=methylsulfonyl, $R^{39}$=methyl).

I.113

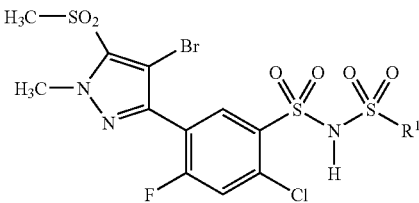

Extraordinary preference is also given to the compounds of the formula I.114, in particular to the compounds of the formulae I.114.1 to I.114.689, which differ from the corresponding compounds of the formulae I.1.1 to I.1.689 in that Y is $SO_2NR^2$ and Q is $Q^{32}$ (where $R^{37}$=bromine, $R^{38}$=methylsulfonyl, $R^{39}$=methyl).

I.114

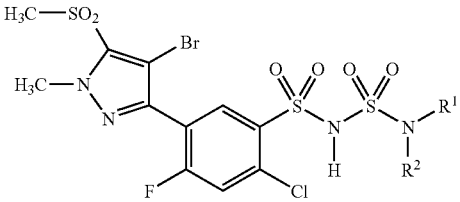

Extraordinary preference is also given to the compounds of the formula I. 115, in particular to the compounds of the formulae I.115.1 to I.115.689, which differ from the corresponding compounds of the formulae I.1.1 to I.1.689 in that $X^1$ is chlorine and Q is $Q^{32}$ (where $R^{37}$=bromine, $R^{38}$=methylsulfonyl, $R^{39}$=methyl).

I.115

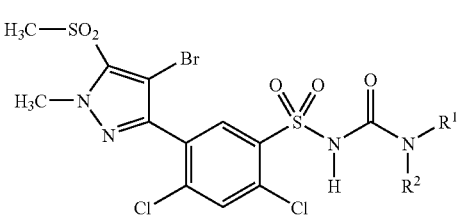

Extraordinary preference is also given to the compounds of the formula I.116, in particular to the compounds of the formulae I.116.1 to I.116.689, which differ from the corresponding compounds of the formulae I.1.1 to I.1.689 in that $X^1$ is chlorine, B is oxygen and Q is $Q^{32}$ (where $R^{37}$=bromine, $R^{38}$=methylsulfonyl, $R^{39}$=methyl).

I.116

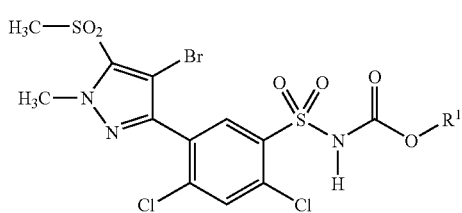

Extraordinary preference is also given to the compounds of the formula I.117, in particular to the compounds of the formulae I.117.1 to I.117.689, which differ from the corresponding compounds of the formulae I.1.1 to I.1.689 in that $X^1$ is chlorine, B is sulfur and Q is $Q^{32}$ (where $R^{37}$=bromine, $R^{38}$=methylsulfonyl, $R^{39}$=methyl).

I.117

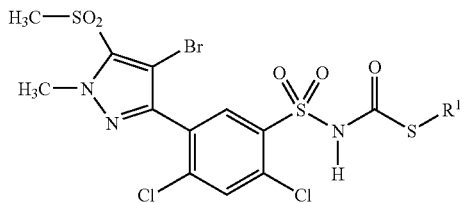

Extraordinary preference is also given to the compounds of the formula I.118, in particular to the compounds of the formulae I.118.1 to I.118.689, which differ from the corresponding compounds of the formulae I.1.1 to I.1.689 in that $X^1$ is chlorine, B is a bond and Q is $Q^{32}$ (where $R^{37}$=bromine, $R^{38}$=methylsulfonyl, $R^{39}$=methyl).

I.118

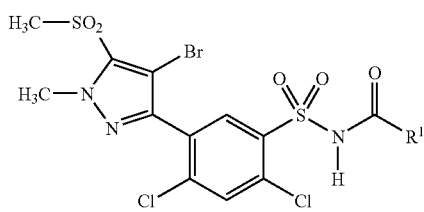

Extraordinary preference is also given to the compounds of the formula I.119, in particular to the compounds of the formulae I.119.1 to I.119.689, which differ from the corresponding compounds of the formulae I.1.1 to I.1.689 in that $X^1$ is chlorine, Y is $SO_2$ and Q is $Q^{32}$ (where $R^{37}$=bromine, $R^{38}$=methylsulfonyl, $R^{39}$=methyl).

I.119

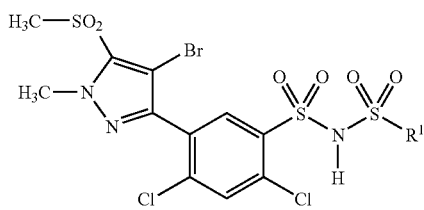

Extraordinary preference is also given to the compounds of the formula I.120, in particular to the compounds of the formulae I.120.1 to I.120.689, which differ from the corresponding compounds of the formulae I.1.1 to I.1.689 in that $X^1$ is chlorine, Y is $SO_2NR^2$ and Q is $Q^{32}$ (where $R^{37}$=bromine, $R^{38}$=methylsulfonyl, $R^{39}$=methyl).

I.102

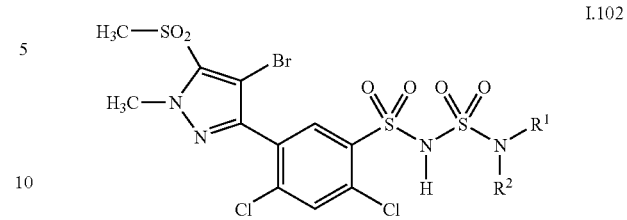

Extraordinary preference is also given to the compounds of the formula I.121, in particular to the compounds of the formulae I.121.1 to I.121.689, which differ from the corresponding compounds of the formulae I.1.1 to I.1.689 in that Q is $Q^{38}$ (where $R^{40}$=chlorine, $R^{41}$, $R^{43}$=hydrogen, $R^{42}$=trifluoromethyl).

I.121

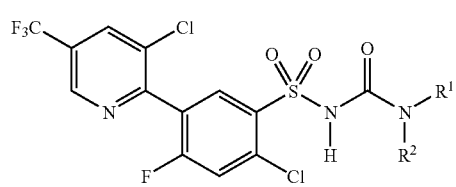

Extraordinary preference is also given to the compounds of the formula I.122, in particular to the compounds of the formulae I.122.1 to I.122.689, which differ from the corresponding compounds of the formulae I.1.1 to I.1.689 in that B is oxygen and Q is $Q^{38}$ (where $R^{40}$=chlorine, $R^{41}$, $R^{43}$=hydrogen, $R^{42}$=trifluoromethyl).

I.122

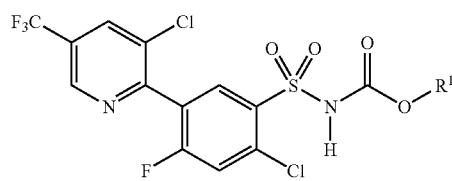

Extraordinary preference is also given to the compounds of the formula I.123, in particular to the compounds of the formulae I.123.1 to I.123.689, which differ from the corresponding compounds of the formulae I.1.1 to I.1.689 in that B is sulfur and Q is $Q^{38}$ (where $R^{40}$=chlorine, $R^{41}$, $R^{43}$=hydrogen, $R^{42}$=trifluoromethyl).

I.123

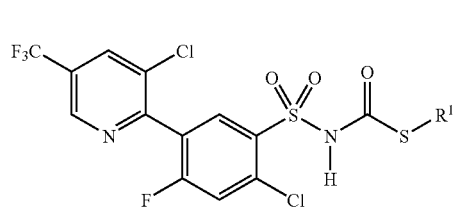

Extraordinary preference is also given to the compounds of the formula I.124, in particular to the compounds of the formulae I.124.1 to I.124.689, which differ from the corresponding compounds of the formulae I.1.1 to I.1.689 in that B is a bond and Q is $Q^{38}$ (where $R^{40}$=chlorine, $R^{41}$, $R^{43}$=hydrogen, $R^{42}$=trifluoromethyl).

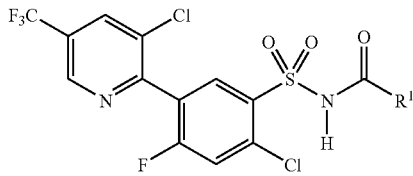

I.124

Extraordinary preference is also given to the compounds of the formula I.125, in particular to the compounds of the formulae I.125.1 to I.125.689, which differ from the corresponding compounds of the formulae I.1.1 to I.1.689 in that Y is $SO_2$ and Q is $Q^{38}$ (where $R^{40}$=chlorine, $R^{41}$, $R^{43}$=hydrogen, $R^{42}$=trifluoromethyl).

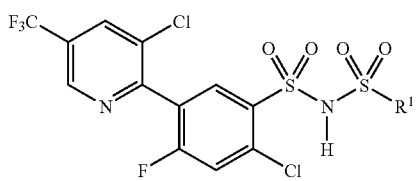

I.125

Extraordinary preference is also given to the compounds of the formula I.126, in particular to the compounds of the formulae I.126.1 to I.126.689, which differ from the corresponding compounds of the formulae I.1.1 to I.1.689 in that Y is $SO_2NR^2$ and Q is $Q^{38}$ (where $R^{40}$=chlorine, $R^{41}$, $R^{43}$=hydrogen, $R^{42}$=trifluoromethyl).

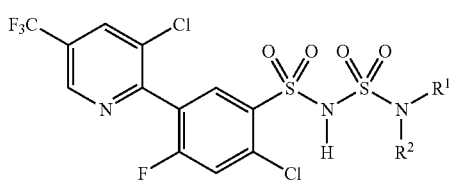

I.126

Extraordinary preference is also given to the compounds of the formula I.127, in particular to the compounds of the formulae I.127.1 to I.127.689, which differ from the corresponding compounds of the formulae I.1.1 to I.1.689 in that Q is $Q^{39}$ (where $A^1$=oxygen, $A^{15}$=sulfur, $R^{44}$, $R^{45}$=methyl).

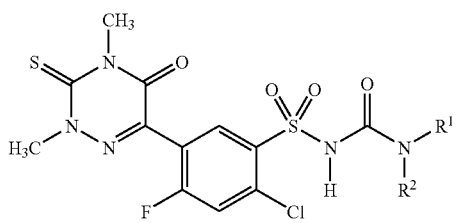

I.127

Extraordinary preference is also given to the compounds of the formula I.128, in particular to the compounds of the formulae I.128.1 to I.128.689, which differ from the corresponding compounds of the formulae I.1.1 to I.1.689 in that B is oxygen and Q is $Q^{39}$ (where $A^1$ oxygen, $A^{15}$=sulfur, $R^{44}$, $R^{45}$=methyl).

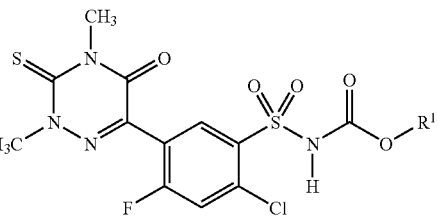

I.128

Extraordinary preference is also given to the compounds of the formula I.129, in particular to the compounds of the formulae I.129.1 to I.129.689, which differ from the corresponding compounds of the formulae I.1.1 to I.1.689 in that B is sulfur and Q is $Q^{39}$ (where $A^1$=oxygen, $A^{15}$=sulfur, $R^{44}$, $R^{45}$=methyl).

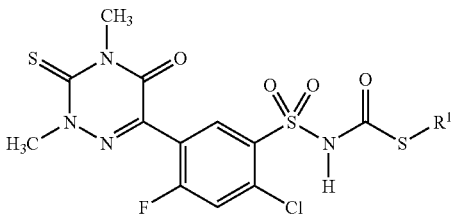

I.129

Extraordinary preference is also given to the compounds of the formula I.130, in particular to the compounds of the formulae I.130.1 to I.130.689, which differ from the corresponding compounds of the formulae I.1.1 to I.1.689 in that B is a bond and Q is $Q^{39}$ (where $A^1$=oxygen, $A^{15}$=sulfur, $R^{44}$, $R^{45}$=methyl).

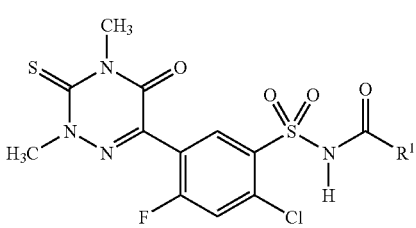

I.130

Extraordinary preference is also given to the compounds of the formula I.131, in particular to the compounds of the formulae I.131.1 to I.131.689, which differ from the corresponding compounds of the formulae I.1.1 to I.1.689 in that Y is $SO_2$ and Q is $Q^{39}$ (where $A^1$=oxygen, $A^{15}$=sulfur, $R^{44}$, $R^{45}$=methyl).

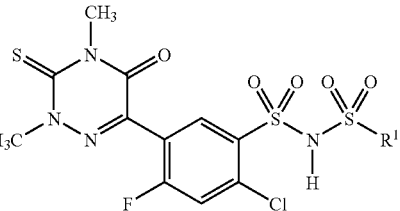

I.131

Extraordinary preference is also given to the compounds of the formula I.132, in particular to the compounds of the formulae I.132.1 to I.132.689, which differ from the corresponding compounds of the formulae I.1.1 to I.1.689 in that Y is $SO_2NR^2$ and Q is $Q^{39}$ (where $A^1$=oxygen, $A^{15}$=sulfur, $R^{44}$, $R^{45}$=methyl).

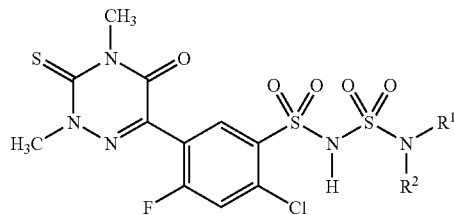

I.132

Extraordinary preference is also given to the compounds of the formula I.133, in particular to the compounds of the formulae I.133.1 to I.133.689, which differ from the corresponding compounds of the formulae I.1.1 to I.1.689 in that Q is $Q^7$ (where $A^{16}$, $A^{17}$=oxygen and $R^{46}$, $R^{47}$ form a chain —$CH_2$—$CH_2$—O—$CH_2$—).

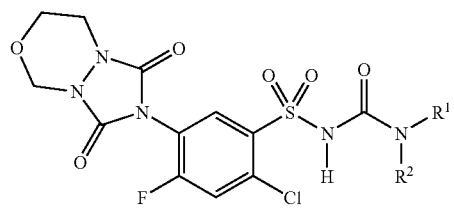

I.133

Extraordinary preference is also given to the compounds of the formula I.134, in particular to the compounds of the formulae I.134.1 to I.134.689, which differ from the corresponding compounds of the formulae I.1.1 to I.1.689 in that B is oxygen and Q is $Q^7$ (where $A^{16}$, $A^{17}$=oxygen and $R^{46}$, $R^{47}$ form a chain —$CH_2$—$CH_2$—O—$CH_2$—).

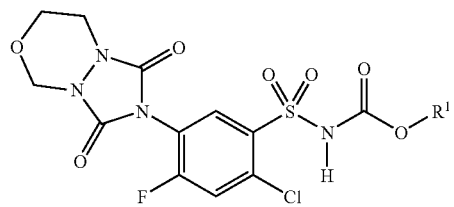

I.134

Extraordinary preference is also given to the compounds of the formula I.135, in particular to the compounds of the formulae I.135.1 to I.135.689, which differ from the corresponding compounds of the formulae I.1.1 to I.1.689 in that B is sulfur and Q is $Q^7$ (where $A^{16}$, $A^{17}$=oxygen and $R^{46}$, $R^{47}$ form a chain —$CH_2$—$CH_2$—O—$CH_2$—).

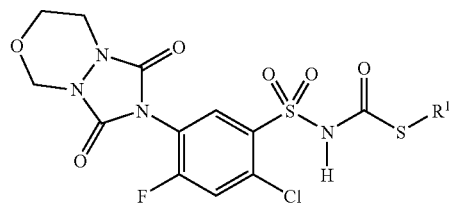

I.135

Extraordinary preference is also given to the compounds of the formula I.136, in particular to the compounds of the formulae I.136.1 to I.136.689, which differ from the corresponding compounds of the formulae I.1.1 to I.1.689 in that B is a bond and Q is $Q^7$ (where $A^{16}$, $A^{17}$=oxygen and $R^{46}$, $R^{47}$ form a chain —$CH_2$—$CH_2$—O—$CH_2$—).

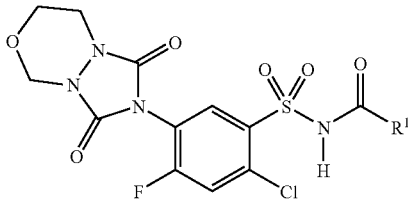

I.136

Extraordinary preference is also given to the compounds of the formula I.137, in particular to the compounds of the formulae I.137.1 to I.137.689, which differ from the corresponding compounds of the formulae I.1.1 to I.1.689 in that Y is $SO_2$ and Q is $Q^7$ (where $A^{16}$, $A^{17}$=oxygen and $R^{46}$, $R^{47}$ form a chain —$CH_2$—$CH_2$—O—$CH_2$—).

I.137

Extraordinary preference is also given to the compounds of the formula I.138, in particular to the compounds of the formulae I.138.1 to I.138.689, which differ from the corresponding compounds of the formulae I.1.1 to I.1.689 in that Y is $SO_2NR^2$ and Q is $Q^7$ (where $A^{16}$, $A^{17}$=oxygen and $R^{46}$, $R^{47}$ form a chain —$CH_2$—$CH_2$—O—$CH_2$—).

I.138

Extraordinary preference is also given to the compounds of the formula I.139, in particular to the compounds of the formulae I.139.1 to I.139.689, which differ from the corresponding compounds of the formulae I.1.1 to I.1.689 in that Q is $Q^7$ (where $A^{16}$=sulfur, $A^{17}$=oxygen and $R^{46}$, $R^{47}$ form a chain —$H_2$—$CH_2$—O—$CH_2$—).

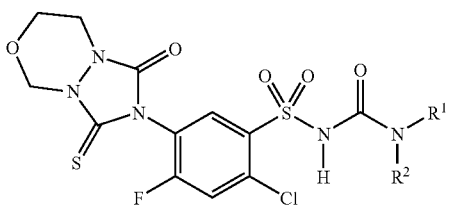

I.139

Extraordinary preference is also given to the compounds of the formula I.140, in particular to the compounds of the formulae I.140.1 to I.140.689, which differ from the corresponding compounds of the formulae I.1.1 to I.1.689 in that B is oxygen and Q is Q⁷ (where A¹⁶=sulfur, A¹⁷=oxygen and R⁴⁶, R⁴⁷ form a chain —CH₂—CH₂—O—CH₂—).

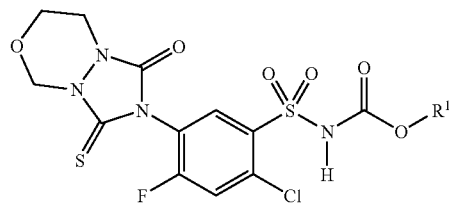

I.140

Extraordinary preference is also given to the compounds of the formula I.141, in particular to the compounds of the formulae I.141.1 to I.141.689, which differ from the corresponding compounds of the formulae I.1.1 to I.1.689 in that B is sulfur and Q is Q⁷ (where A¹⁶=sulfur, A¹⁷=oxygen and R⁴⁶, R⁴⁷ form a chain —CH₂—CH₂—O—CH₂—).

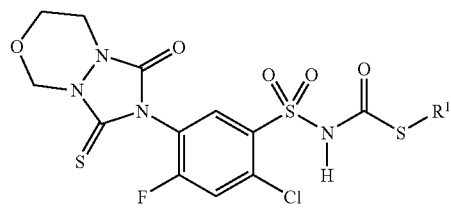

I.141

Extraordinary preference is also given to the compounds of the formula I.142, in particular to the compounds of the formulae I.142.1 to I.142.689, which differ from the corresponding compounds of the formulae I.1.1 to I.1.689 in that B is a bond and Q is Q⁷ (where A¹⁶=sulfur, A¹⁷=oxygen and R⁴⁶, R⁴⁷ form a chain —CH₂—CH₂—O—CH₂—).

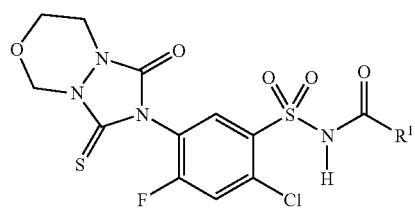

I.142

Extraordinary preference is also given to the compounds of the formula I.143, in particular to the compounds of the formulae I.143.1 to I.143.689, which differ from the corresponding compounds of the formulae I.1.1 to I.1.689 in that Y is SO₂ and Q is Q⁷ (where A¹⁶=sulfur, A¹⁷=oxygen and R⁴⁶, R⁴⁷ form a chain —CH₂—CH₂—O—CH₂—).

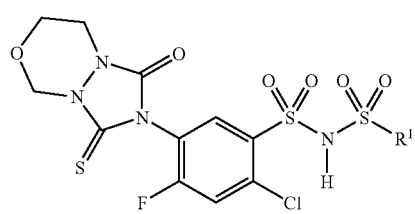

I.143

Extraordinary preference is also given to the compounds of the formula I.144, in particular to the compounds of the formulae I.144.1 to I.144.689, which differ from the corresponding compounds of the formulae I.1.1 to I.1.689 in that Y is SO₂NR² and Q is Q⁷ (where A¹⁶=sulfur, A¹⁷=oxygen and R⁴⁶, R⁴⁷ form a chain —CH₂—CH₂—O—CH₂—).

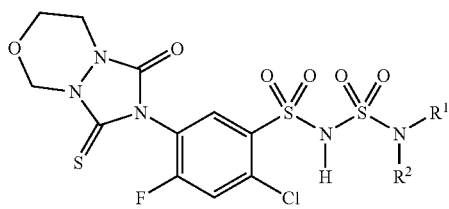

I.144

Extraordinary preference is also given to the compounds of the formula I.145, in particular to the compounds of the formulae I.145.1 to I.145.689, which differ from the corresponding compounds of the formulae I.1.1 to I.1.689 in that Q is Q⁷ (where A¹⁶, A¹⁷=sulfur and R⁴⁶, R⁴⁷ form a chain —CH₂—CH₂—O—CH₂—).

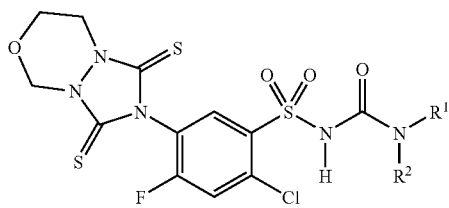

I.145

Extraordinary preference is also given to the compounds of the formula I.146, in particular to the compounds of the formulae I.146.1 to I.146.689, which differ from the corresponding compounds of the formulae I.1.1 to I.1.689 in that B is oxygen and Q is Q⁷ (where A¹⁶, A¹⁷=sulfur and R⁴⁶, R⁴⁷ form a chain —CH₂—CH₂—O—CH₂—).

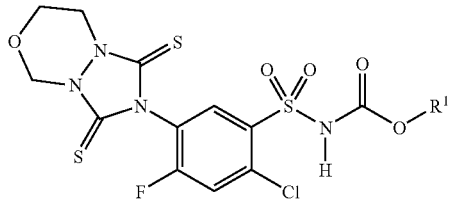

I.146

Extraordinary preference is also given to the compounds of the formula I.147, in particular to the compounds of the formulae I.147.1 to I.147.689, which differ from the corresponding compounds of the formulae I.1.1 to I.1.689 in that B is sulfur and Q is Q⁷ (where A¹⁶, A¹⁷=sulfur and R⁴⁶, R⁴⁷ form a chain —CH₂—CH₂—O—CH₂—).

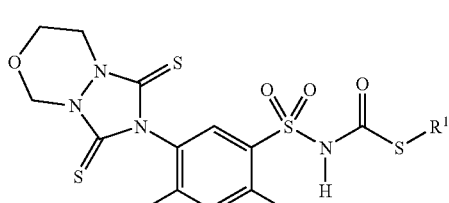

I.147

Extraordinary preference is also given to the compounds of the formula I.148, in particular to the compounds of the formulae I.148.1 to I.148.689, which differ from the corresponding compounds of the formulae I.1.1 to I.1.689 in that B is a bond and Q is $Q^7$ (where $A^{16}$, $A^{17}$=sulfur and $R^{46}$, $R^{47}$ form a chain —$CH_2$—$CH_2$—O—$CH_2$—).

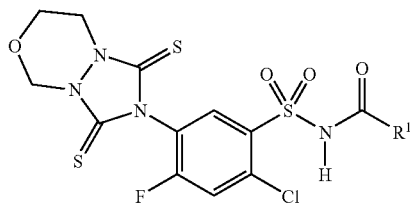

I.148

Extraordinary preference is also given to the compounds of the formula I.149, in particular to the compounds of the formulae I.149.1 to I.149.689, which differ from the corresponding compounds of the formulae I.1.1 to I.1.689 in that Y is $SO_2$ and Q is $Q^7$ (where $A^{16}$, $A^{17}$=sulfur and $R^{46}$, $R^{47}$ form a chain —$CH_2$—$CH_2$—O—$CH_2$—).

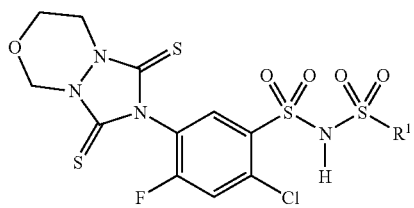

I.149

Extraordinary preference is also given to the compounds of the formula I.150, in particular to the compounds of the formulae I.150.1 to I.150.689, which differ from the corresponding compounds of the formulae I.1.1 to I.1.689 in that Y is $SO_2NR^2$ and Q is $Q^7$ (where $A^{16}$, $A^{17}$=sulfur and $R^{46}$, $R^{47}$ form a chain —$CH_2$—$CH_2$—O—$CH_2$—).

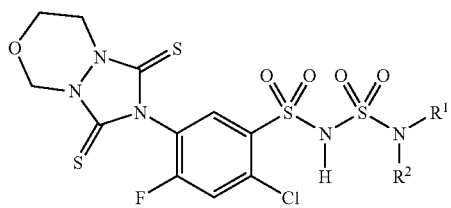

I.150

Extraordinary preference is also given to the compounds of the formula I.151, in particular to the compounds of the formulae I.151.1 to I.151.689, which differ from the corresponding compounds of the formulae I.1.1 to I.1.689 in that Q is $Q^7$ (where $A^{16}$=oxygen, $A^{17}$=sulfur and $R^{46}$, $R^{47}$ form a chain —$CH_2$—$CH_2$—O—$CH_2$—).

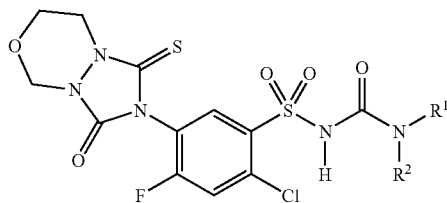

I.151

Extraordinary preference is also given to the compounds of the formula I.152, in particular to the compounds of the formulae I.152.1 to I.152.689, which differ from the corresponding compounds of the formulae I.1.1 to I.1.689 in that B is oxygen and Q is $Q^7$ (where $A^{16}$=oxygen, $A^{17}$=sulfur and $R^{46}$, $R^{47}$ form a chain —$CH_2$—$CH_2$—O—$CH_2$—).

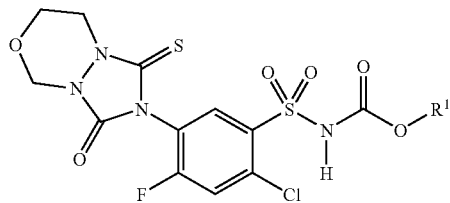

I.152

Extraordinary preference is also given to the compounds of the formula I.153, in particular to the compounds of the formulae I.153.1 to I.153.689, which differ from the corresponding compounds of the formulae I.1.1 to I.1.689 in that B is sulfur and Q is $Q^7$ (where $A^{16}$=oxygen, $A^{17}$=sulfur and $R^{46}$, $R^{47}$ form a chain —$CH_2$—$CH_2$—O—$CH_2$—).

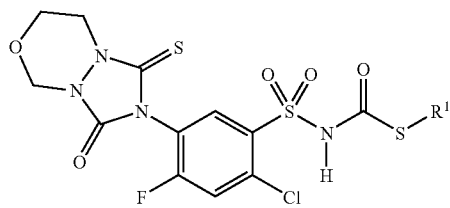

I.153

Extraordinary preference is also given to the compounds of the formula I.154, in particular to the compounds of the formulae I.154.1 to I.154.689, which differ from the corresponding compounds of the formulae I.1.1 to I.1.689 in that B is a bond and Q is $Q^7$ (where $A^{16}$=oxygen, $A^{17}$=sulfur and $R^{46}$, $R^{47}$ form a chain —$CH_2$—$CH_2$—O—$CH_2$—).

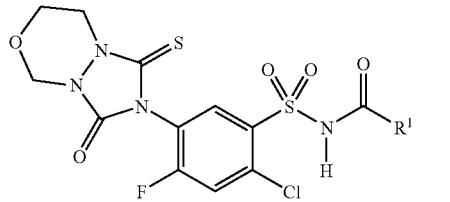

I.154

Extraordinary preference is also given to the compounds of the formula I.155, in particular to the compounds of the formulae I.155.1 to I.155.689, which differ from the corresponding compounds of the formulae I.1.1 to I.1.689 in that Y is $SO_2$ and Q is $Q^7$ (where $A^{16}$=oxygen, $A^{17}$=sulfur and $R^{46}$, $R^{47}$ form a chain —$CH_2$—$CH_2$—O—$CH_2$—).

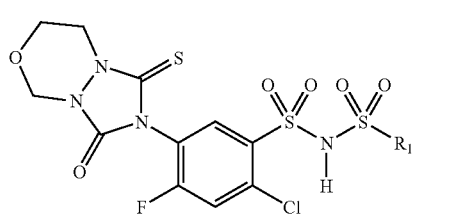

I.155

Extraordinary preference is also given to the compounds of the formula I.156, in particular to the compounds of the formulae I.156.1 to I.156.689, which differ from the corresponding compounds of the formulae I.1.1 to I.1.689 in that Y is $SO_2NR^2$ and Q is $Q^7$ (where $A^{16}$=oxygen, $A^{17}$=sulfur and $R^{46}$, $R^{47}$ form a chain —$CH_2$—$CH_2$—O—$CH_2$—).

I.156

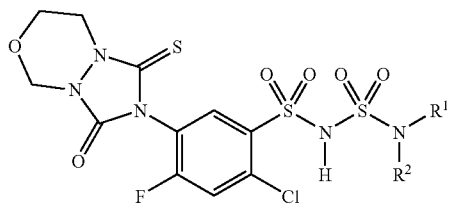

The benzenesulfonamide derivatives of the formula I can be obtained by different routes, for example by one of the processes below:

Process A

Appropriately substituted aromatic compounds of the formula VIII are, by chlorosulfonylation, converted into the corresponding benzenesulfonyl chlorides of the formula VII which are then reacted with ammonia to give the corresponding sulfonamides of the formula V. The sulfonamides of the formula V are then reacted with (thio)phosgene of the formula VI to give the benzenesulfonyl iso(thio)cyanates of the formula II which are then reacted with amines of the formula III or alcohols or thiols of the formula IV to give the desired benzenesulfonamide derivatives of the formula I, where $X^3$ is hydrogen, Y is —C(A)B and B is $NR^2$, oxygen or sulfur and the other radicals are as defined under claim 1:

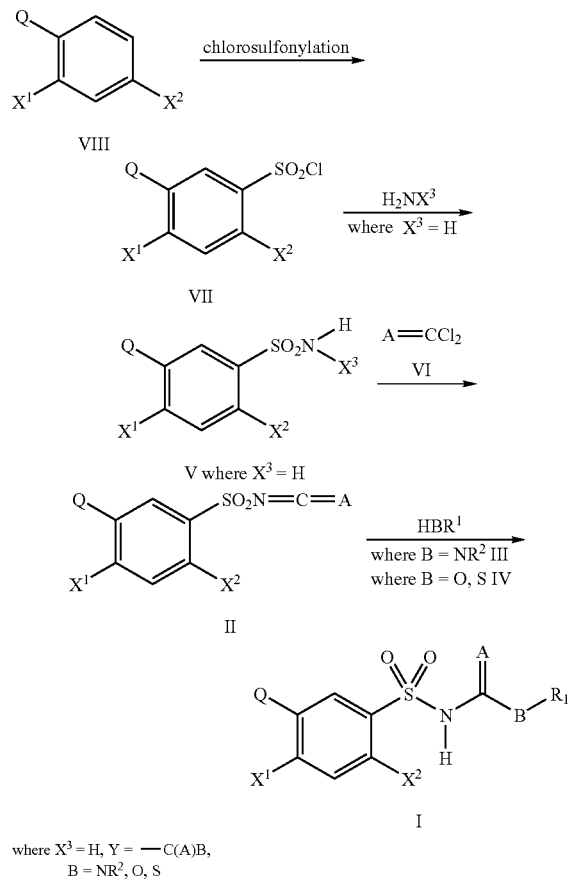

Q in formula VIII denotes the radicals $Q^1$ to $Q^{39}$ mentioned above or a substituent which is a precursor suitable for the synthesis of $Q^1$ to $Q^{39}$, for example a nitro or carboxyl group.

The chlorosulfonylation of the aromatic compounds of the formula VIII to give the corresponding benzenesulfonyl chlorides of the formula VII is usually carried out at temperatures of from 0° C. to 150° C., preferably from 20° C. to 130° C., particularly preferably from 30° C. to 110° C., using, for example, chlorosulfonic acid, sulfonyl chloride ($SO_2Cl_2$) or using sulfonyl chloride in the presence of chlorosulfonic acid in an inert organic solvent [cf. Houben-Weyl, Methoden der organischen Chemie (Methods of organic chemistry), Vol. 9, 1955, pp. 572-579].

Suitable solvents are halogenated hydrocarbons, such as methylene chloride, chloroform and chlorobenzene, nitriles, such as acetonitrile and propionitrile, and also chlorosulfonic acid, particularly preferably chlorosulfonic acid.

It is also possible to use mixtures of the solvents mentioned.

If appropriate, this reaction can also be carried out in the presence of a metal catalyst, for example aluminum chloride, analogously to a Friedel-Crafts reaction [cf. Houben-Weyl, Methoden der organischen Chemie, Vol. 9, 1955, pp. 578-579].

Suitable acids and acid catalysts include inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride.

The acid catalysts are generally employed in catalytic amounts; however, they can also be used in equimolar amounts, in excess, or, if appropriate, as solvent.

The starting materials are generally reacted with one another in equimolar amounts. It may be advantageous to use an excess of chlorosulfonic acid or sulfonyl chloride, based on VIII, or to work directly in chlorosulfonic acid, as solvent.

The reaction mixtures are worked up in a customary manner, for example by mixing with water, phase separation and, if appropriate, chromatographic purification of the crude products. Some of the intermediates and end products are obtained in the form of viscous oils which can be freed from volatile components or purified under reduced pressure and at moderately elevated temperatures. If the intermediates and end products are obtained as solids, purification can also be carried out by recrystallization or digestion.

Furthermore, it is also possible to cleave dialkyl sulfides with chlorine in the presence of water, followed by conversion into the corresponding benzenesulfonyl chlorides of the formula VII [cf. Houben-Weyl, Methoden der organischen Chemie, Vol. 9, 1955, pp. 580-582].

Analogously, it is also possible to convert thiophenols into the corresponding benzenesulfonyl chlorides of the formula VII [cf. Houben-Weyl, Methoden der organischen Chemie, Vol. 9, 1955, p. 582].

Benzenesulfonyl chlorides of the formula VII can also be prepared by reacting benzenesulfonic acids with chlorinating agents such as thionyl chloride, phosgene, phosphorus trichloride or phosphorus pentachloride [cf. Houben-Weyl, Methoden der organischen Chemie, Vol. 9, 1955, pp. 564-568].

It is also possible to convert anilides via their diazonium salts with sulfur dioxide in the presence of copper(II) chloride (Meerwein reaction) into the corresponding benzenesulfonyl chlorides of the formula VII [cf. Houben-Weyl, Methoden der organischen Chemie, Vol. 9, 1955, p. 579-580].

The starting materials required for preparing the compounds I are known from the literature [for example CAS 112, 157842; JP 01/168662] or can be prepared in accordance with the literature cited.

Benzenesulfonyl chlorides of the formula VII in which Q is $Q^7$ are known, for example, from WO 02/38562.

The preparation of benzenesulfonyl chlorides of the formula VII in which Q is $Q^{21}$ is described, for example, in U.S. Pat. No. 5,169,430.

Benzenesulfonyl chlorides of the formula VII in which Q is $Q^{32}$ are known, for example, from WO 96/15115.

The preparation of benzenesulfonyl chlorides of the formula VII in which Q is $Q^{38}$ is described, for example, in WO 95/02580.

Benzenesulfonyl chlorides of the formula VII having other radicals Q can be prepared analogously to the methods mentioned above (cf. for example JP 05/164386). Further precursors are described in Böger, Wakabayashi, Peroxidizing Herbicides, Springer Verlag 1999.

The subsequent reaction of the benzenesulfonyl chlorides of the formula VII with gaseous or aqueous ammonia to give the corresponding sulfonamides of the formula V where $X^3$=hydrogen is usually carried out at temperatures of from −10° C. to 50° C., preferably from 0° C. to 30° C., particularly preferably from 5° C. to 15° C., in an inert organic solvent, if appropriate in the presence of a base [cf. U.S. Pat. No. 5,169,430; WO 95102580; Houben-Weyl, Methoden der organischen Chemie, Vol. 9, 1955, pp. 398-400 and 605].

Ammonia is preferably used in an excess of from 200 to 230%; however, it is also possible to use an auxiliary base.

Suitable auxiliary bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide, and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines.

The bases are generally employed in catalytic amounts; however, they can also be employed in equimolar amounts, in excess or, if appropriate, as solvent.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons such as methylene chloride, 1,2-dichloroethane, chloroform and chlorobenzene, ethers, such as diethyl ether, diisopropyl ether, tert-butylmethyl ether, dioxane, anisole and tetrahydrofuran, nitriles, such as acetonitrile and propionitrile, ketones, such as acetone, methylethyl ketone, diethyl ketone and tert-butyl methyl ketone, and also dimethylformamide and dimethylacetamide, particularly preferably dioxane, tetrahydrofuran, 1,2-dichloroethane, toluene or cyclohexane.

It is also possible to use mixtures of the solvents mentioned.

Work-up and isolation of the products can be carried out in a manner known per se.

Further sulfonamides of formula V can be prepared by analogous reaction of benzenesulfonyl chlorides of the formula VII with an amine $H_2NX^3$.

Sulfonamides of the formula V, in which Q is $Q^7$ are described, for example, in WO 02/38562.

U.S. Pat. No. 5,169,430 and WO 95/02580 describe sulfonamides of the formula V in which Q is $Q^{21}$ and $Q^{28}$, respectively.

The reaction of the sulfonamides of the formula V where $X^3$=hydrogen with (thio)phosgene of the formula VI to give benzenesulfonyl iso(thio)cyanates of the formula II is usually carried out at temperatures of from 50° C. to 110° C., preferably from 60° C. to 90° C., in an inert organic solvent, if appropriate in the presence of a catalyst [cf. Houben-Weyl, Methoden der organischen Chemie, Vol. 11, 2, 1985, p. 1106; U.S. Pat. No. 4,379,769; DD 238 522].

Suitable catalysts are, for example, aliphatic isocyanates, such as, for example, n-propyl isocyanate, isopropyl isocyanate or n-butyl isocyanate.

The catalyst is generally employed in a substoichiometric amount of from 5% to 15% per mole of sulfonamide of the formula V.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, particularly preferably toluene, 1,2-dichloroethane or chlorobenzene.

It is also possible to use mixtures of the solvents mentioned.

The starting materials are generally reacted with one another in equimolar amounts. It may be advantageous to employ an excess of VI, based on V.

Work-up and isolation of the products can be carried out in a manner known per se.

The conversion of the sulfonamides of the formula V where $X^3$=hydrogen into benzenesulfonyl iso(thio)cyanates of the formula II can also be carried out using diphosgene [ClC(O)OCCl$_3$] or using carbon disulfide in phosgene.

Expediently, the sulfonamides of the formula V where $X^3$=hydrogen can also be initially pre-treated with thionyl chloride under reflux and then be reacted with phosgene to give benzenesulfonyl iso(thio)cyanates of the formula II (cf. DE 43 22 726).

Benzenesulfonyl iso(thio)cyanates of the formula II can also be prepared by reacting sulfonamides of the formula V where $X^3$=hydrogen with chlorosulfonyl isocyanate (cf. DE 31 32 944).

Benzenesulfonyl iso(thio)cyanates of the II can furthermore be prepared in a manner known per se by reacting benzenesulfonyl chlorides of the formula VII with alkali metal isocyanates (cf. U.S. Pat. No. 4,546,179).

The reaction of benzenesulfonyl iso(thio)cyanates of the II with a primary amine of the formula III or an alcohol or thiol of the formula IV to give the desired benzenesulfonamide derivatives of the formula I where $X^3$=hydrogen, Y=—C(A)B and B=NR$^2$, oxygen or sulfur is usually carried out at temperatures of from 0° C. to 120° C., preferably from 10° C. to 100° C., particularly preferably from 20° C. to 70° C., in an inert organic solvent [cf. EP 162 723].

The reaction can be carried out under atmospheric pressure or under elevated pressure (up to 50 bar), preferably from 1 to 5 bar, continuously or batchwise.

Suitable solvents are aliphatic hydrocarbons, such as pentane, hexane, cyclohexane and mixtures of $C_5$-$C_8$-alkanes; nitrated hydrocarbons, such as nitromethane, nitroethane, nitrobenzene, o-, m-, p-chloronitrobenzene and o-nitrotoluene; aromatic hydrocarbons, such as toluene, o-, m- and p-xylene; halogenated hydrocarbons, such as methylene chloride, 1,2-dichloroethane, chloroform and chlorobenzene, ethers, such as diethyl ether, diisopropyl ether, tert-butyl methyl ether, dioxane, anisole and tetrahydrofuran and also nitriles, such as acetonitrile and propionitrile, particularly preferably tetrahydrofuran, dioxane and 1,2-dichloroethane.

It is also possible to use mixtures of the solvents mentioned.

As catalyst, it is possible to add, before or during the reaction, a base, which accelerates the reaction and improves the quality of the product.

Suitable bases are, in general, organic bases, for example tertiary amines, such as trimethylamine, triethylamine, diisopropylethylamine, tri(n-propyl)amine, N-methylpiperidine, pyridine, substituted pyridines, such as collidine, lutidine and 4-dimethylaminopyridine, and also bicyclic amines. Particular preference is given to triethylamine or 1,4-diazabicyclo[2.2.2]octane.

The bases are generally employed in catalytic amounts; however, they can also be employed in equimolar amounts.

The benzenesulfonyl iso(thio)cyanates of the II are generally reacted in equimolar amounts with the primary amine of the formula III or the alcohol or thiol of the formula IV. It may be advantageous to employ an excess of III or IV, based on II.

Work-up and isolation of the products can be carried out in a manner known per se.

Process B

Sulfonamides of the formula V are reacted with (thio)carbamates of the formula IX to give the desired benzenesulfonamide derivatives of the formula I, where Y is —C(A)B and B is $NR^2$ and the other radicals are as defined under claim 1:

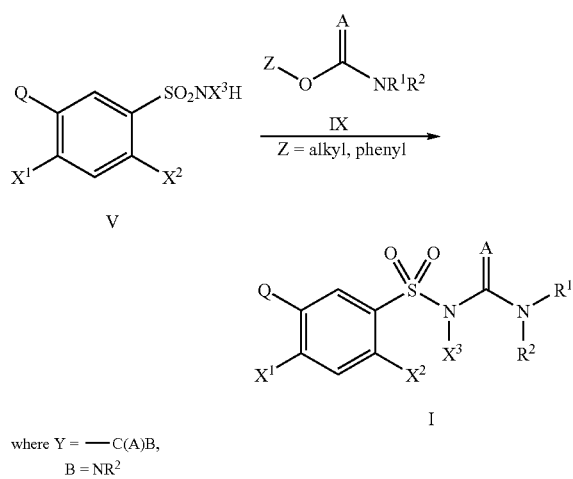

where Y = —C(A)B,
B = $NR^2$

Z in formula IX denotes a $C_1$-$C_6$-alkyl or phenyl radical, where both radicals for their part may be partially or fully halogenated and/or may carry one to three radicals from the group consisting of nitro, $C_1$-$C_4$-alkyl, $C_1$-$C_4$-alkoxy and $C_1$-$C_4$-alkoxycarbonyl.

This reaction is usually carried out at temperatures of from 0° C. to 120° C., preferably from 20° C. to 100° C., in an inert organic solvent [cf. EP 141 777 and EP 101 670].

The reaction can be carried out under atmospheric pressure or under elevated pressure (up to 50 bar), preferably at 1 to 5 bar, continuously or batchwise.

Suitable solvents are aliphatic or cycloaliphatic hydrocarbons, such as pentane, 1,2,4-trimethylpentane, 2,2,3-trimethylpentane, 2,3,3-trimethylpentane, hexane, heptane, octane, nonane, mixtures of $C_5$-$C_8$-alkanes, pinane, cyclohexane, methylcyclohexane, o-, m-, p-cymene, petroleum fractions within a boiling point range of from 70° C. to 190° C., decalin, petroleum ether, ligroin; nitrated hydrocarbons, such as nitromethane, nitroethane, nitrobenzene, o-, m-, p-chloronitrobenzene and o-nitrotoluene; aromatic hydrocarbons, such as toluene, o-, m- and p-xylene, halogenated hydrocarbons, such as 1,2-dichloroethane, 1,1-dichloroethane, 1,2-cis-dichloroethylene, 1,1,1- or 1,1,2-trichloroethane, trichloroethylene, tetrachloroethylene, 1,1,2,2- or 1,1,1,2-tetrachloroethane, pentachloroethane, dichloropropane, methylene chloride, dichlorobutane, chloroform, carbon tetrachloride, fluorobenzene, chlorobenzene, bromobenzene, iodobenzene, o-, m-, p-difluorobenzene, o-, m-, p-dichlorobenzene, o-, m-, p-dibromobenzene, o-, m-, p-chlorotoluene, 1,2,4-trichlorobenzene, chloronaphthalene, dichloronaphthalene; ethers, such as diethyl ether, ethyl propyl ether, diisopropyl ether, tert-butyl methyl ether, n-butyl ethyl ether, di-n-butyl ether, diisobutyl ether, diisoamyl ether, dioxane, cyclohexyl methyl ether, ethylene glycol dimethyl ether, β,β'-dichlorodiethyl ether, tetrahydrofuran, anisole, thioanisole, phenetol; nitriles, such as acetonitrile, propionitrile, butyronitrile, isobutyronitrile, benzonitrile, m-chlorobenzonitrile; ketones, such as acetone, methyl ethyl ketone, diethyl ketone and tert-butyl methyl ketone; esters, such as ethyl acetate, isobutyl acetate; amides, such as formamide, methylformamide, dimethylformamide; particularly preferably 1,2-dichloroethane, tetrahydrofuran, tert-butyl methyl ether and toluene.

It is also possible to use mixtures of the solvents mentioned.

As catalyst, a base can be added before or during the reaction, which accelerates the reaction and improves the quality of the product.

Suitable bases are, in general, organic bases, for example tertiary amines, such as trimethylamine, triethylamine, diisopropylethylamine, tri(n-propyl)amine, N-methylpiperidine, pyridine, substituted pyridines, such as collidine, lutidine and 4-dimethylaminopyridine, and also bicyclic amines. Particular preference is given to triethylamine and 1,4-diazabicyclo[2.2.2]octane.

The bases are generally employed in catalytic amounts; however, they can also be employed in equimolar amounts.

The sulfonamides of the formula V are generally reacted in equimolar amounts with the (thio)carbamate of the formula IX. It may be advantageous to employ an excess of IX, based on V.

The work-up and isolation of the products can be carried out in a manner known per se.

By analogous reaction with carboxylic acid derivatives $ZO(A)R^1$, it is possible to prepare benzenesulfonamide derivatives of the formula I where Y═—C(A)B and B═a bond.

Process C

Sulfonamides of the formula V can be reacted with iso(thio)cyanates of the formula X to give the desired benzenesulfonamide derivatives of the formula I where Y is —C(A)B and B is NH and the other radicals are as defined under claim 1:

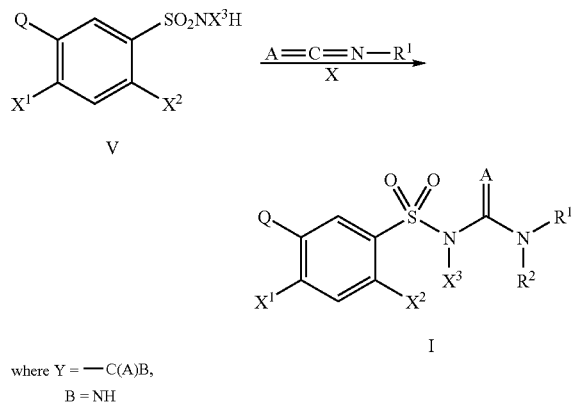

where Y = —C(A)B,
B = NH

This reaction is usually carried out at temperatures of from 0° C. to 150° C., preferably from 10° C. to 100° C., in an inert organic solvent [cf. EP 234 352].

The reaction can be carried out under atmospheric pressure or under elevated pressure (up to 50 bar), preferably at 1 to 5 bar, continuously or batchwise.

Suitable solvents are aliphatic or cycloaliphatic hydrocarbons, such as pentane, 1,2,4-trimethylpentane, 2,2,3-trimethylpentane, 2,3,3-trimethylpentane, hexane, heptane, octane, nonane, mixtures of $C_5$-$C_8$-alkanes, pinane, cyclohexane, methylcyclohexane, o-, m-, p-cymene, petroleum fractions within a boiling point range of from 70° C. to 190° C., decalin, petroleum ether, ligroin; nitrated hydrocarbons, such as nitromethane, nitroethane, nitrobenzene, o-, m-, p-chloronitrobenzene and o-nitrotoluene; aromatic hydrocarbons, such as toluene, o-, m- and p-xylene, halogenated hydrocarbons, such as 1,2-dichloroethane, 1,1-dichloroethane, 1,2-cis-dichloroethylene, 1,1,1- or 1,1,2-trichloroethane, trichloroethylene, tetrachloroethylene, 1,1,2,2- or 1,1,1,2-tetrachloroethane, pentachloroethane, dichloropropane, methylene chloride, dichlorobutane, chloroform, carbon tetrachloride, fluorobenzene, chlorobenzene, bromobenzene, iodobenzene, o-, m-, p-difluorobenzene, o-, m-, p-dichlorobenzene, o-, m-, p-dibromobenzene, o-, m-, p-chlorotoluene, 1,2,4-trichlorobenzene, chloronaphthalene, dichloronaphthalene; ethers, such as diethyl ether, ethyl propyl ether, diisopropyl ether, tert-butyl methyl ether, n-butyl ethyl ether, di-n-butyl ether, diisobutyl ether, diisoamyl ether, dioxane, cyclohexyl methyl ether, ethylene glycol dimethyl ether, β,β'-dichlorodiethyl ether, tetrahydrofuran, anisole, thioanisole, phenetol; nitriles, such as acetonitrile, propionitrile, butyronitrile, isobutyronitrile, benzonitrile, m-chlorobenzonitrile; ketones, such as acetone, methyl ethyl ketone, diethyl ketone and tert-butyl methyl ketone; esters, such as ethyl acetate, isobutyl acetate; amides, such as formamide, methylformamide, dimethylformamide; particularly preferably 1,2-dichloroethane, tetrahydrofuran, ethyl acetate, tert-butyl methyl ether, acetone and also toluene.

It is also possible to use mixtures of the solvents mentioned.

As catalyst, a base can be added before or during the reaction, which accelerates the reaction and improves the quality of the product.

Suitable bases are, in general, organic bases, for example tertiary amines, such as trimethylamine, triethylamine, diisopropylethylamine, tri(n-propyl)amine, N-methylpiperidine, pyridine, substituted pyridines, such as collidine, lutidine and 4-dimethylaminopyridine, and also bicyclic amines. Particular preference is given to triethylamine or 2,4,6-collidine.

The bases are generally employed in catalytic amounts; however, they can also be employed in equimolar amounts.

The sulfonamides of the formula V are generally reacted in equimolar amounts with an iso(thio)cyanate of the formula X. It may be advantageous to employ an excess of X, based on V.

To bring the reaction to completion, the reaction mixture may, after addition of the components, be stirred at from 0 to 120° C., preferably from 10 to 100° C., in particular from 20 to 80° C., for another 20 min. to 24 h.

Work-up and isolation of the products can be carried out in a manner known per se.

Process D

Sulfonamides of the formula V can be reacted with halides of the formula XI to give the desired benzenesulfonamide derivatives of the formula I:

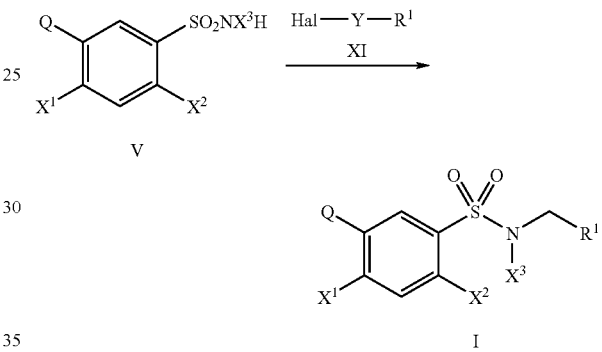

Hal in formula XI denotes halogen, such as fluorine, chlorine, bromine, particularly preferably chlorine.

This reaction is usually carried out at temperatures of from 0° C. to 150° C., preferably from 10° C. to 100° C., in an inert organic solvent [cf. JP 05/194386, CAS 120, 134277].

The reaction can be carried out under atmospheric pressure or under elevated pressure (up to 50 bar), preferably at 1 to 5 bar, continuously or batchwise.

Suitable solvents are aliphatic or cycloaliphatic hydrocarbons, such as pentane, 1,2,4-trimethylpentane, 2,2,3-trimethylpentane, 2,3,3-trimethylpentane, hexane, heptane, octane, nonane, mixtures of $C_5$-$C_8$-alkanes, pinane, cyclohexane, methylcyclohexane, o-, m-, p-cymene, petroleum fractions within a boiling point range of from 70° C. to 190° C., decalin, petroleum ether, ligroin; nitrated hydrocarbons, such as nitromethane, nitroethane, nitrobenzene, o-, m-, p-chloronitrobenzene and o-nitrotoluene; aromatic hydrocarbons, such as toluene, o-, m- and p-xylene, halogenated hydrocarbons, such as 1,2-dichloroethane, 1,1-dichloroethane, 1,2-cis-dichloroethylene, 1,1,1- or 1,1,2-trichloroethane, trichloroethylene, tetrachloroethylene, 1,1,2,2- or 1,1,1,2-tetrachloroethane, pentachloroethane, dichloropropane, methylene chloride, dichlorobutane, chloroform, carbon tetrachloride, fluorobenzene, chlorobenzene, bromobenzene, iodobenzene, o-, m-, p-difluorobenzene, o-, m-, p-dichlorobenzene, o-, m-, p-dibromobenzene, o-, m-, p-chlorotoluene, 1,2,4-trichlorobenzene, chloronaphthalene, dichloronaphthalene; ethers, such as diethyl ether, ethyl propyl ether, diisopropyl ether, tert-butyl methyl ether, n-butyl ethyl ether, di-n-butyl ether, diisobutyl ether, diisoamyl ether, dioxane, cyclohexyl methyl ether, ethylene glycol dimethyl ether, β,β'-dichlorodiethyl ether, tetrahydrofuran, anisole, thioanisole, phenetol; nitriles, such as acetonitrile, propionitrile, butyronitrile, isobutyronitrile, benzonitrile, m-chlorobenzonitrile; ketones, such as acetone, methyl ethyl ketone, diethyl ketone and tert-butyl methyl ketone; esters, such as ethyl acetate, isobutyl acetate; amides, such as formamide, methylformamide, dimethylformamide; particularly preferably 1,2-dichloroethane, tetrahydrofuran, ethyl acetate, acetonitrile and also toluene.

It is also possible to use mixtures of the solvents mentioned.

As catalyst, a base can be added before or during the reaction, which accelerates the reaction and improves the quality of the product.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, tri(n-propyl)amine, N-methylpiperidine, pyridine, substituted pyridines, such as collidine, lutidine and 4-dimethylaminopyridine, and also bicyclic amines. Particular preference is given to triethylamine or 2,4,6-collidine.

The bases are generally employed in catalytic amounts; however, they can also be employed in equimolar amounts.

The sulfonamides of the formula V are generally reacted in equimolar amounts with the isocyanate or isothiocyanate of the formula X. It may be advantageous to employ an excess of XI, based on V.

To bring the reaction to completion, the reaction mixture may, after addition of the components, be stirred at from 0 to 120° C., preferably from 10 to 100° C., in particular from 20 to 80° C., for another 20 min to 24 h.

Work-up and isolation of the products can be carried out in a manner known per se.

Analogously to process D described above, it is also possible to react sulfonamides of the formula V with anhydrides of the formula XII A[C(=A)-R¹]₂ 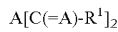 XII to give the desired benzenesulfonamide derivatives of the formula I in which Y is —C(A)B where B is a bond and the other radicals are as defined under claim 1.

Process E

Sulfonyl(thio)carbamates of the formula XIII are reacted with amines of the formula XIV to give the desired benzenesulfonamide derivatives of the formula I where Y is —C(A)B and B is NR² and the other radicals are as defined under claim 1:

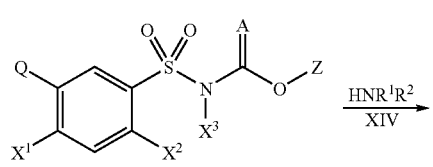

XIII

Z = alkyl, phenyl

-continued

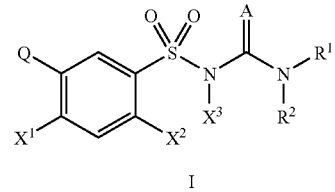

I where Y = —C(A)B,
B = NR²

Z in formula XIII is $C_1$-$C_6$-alkyl or phenyl, where both radicals may for their part be partially or fully halogenated and/or may carry one to three radicals from the group consisting of nitro, $C_1$-$C_4$-alkyl, $C_1$-$C_4$-alkoxy and $C_1$-$C_4$-alkoxycarbonyl.

This reaction is usually carried out at temperatures of from 0° C. to 120° C., preferably from 10° C. to 100° C., in an inert organic solvent [cf. EP 120 814; EP 101 407].

Suitable solvents are aliphatic or cycloaliphatic hydrocarbons, such as pentane, 1,2,4-trimethylpentane, 2,2,3-trimethylpentane, 2,3,3-trimethylpentane, hexane, heptane, octane, nonane, mixtures of $C_5$-$C_8$-alkanes, pinane, cyclohexane, methylcyclohexane, o-, m-, p-cymene, petroleum fractions within a boiling point range of from 70° C. to 190° C., decalin, petroleum ether, ligroin; nitrated hydrocarbons, such as nitromethane, nitroethane, nitrobenzene, o-, m-, p-chloronitrobenzene and o-nitrotoluene; aromatic hydrocarbons, such as toluene, o-, m- and p-xylene, halogenated hydrocarbons, such as 1,2-dichloroethane, 1,1-dichloroethane, 1,2-cis-dichloroethylene, 1,1,1- or 1,1,2-trichloroethane, trichloroethylene, tetrachloroethylene, 1,1,2,2- or 1,1,1,2-tetrachloroethane, pentachloroethane, dichloropropane, methylene chloride, dichlorobutane, chloroform, carbon tetrachloride, fluorobenzene, chlorobenzene, bromobenzene, iodobenzene, o-, m-, p-difluorobenzene, o-, m-, p-dichlorobenzene, o-, m-, p-dibromobenzene, o-, m-, p-chlorotoluene, 1,2,4-trichlorobenzene, chloronaphthalene, dichloronaphthalene; ethers, such as diethyl ether, ethyl propyl ether, diisopropyl ether, tert-butyl methyl ether, n-butyl ethyl ether, di-n-butyl ether, diisobutyl ether, diisoamyl ether, dioxane, cyclohexyl methyl ether, ethylene glycol dimethyl ether, β,β'-dichlorodiethyl ether, tetrahydrofuran, anisole, thioanisole, phenetol; nitriles, such as acetonitrile, propionitrile, butyronitrile, isobutyronitrile, benzonitrile, m-chlorobenzonitrile; ketones, such as acetone, methyl ethyl ketone, diethyl ketone and tert-butyl methyl ketone; esters, such as ethyl acetate, isobutyl acetate; amides, such as formamide, methylformamide, dimethylformamide; particularly preferably tetrahydrofuran, dioxane, dimethylformamide and also toluene.

It is also possible to use mixtures of the solvents mentioned.

As catalyst, a base can be added before or during the reaction, which accelerates the reaction and improves the quality of the product.

Suitable bases are, in general, organic bases, for example tertiary amines, such as trimethylamine, triethylamine, diisopropylethylamine, tri(n-propyl)amine, N-methylpiperidine, pyridine, substituted pyridines, such as collidine, lutidine and 4-dimethylaminopyridine, and also bicyclic amines. Particular preference is given to triethylamine and 1,4-diazabicyclo[2.2.2]octane.

The bases are generally employed in catalytic amounts; however, they can also be employed in equimolar amounts.

The sulfonylcarbamates of the formula XII are generally reacted in equimolar amounts with an amine of the formula XIV. It may be advantageous to employ an excess of XIV, based on XII.

Work-up and isolation of the products can be carried out in a manner known per se.

The starting materials required for preparing the compounds I are known from the literature [cf. for example, CAS 112, 157842; JP 01/168662], or they can be prepared in accordance with the literature cited.

Process F

Compounds of the formula I in which the radicals Q carry the substituents $R^3$, $R^4$, $R^7$, $R^{11}$, $R^{18}$, $R^{19}$, $R^{24}$, $R^{27}$, $R^{29}$, $R^{32}$, $R^{39}$, $R^{44}$-$R^{47}$ on their nitrogen atoms [these radicals denoting, inter alia, $C_1$-$C_6$-alkyl or amino, $C_1$-$C_6$-alkylamino or di($C_1$-$C_6$-alkyl)amino] can be prepared by reacting, either prior to the synthesis of the sulfonamide side chain (i.e. at the stage of the aromatic compounds of the formula VIII) or after synthesis of the sulfonamide side chain, with an alkyl halide, alkyl sulfate, alkyl tosylate or an electrophilic aminating agent of the formula XVII, analogously to the methods described in the literature.

Examples of electrophilic aminating agents of the formula XVII are 2,4-dinitrophenylhydroxylamine and o-mesitylenesulfonyl hydroxylamine.

The benzenesulfonyl chlorides of the formula VII mentioned above can be converted, for example, by action of alcohols, expediently in the presence of a base, into the corresponding benzenesulfonyl esters [Houben-Weyl, Methoden der organischen Synthese, Vol. 9, 1955, p. 663]. The benzenesulfonyl esters can then be alkylated or aminated on the free nitrogen atoms of the corresponding radicals Q. Subsequently, the benzenesulfonyl esters can be hydrolyzed again [cf. Kocienski, Protecting groups, Thieme-Verlag 1994; Greene, Wuts, Protecting groups in organic synthesis, Wiley 1999; Houben-Weyl, Methoden der organischen Chemie, Vol. E5 part 1, 1985, p. 223f.).

By way of example, an amination at the radical $Q=Q^{21}$ is shown here. The aminations of the other radicals Q and alkylations at the radicals Q can be carried out analogously. This route affords, for example, sulfonic acids of the formula XVI. These can then be converted using methods known from the literature into the desired benzenesulfonamide derivatives of the formula I.

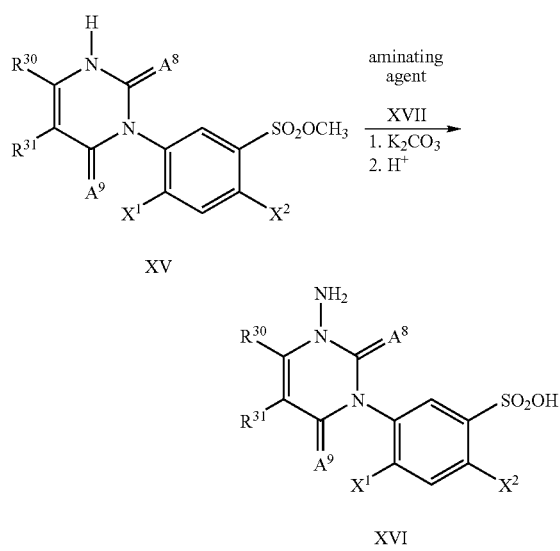

This reaction is usually carried out at temperatures of from 10° C. to 80° C., preferably from 20° C. to 40° C., in an inert organic solvent in the presence of a base [cf. DE 19 652 431; WO 01/83459].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide, dimethyl formamide and dimethylacetamide, particularly preferably tetrahydrofuran, dioxane, acetonitrile and also dimethylformamide.

It is also possible to use mixtures of the solvents mentioned.

Suitable bases are, in general, inorganic compounds, for example alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to potassium carbonate and also calcium carbonate.

The bases are generally employed in catalytic amounts; however, they can also be employed in equimolar amounts, in excess or, if appropriate, as solvent.

The starting materials are generally reacted with one another in equimolar amounts. However, it may also be advantageous to employ an excess of XVII, based on XV.

Work-up and isolation of the products can be carried out in a manner known per se.

The starting materials required for preparing the compounds I are known from the literature [for example CAS 112, 157842; JP 01168662], or they can be prepared in accordance with the literature cited.

The present invention also provides benzenesulfonyl iso (thio)cyanates of the formula II

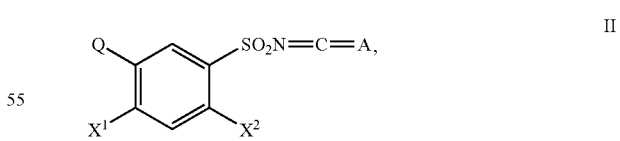

where $X^1$, $X^2$, A and Q are as defined under claim 1.

The particularly preferred embodiments of the intermediates with respect to the variables correspond to those of the radicals $X^1$, $X^2$, A and Q of formula I.

Particular preference is given to intermediates of the formula IV in which
$X^1$ is hydrogen, fluorine or chlorine;
  particularly preferably hydrogen or fluorine;
  especially preferably fluorine;

$X^2$ is hydrogen, cyano, CS—$NH_2$ or halogen;
particularly preferably hydrogen, halogen such as fluorine and chlorine;
especially preferably chlorine; and Q is $Q^1$, $Q^2$, $Q^5$, $Q^7$, $Q^8$, $Q^{10}$, $Q^{12}$, $Q^{13}$, $Q^{17}$, $Q^{20}$, $Q^{21}$, $Q^{22}$, $Q^{23}$, $Q^{24}$, $Q^{27}$, $Q^{31}$, $Q^{32}$, $Q^{34}$, $Q^{38}$ or $Q^{39}$,
particularly preferably $Q^1$, $Q^2$, $Q^5$, $Q^7$, $Q^8$, $Q^{10}$, $Q^{12}$, $Q^{13}$, $Q^{17}$, $Q^{20}$, $Q^{21}$, $Q^{22}$, $Q^{24}$, $Q^{27}$, $Q^{31}$, $Q^{32}$, $Q^{38}$ or $Q^{39}$,
especially preferably $Q^5$, $Q^7$, $Q^{21}$, $Q^{22}$, $Q^{27}$, $Q^{32}$, $Q^{38}$ or $Q^{39}$,
with extraordinary preference $Q^7$, $Q^{21}$, $Q^{22}$, $Q^{27}$, $Q^{32}$, $Q^{38}$ or $Q^{39}$,
with most extraordinary preference $Q^{21}$, $Q^{32}$ or $Q^{38}$.

PREPARATION EXAMPLES

Example 1

2-Chloro-5-[3,6-dihydro-3-methyl-2,6-dioxo-4-trifluoromethyl-(2H)-pyrimidin-1-yl]-benzenesulfonamide

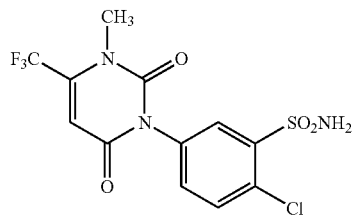

With stirring, 1.6 g (93.8 mmol) of ammonia gas were, at 0° C., introduced into a mixture of 18 g (44.6 mmol) of 2-chloro-5-[3,6-dihydro-3-methyl-2,6-dioxo-4-trifluoromethyl-(2H)-pyrimidin-1-yl]-benzenesulfonylchloride in tetrahydrofuran (THF). Then, at 10° C., ethyl acetate was added and the mixture was acidified with 1N hydrochloric acid. The phases were separated and the aqueous phase was extracted, and the combined organic phases were then washed, dried and the solvent was removed. Customary purification methods gave 14.4 g (82.4% of theory) of the title compound (m.p.: 257-258° C.).

Example 2

2-Chloro-4-fluoro-5-[3,6-dihydro-3-methyl-2,6-dioxo-4-trifluoromethyl-(2H)-pyrimidin-1-yl]benzenesulfonylisocyanate

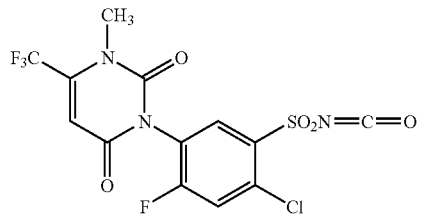

At 60° C., 7.4 g (62.3 mmol) of thionyl chloride were added dropwise with stirring to a suspension of 10.0 g (24.9 mmol) of 2-chloro-4-fluoro-5-[3,6-dihydro-3-methyl-2,6-dioxo-4-trifluoromethyl-(2H)-pyrimidin-1-yl]-benzenesulfonylamide in 1,2-dichloroethane. The mixture was then boiled under reflux for 4 h. The mixture was then cooled to 60° C., a catalytic amount of pyridine was added and phosgene was introduced under reflux for 12 h until a clear solution was obtained. After cooling to 30° C., the product was freed from the solvent. This gave 11.6 g (98% of theory) of the title compound.

$^1$H-NMR (400 MHz, $CDCl_3$) δ [ppm]=8.12 (d, 1H), 7.55 (d, 1H), 6.38 (s, 1H), 3.57 (s, 3H).

Example 3

2-Chloro-5-[3,6-dihydro-3-methyl-2,6-dioxo-4-trifluoromethyl-(2H)-pyrimidin-1-yl]-benzenesulfonyl isocyanate

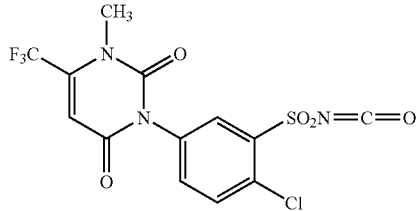

10.0 g (26.1 mmol) of 2-chloro-5-[3,6-dihydro-3-methyl-2,6-dioxo-4-trifluoromethyl-(2H)-pyrimidin-1-yl]-benzenesulfonamide were reacted analogously to the method described in Example 2. This gave 13.4 g (99% of theory) of the title compound.

$^1$H-NMR (400 MHz, $CDCl_3$) δ [ppm]=8.02 (s, 1H), 7.76 (d, 2H), 7.5 (d, 1H), 6.38 (s, 1H), 3.70 (s, 3H).

Example 4 (No. 3.32)

Benzyl{2-chloro-4-fluoro-5-[3,6-dihydro-3-methyl-2,6-dioxo-4-trifluoromethyl-(2H)-pyrimidin-1-yl]phenyl}sulfonylcarbamate

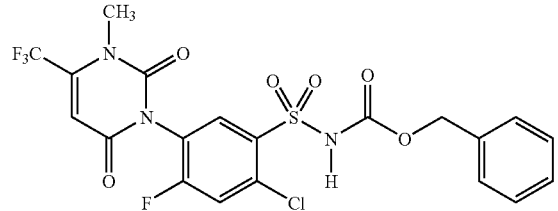

With stirring, 0.6 g (1.4 mmol) of 2-chloro-4-fluoro-5-[3,6-dihydro-3-methyl-2,6-dioxo-4-trifluoromethyl-(2H)-pyrimidin-1-yl]benzenesulfonylisocyanate in 1,2-dichloroethane was added to a solution of 0.15 g (1.4 mmol) of benzyl alcohol in methylene chloride, and the reaction mixture was stirred overnight. Removal of the solvent and customary purification methods gave 0.4 g (52% of theory) of the title compound as a colorless solid (m.p.: 231-232° C.).

Example 5 (No. 2.26)

3-[4-Chloro-2-fluoro-5-{[isopropyl(methyl)amino]carbonylaminosulfonyl}phenyl]-1-methyl-2,4-dioxo-6-trifluoromethyl-1,2,3,4-tetrahydropyrimidine

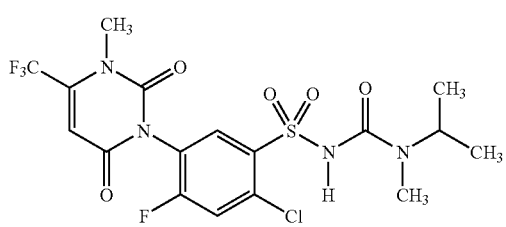

With stirring, 1.0 g (2.34 mmol) of 2-chloro-4-fluoro-5-[3,6-dihydro-3-methyl-2,6-dioxo-4-trifluoromethyl-(2H)-pyrimidin-1-yl]benzenesulfonyl isocyanate in 1,2-dichloroethane was added to a solution of 0.34 g (4.68 mmol) of N-methylisopropylamine in 1,2-dichloroethane, and the mixture was stirred overnight. The reaction mixture was concentrated, the residue was taken up in methylene chloride and 0.5N hydrochloric acid was added. The organic phase was then dried and the solvent was removed. This gave 0.5 g (42% of theory) of the title compound as a colorless solid (m.p.: 145° C.).

Example 6 (No. 4.5)

N-isobutynyl-[2-chloro-5-(3,6-dihydro-3-methyl-2,6-dioxo-4-trifluoromethyl-1-(2H)-pyrimidinyl)]benzenesulfonamide

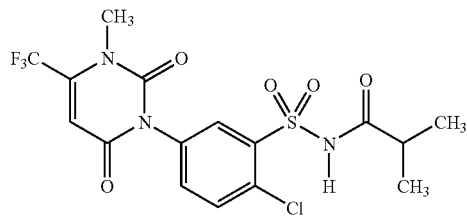

With stirring, 0.15 g (1.43 mmol) of isobutyryl chloride was added to a mixture of 0.5 g (1.3 mmol) of 2-chloro-4-fluoro-5-[3,6-dihydro-3-methyl-2,6-dioxo-4-trifluoromethyl-(2H)-pyrimidin-1-yl]benzenesulfonyl isocyanate, 0.26 g (2.61 mmol) of triethylamine and catalytic amounts of N,N-dimethylaminopyridine in methylene chloride, and the mixture was stirred overnight. The reaction mixture was washed with 1N hydrochloric acid and dried and the solvent was removed. This gives 0.6 g (96% of theory) of the title compound as a colorless solid (m.p.: 114-116° C.).

In addition to the compounds above, Tables 2 to 4 list further benzenesulfonamide derivatives of the formula I which were prepared or are preparable in a manner similar to the processes described above.

TABLE 2

| No. | $X^1$ | $X^2$ | $R^1$ | $R^2$ | $R^{29}$ | m.p. [° C.] |
|---|---|---|---|---|---|---|
| 2.1 | H | Cl | $CH_3$ | H | $CH_3$ | |
| 2.2 | H | Cl | $CH_3$ | H | $NH_2$ | |
| 2.3 | H | Cl | $CH_3$ | $CH_3$ | $CH_3$ | |
| 2.4 | H | Cl | $CH_3$ | $CH_3$ | $NH_2$ | |
| 2.5 | H | Cl | $OCH_3$ | $CH_3$ | $CH_3$ | 95 |
| 2.6 | H | Cl | $C_2H_5$ | H | $CH_3$ | |
| 2.7 | H | Cl | $C_2H_5$ | H | $NH_2$ | |
| 2.8 | H | Cl | $C_2H_5$ | $C_2H_5$ | $CH_3$ | |
| 2.9 | H | Cl | $CH_2CH_2CH_3$ | H | $CH_3$ | |
| 2.10 | H | Cl | $CH_2CH_2CH_3$ | H | $NH_2$ | |
| 2.11 | H | Cl | $CH(CH_3)_2$ | H | $CH_3$ | |
| 2.12 | H | Cl | $CH(CH_3)_2$ | $CH_3$ | $CH_3$ | 197 |
| 2.13 | H | Cl | $CH_2=CH—CH_2$ | H | $CH_3$ | |
| 2.14 | H | Cl | 4-methoxy-6-methyl-pyrimidin-2-yl | H | $CH_3$ | 209-211 |
| 2.15 | H | Cl | 4,6-dimethoxy-pyrimidin-2-yl | H | $CH_3$ | 208-212 |
| 2.16 | H | Cl | 4-methoxy-6-methyl-1,3,5-triazin-2-yl | H | $CH_3$ | 146-175 |
| 2.17 | F | Cl | $CH_3$ | H | $CH_3$ | 228-230 |
| 2.18 | F | Cl | $CH_3$ | H | $NH_2$ | |
| 2.19 | F | Cl | $CH_3$ | $CH_3$ | $CH_3$ | 198-205 |
| 2.20 | F | Cl | $CH_3$ | $CH_3$ | $NH_2$ | |
| 2.21 | F | Cl | $C_2H_5$ | H | $CH_3$ | |
| 2.22 | F | Cl | $C_2H_5$ | H | $NH_2$ | |
| 2.23 | F | Cl | $C_2H_5$ | $CH_3$ | $CH_3$ | |
| 2.24 | F | Cl | $CH_2CH_2CH_3$ | H | $CH_3$ | |
| 2.25 | F | Cl | $CH_2CH_2CH_3$ | $CH_3$ | $CH_3$ | |
| 2.26 | F | Cl | $CH(CH_3)_2$ | $CH_3$ | $CH_3$ | 145 (decomposition) |
| 2.27 | F | Cl | $CH(CH_3)_2$ | $CH(CH_3)_2$ | $CH_3$ | 179-181 |
| 2.28 | F | Cl | $CH(CH_3)C=CH$ | $CH_3$ | $CH_3$ | 160-165 |
| 2.29 | F | Cl | $C_6H_5$ | H | $CH_3$ | 160 |
| 2.30 | F | Cl | —$(CH_2)_5$— | | $CH_3$ | |
| 2.31 | F | Cl | —$(CH_2)_6$— | | $CH_3$ | |
| 2.32 | Cl | Cl | $CH_3$ | H | $CH_3$ | 234-235 |
| 2.33 | Cl | Cl | $CH_3$ | $CH_3$ | $CH_3$ | |
| 2.34 | Cl | Cl | $CH_3$ | $CH_3$ | $NH_2$ | |
| 2.35 | Cl | Cl | $C_2H_5$ | H | $CH_3$ | |
| 2.36 | Cl | Cl | $CH_2CH_2CH_3$ | H | $CH_3$ | |
| 2.37 | F | Cl | $CH(CH_3)_2$ | H | $NH_2$ | |

TABLE 3

$$\text{Structure 3: pyrimidine-2,4-dione with } R^{29} \text{ on N, } CF_3 \text{ group, linked to phenyl ring bearing } X^1, X^2 \text{ substituents and sulfonamide } -SO_2NH-C(=A)-B-R^1$$

| No. | $X^1$ | $X^2$ | A | B | $R^1$ | $R^{29}$ | m.p. [° C.] |
|---|---|---|---|---|---|---|---|
| 3.1 | H | Cl | O | O | $CH_3$ | $CH_3$ | 120-148 |
| 3.2 | H | Cl | O | O | $C_2H_5$ | $CH_3$ | 189-190 |
| 3.3 | H | Cl | O | O | $CH_2CH_2CH_3$ | $CH_3$ | |
| 3.4 | H | Cl | O | O | $CH(CH_3)_2$ | $CH_3$ | |
| 3.5 | H | Cl | O | O | $(CH_2)_3CH_3$ | $CH_3$ | 194-195 |
| 3.6 | H | Cl | O | O | $CH(CH_3)CH_2CH_3$ | $CH_3$ | |
| 3.7 | H | Cl | O | O | $CH_2CH(CH_3)_2$ | $CH_3$ | |
| 3.8 | H | Cl | O | O | $C(CH_3)_3$ | $CH_3$ | |
| 3.9 | H | Cl | O | O | $(CH_2)_4CH_3$ | $CH_3$ | |
| 3.10 | H | Cl | O | O | cyclopentyl | $CH_3$ | 114-116 |
| 3.11 | H | Cl | O | O | $CH_2CH_2Cl$ | $CH_3$ | |
| 3.12 | H | Cl | O | O | $(CH_2)OCH_3$ | $CH_3$ | |
| 3.13 | H | Cl | O | O | $(CH_2)SCH_3$ | $CH_3$ | |
| 3.14 | H | Cl | O | O | $CH_2CH_2CN$ | $CH_3$ | |
| 3.15 | H | Cl | O | S | $CH_3$ | $CH_3$ | |
| 3.16 | H | Cl | O | S | $C_2H_5$ | $CH_3$ | |
| 3.17 | H | Cl | O | S | $CH_2CH_2CH_3$ | $CH_3$ | |
| 3.18 | F | Cl | O | O | $CH_3$ | $CH_3$ | 120-135 |
| 3.19 | F | Cl | O | O | $C_2H_5$ | $CH_3$ | 228-231 |
| 3.20 | F | Cl | O | O | $CH_2CH_2CH_3$ | $CH_3$ | 203 |
| 3.21 | F | Cl | O | O | $CH(CH_3)_2$ | $CH_3$ | 228-230 |
| 3.22 | F | Cl | O | O | $(CH_2)_3CH_3$ | $CH_3$ | 238 |
| 3.23 | F | Cl | O | O | $CH(CH_3)CH_2CH_3$ | $CH_3$ | 195-198 |
| 3.24 | F | Cl | O | O | $CH_2CH(CH_3)_2$ | $CH_3$ | 233-235 |
| 3.25 | F | Cl | O | O | $C(CH_3)_3$ | $CH_3$ | 185 |
| 3.26 | F | Cl | O | O | $(CH_2)_4CH_3$ | $CH_3$ | 235 |
| 3.27 | F | Cl | O | O | cyclopentyl | $CH_3$ | 214 |
| 3.28 | F | Cl | O | O | $CH_2CH_2Cl$ | $CH_3$ | |
| 3.29 | F | Cl | O | O | $(CH_2)OCH_3$ | $CH_3$ | |
| 3.30 | F | Cl | O | O | $(CH_2)SCH_3$ | $CH_3$ | |
| 3.31 | F | Cl | O | O | $CH_2CH_2CN$ | $CH_3$ | |
| 3.32 | F | Cl | O | O | $CH_2C_6H_5$ | $CH_3$ | 231-232 |
| 3.33 | F | Cl | O | S | $CH_3$ | $CH_3$ | |
| 3.34 | F | Cl | O | S | $C_2H_5$ | $CH_3$ | |
| 3.35 | F | Cl | O | S | $CH_2CH_2CH_3$ | $CH_3$ | |
| 3.36 | Cl | Cl | O | S | $CH_3$ | $CH_3$ | |
| 3.37 | Cl | Cl | O | S | $C_2H_5$ | $CH_3$ | |
| 3.38 | Cl | Cl | O | S | $CH_2CH_2CH_3$ | $CH_3$ | |
| 3.39 | Cl | Cl | O | O | $CH_3$ | $CH_3$ | 218-220 |
| 3.40 | Cl | Cl | O | O | $C_2H_5$ | $CH_3$ | 235-237 |
| 3.41 | F | Cl | O | O | $CH_2COOCH_3$ | $CH_3$ | 142-160 |
| 3.42 | F | Cl | O | O | $C(CH_3)_2CH_2OCH_3$ | $CH_3$ | 178 |

TABLE 4

| No. | $X^1$ | $X^2$ | $R^1$ | $R^{29}$ | m.p. [° C.] |
|---|---|---|---|---|---|
| 4.1 | H | Cl | H | $CH_3$ | |
| 4.2 | H | Cl | $CH_3$ | $CH_3$ | |
| 4.3 | H | Cl | $C_2H_5$ | $CH_3$ | |
| 4.4 | H | Cl | $CH_2CH_2CH_3$ | $CH_3$ | |

TABLE 4-continued

4

$$\text{Structure: } F_3C\text{-pyrimidinedione-N}(R^{29})\text{-phenyl}(X^1, X^2)\text{-SO}_2\text{-NH-C(O)-}R^1$$

| No. | $X^1$ | $X^2$ | $R^1$ | $R^{29}$ | m.p. [° C.] |
|---|---|---|---|---|---|
| 4.5 | H | Cl | $CH(CH_3)_2$ | $CH_3$ | 114-116 |
| 4.6 | H | Cl | $(CH_2)_3CH_3$ | $CH_3$ | |
| 4.7 | H | Cl | $CH(CH_3)CH_2CH_3$ | $CH_3$ | |
| 4.8 | H | Cl | $CH_2CH(CH_3)_2$ | $CH_3$ | |
| 4.9 | H | Cl | cyclopentyl | $CH_3$ | |
| 4.10 | H | Cl | $CH_3$ | $NH_2$ | |
| 4.11 | H | Cl | $C_2H_5$ | $NH_2$ | |
| 4.12 | H | Cl | $CH_2CH_2CH_3$ | $NH_2$ | |
| 4.13 | F | Cl | $CH_3$ | $CH_3$ | 269 (decomposition) |
| 4.14 | F | Cl | $C_2H_5$ | $CH_3$ | 229-230 |
| 4.15 | F | Cl | $CH_2CH_2CH_3$ | $CH_3$ | |
| 4.16 | F | Cl | $CH(CH_3)_2$ | $CH_3$ | 243-245 |
| 4.17 | F | Cl | $CH_2Cl$ | $CH_3$ | |
| 4.18 | F | Cl | $CF_3$ | $CH_3$ | |
| 4.19 | F | Cl | $C_6H_5$ | $CH_3$ | |
| 4.20 | F | Cl | 2-Cl—$C_6H_4$ | $CH_3$ | |
| 4.21 | F | Cl | 3-Cl—$C_6H_4$ | $CH_3$ | |
| 4.22 | F | Cl | 4-Cl—$C_6H_4$ | $CH_3$ | |
| 4.23 | F | Cl | $CH_2(4\text{-}CH_3\text{—}C_6H_4)$ | $CH_3$ | |
| 4.24 | Cl | Cl | $CH_3$ | $CH_3$ | 275-277 |
| 4.25 | Cl | Cl | $C_2H_5$ | $CH_3$ | 225-230 |
| 4.26 | Cl | Cl | $CH_2CH_2CH_3$ | $CH_3$ | |
| 4.27 | Cl | Cl | $CH_2CH(CH_3)_2$ | $CH_3$ | |
| 4.28 | Cl | Cl | $CH_3$ | $NH_2$ | |
| 4.29 | Cl | Cl | $C_2H_5$ | $NH_2$ | |
| 4.30 | Cl | Cl | $CH_2CH_2CH_3$ | $NH_2$ | |

Biological Activity

The benzenesulfonamide derivatives of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I, or the herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum*, (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds of the formula I may also be used in crops which tolerate the action of herbicides owing to breeding, including genetic engineering methods.

Furthermore, the benzenesulfonamide derivatives of the formula I and their agriculturally useful salts are also suitable for the desiccation and/or defoliation of plants.

As desiccants, they are particularly suitable for desiccating the above-ground parts of crop plants such as potatoes; oilseed rape, sunflowers and soybeans. This allows completely mechanical harvesting of these important crop plants.

Also of economic interest is
the concentrated, within a certain time, fruit drop or the reduction of the adherence of the fruits to the plant, for example in the case of citrus fruit, olives or other species and varieties of pomaceous fruit, stone fruit and hard-shelled fruit, thus facilitating the harvesting of these fruits, and also
the controlled defoliation of useful plants, in particular cotton.

The drop, promoted by using compounds of the formula I according to the invention and agriculturally useful salts thereof, is a result of the formation of abscission tissue between fruits or leaves and the shoot of the plants.

The defoliation of cotton is of very particular economic interest, since it facilitates harvesting. At the same time, the reduced period of time within which the individual plants mature results in a better quality of the harvested fiber material.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

The herbicidal compositions comprise a herbicidally effective amount of at least one compound of the formula I or an agriculturally useful salt of I and auxiliaries customary for formulating crop protection agents.

Essentially, suitable inert auxiliaries include:
mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably 0.01 to 95% by weight, of at least one active compound. The active compounds are employed in a purity of from 90% to 100%, preferably 95% to 100% (according to the NMR spectrum).

The formulation examples below illustrate the production of such preparations:

I 20 parts by weight of an active compound of the formula I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of the formula I.

II 20 parts by weight of an active compound of the formula I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of the formula I.

III 20 parts by weight of an active compound of the formula I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of the formula I.

IV 20 parts by weight of an active compound of the formula I are mixed thoroughly with 3 parts by weight of sodium diisobutylnaphthalene sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound of the formula I.

V 3 parts by weight of an active compound of the formula I are mixed with 97 parts by weight of finely divided kaolin. This gives a dust which comprises 3% by weight of the active compound of the formula I.

VI 20 parts by weight of an active compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of an active compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of an active compound of the formula I is dissolved in a mixture composed of 80 parts by weight of cyclohexanone and 20 parts by weight of Wettol$^R$ EM 31 (=nonionic emulsifier based on ethoxylated castor oil). This gives a stable emulsion concentrate.

The herbicidal compositions or the compounds of the formula I can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably 0.01 to 1.0 kg/ha of active substance (a.s.), depending on the control target, the season, the target plants and the growth stage.

To widen the activity spectrum and to achieve synergistic effects, the benzenesulfonamide derivatives of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-hetaroyl/aroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenyl-propionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

Herbicidal Efficacy

The herbicidal activity of the benzenesulfonamide derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, emulsified or suspended in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of 3 to 15 cm, depending on the plant form, and only then treated with the active compounds, emulsified or suspended in water. The test plants were for this purpose either sown directly and grown in the same containers, or they were first grown separately as seedlings and transplanted into the test containers a few days prior to treatment.

The application rate for the pre- and post-emergence treatment was from 62.5 to 3.1 g of a.s./ha.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were composed of the following species:

| Scientific Name | Common Name |
| --- | --- |
| Abutilon theophrasti | Velvet leaf |
| Amaranthus retroflexus | Pigweed |
| Chenopodium album | Common lambsquarters |
| Commelina benghalensis | Bengal commelina |
| Galium aparine | Cleavers harrif |
| Ipomoea hederacea | Morning glory |
| Pharbitis purpurea | Common morning glory |
| Polygonum convolvulus | Wild buckwheat |
| Polygonum persicaria | Ladysthumb |
| Solanum nigrum | Common nightshade |

At application rates of 12.5 and 6.2 g/ha, the compounds 3.1 and 3.18 (Table 3) showed very good pre-emergence activity against the unwanted plants pigweed, common lambsquarters, common morning glory and wild buckwheat.

Furthermore, compounds 3.24 (Table 3) and 4.16 (Table 4), when applied by the pre-emergence method at application rates of 6.2 and 3.1 g/ha, effected very good control of the unwanted plants velvet leaf, pigweed, common lambsquarters and morning glory.

The effectiveness of compound 3.32 (Table 3), when applied by the pre-emergence method at application rates of 62.5 and 31.2 g/ha, was very good against the unwanted plants velvet leaf, pigweed, common lambsquarters and common nightshade.

At application rates of 15.6 and 7.8 g/ha, the compounds 3.27, 3.19, 3.20 and 3.22 (Table 3) showed very good post-emergence activity against the unwanted plants pigweed, common lambsquarters, common morning glory and ladysthumb.

Furthermore, compounds 2.29 (Table 2) and 3.26 (Table 3), when applied by the post-emergence method at application rates of 15.6 and 7.8 g/ha, effected very good control of the unwanted plants pigweed, common lambsquarters and common morning glory.

The effectiveness of compound 3.42 (Table 3), when applied by the post-emergence method at application rates of 15.63 g/ha, was very good against the unwanted plants velvet leaf, common morning glory and ladiesthumb.

At application rates of 15.63 g/ha, the compounds 3.41 (Table 3) and 4.14 (Table 4) showed very good post-emergence activity against the unwanted plants pigweed, cleavers harrif and ladiesthumb.

Furthermore, compound 2.17 (Table 2), when applied by the post-emergence method at application rates of 15.63 g/ha, effected very good control of the unwanted plants velvet leaf, common lambsquarters and *Bengal commelina*.

The effectiveness of compound 2.28 (Table 2), when applied by the post-emergence method at application rates of 15.63 g/ha, was very good against the unwanted plants pigweed, common lambsquarters and common morning glory.

At application rates of 15.63 g/ha, the compound 2.27 (Table 2) showed very good post-emergence activity against the unwanted plants pigweed and common morning glory.

USE EXAMPLES

Desiccant/Defoliant Efficacy

The test plants used were young 4-leaf cotton plants (without cotyledons) which were grown under greenhouse conditions (rel. atmospheric humidity 50 to 70%; day/night temperature 27/20° C.).

The leaves of the young cotton plants were sprayed to runoff point with aqueous preparations of the active compounds (with addition of 0.15% by weight of the fatty alcohol alkoxylate Plurafac® LF 700[1]), based on the spray liquor). The amount of water applied was 1000 l/ha (converted). After 13 days, the number of leaves that had been shed and the degree of defoliation in % were determined.

[1] A low-foam nonionic surfactant from BASF AG

The untreated control plants did not lose any leaves.

We claim:

1. A compound which is a benzenesulfonamide derivative of the formula I

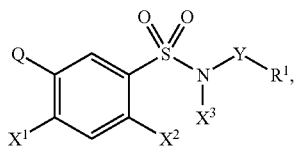

I in which the variables are as defined below:
$X^1$ is halogen;
$X^2$ is chlorine;
$X^3$ is hydrogen;
Y is a group —C(A)B;
A is oxygen;
B is oxygen or sulfur;
$R^1$ is hydrogen, $C_1$-$C_8$-alkyl, $C_3$-$C_7$-cycloalkyl, or phenyl-$C_1$-$C_4$ alkyl, wherein $C_1$-$C_8$ alkyl may be substituted by $C_1$-$C_8$alkoxy or $C_1$-$C_8$ alkoxycarbonyl;
Q is

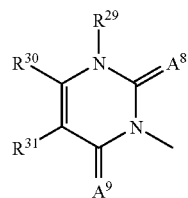

$Q^{21}$ $A^8$ and $A^9$ are oxygen;
$R^{29}$ is hydrogen, $C_1$-$C_6$ alkyl, or amino;
$R^{30}$ is $C_1$-$C_6$ haloalkyl;
$R^{31}$ is hydrogen;
or an agriculturally useful salt thereof.

2. A compound of claim 1, in which $X^1$ is fluorine or chlorine.

3. A process for preparing a compound of claim 1, where $X^3$ is hydrogen, which comprises reacting a benzenesulfonyl iso(thio)cyanate of the formula II

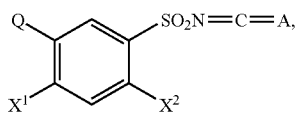

II where $X^1$, $X^2$, A and Q are as defined in claim 1, with an alcohol or thiol of the formula IV HB$R^1$ III where B=N$R^2$ IV where B=O, S where $R^1$ is as defined in claim 1.

4. An herbicidal composition comprising a herbicidally effective amount of at least one benzenesulfonamide derivative of the formula I or an agriculturally useful salt of I according to claim 1 and further comprising auxiliaries customary for formulating crop protection agents.

5. An herbicidal composition for the desiccation and/or defoliation of plants, comprising such an amount of at least one benzenesulfonamide derivative of the formula I or an agriculturally useful salt of I according to claim 1 that acts as a desiccant and/or defoliant, and further comprising auxiliaries customary for formulating crop protection agents.

6. A process for preparing herbicidally effective compositions, which comprises mixing a herbicidally effective amount of at least one benzenesulfonamide derivative of the formula I or an agriculturally useful salt of I according to claim 1 and auxiliaries customary for formulating crop protection agents.

7. A process for preparing compositions having desiccant and/or defoliant action, which comprises mixing a desiccant and/or defoliant effective amount of at least one compound according to claim 1 and auxiliaries customary for formulating crop protection agents.

8. A method for controlling unwanted vegetation, wherein a herbicidally effective amount of at least one benzenesulfonamide derivative of the formula I or an agriculturally useful salt of I according to claim 1 is allowed to act on the unwanted vegetation, their habitat and/or on their seeds.

9. A method for the desiccation and/or defoliation of plants, which comprises allowing a desiccant and/or defoliant effective amount of at least one compound according to claim 1 to act on the plants.

* * * * *